United States Patent
Ma et al.

(10) Patent No.: US 11,588,115 B2
(45) Date of Patent: Feb. 21, 2023

(54) NITROGEN-CONTAINING COMPOUND, ORGANIC ELECTROLUMINESCENT DEVICE AND ELECTRONIC APPARATUS

(71) Applicant: Shaanxi Lighte Optoelectronics Material Co., Ltd., Xi'an (CN)

(72) Inventors: Tiantian Ma, Xi'an (CN); Lei Yang, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 17/623,484

(22) PCT Filed: Jul. 23, 2020

(86) PCT No.: PCT/CN2020/103869
§ 371 (c)(1),
(2) Date: Dec. 28, 2021

(87) PCT Pub. No.: WO2021/135181
PCT Pub. Date: Jul. 8, 2021

(65) Prior Publication Data
US 2022/0285628 A1    Sep. 8, 2022

(30) Foreign Application Priority Data

Dec. 31, 2019 (CN) .......................... 201911423492.4
May 13, 2020 (CN) .......................... 202010402229.3

(51) Int. Cl.
*C07D 209/86* (2006.01)
*C07D 401/04* (2006.01)
(Continued)

(52) U.S. Cl.
CPC ........ *H01L 51/0072* (2013.01); *C07D 209/86* (2013.01); *C07D 401/04* (2013.01);
(Continued)

(58) Field of Classification Search
CPC .. C07D 401/04; C07D 401/10; C07D 401/14; C07D 403/04; C07D 403/10;
(Continued)

(56) References Cited

FOREIGN PATENT DOCUMENTS

CN         104039778 A      9/2014
CN         107459466 A     12/2017
(Continued)

OTHER PUBLICATIONS

International Search Report from corresponding International Application No. PCT/CN2020/103869, dated Sep. 29, 2020, 4 pages.

*Primary Examiner* — Vu A Nguyen
(74) *Attorney, Agent, or Firm* — Tucker Ellis LLP

(57) ABSTRACT

The present disclosure provides a nitrogen-containing compound, an organic electroluminescent device and an electronic apparatus, belonging to the technical field of organic materials. The nitrogen-containing compound of the present disclosure has a carbazole structure and a fluorenyl group, two cooperating with each other and has a high first triplet energy level. Therefore, the nitrogen-containing compound of the present disclosure is suitable for use as a host material of a light-emitting in an organic electroluminescent device. The nitrogen-containing compound can improve the performance of the organic electroluminescent device.

12 Claims, 1 Drawing Sheet

(51) Int. Cl.
| | | |
|---|---|---|
| *C07D 401/10* | (2006.01) | |
| *C07D 401/14* | (2006.01) | |
| *C07D 403/04* | (2006.01) | |
| *C07D 403/10* | (2006.01) | |
| *C07D 403/14* | (2006.01) | |
| *C07D 405/04* | (2006.01) | |
| *C07D 405/10* | (2006.01) | |
| *C07D 405/14* | (2006.01) | |
| *C07D 409/04* | (2006.01) | |
| *C07D 409/10* | (2006.01) | |
| *C07D 409/14* | (2006.01) | |
| *C07D 471/04* | (2006.01) | |
| *C07D 491/048* | (2006.01) | |
| *C07D 495/04* | (2006.01) | |
| *C09K 11/06* | (2006.01) | |
| *H01L 51/00* | (2006.01) | |
| *H01L 51/50* | (2006.01) | |

(52) U.S. Cl.
CPC ......... *C07D 401/10* (2013.01); *C07D 403/04* (2013.01); *C07D 405/04* (2013.01); *C07D 405/10* (2013.01); *C07D 471/04* (2013.01); *C07D 491/048* (2013.01); *C09K 11/06* (2013.01); *H01L 51/0056* (2013.01); *H01L 51/0058* (2013.01); *H01L 51/0067* (2013.01); *H01L 51/0071* (2013.01); *H01L 51/0073* (2013.01); *C07B 2200/05* (2013.01); *C09K 2211/1018* (2013.01); *H01L 51/5012* (2013.01); *H01L 2251/552* (2013.01)

(58) Field of Classification Search
CPC .. C07D 403/14; C07D 405/04; C07D 405/10; C07D 405/14; C07D 409/04; C07D 409/10; C07D 409/14; C07D 471/04; C07D 491/048; C07D 495/04; H01L 51/0056; H01L 51/0058; H01L 51/0067; H01L 51/0071; H01L 51/0073; H01L 51/5012; C07B 2200/05; C09K 2211/1018; C09K 11/06
See application file for complete search history.

(56) References Cited

FOREIGN PATENT DOCUMENTS

| | | | | |
|---|---|---|---|---|
| CN | 110128279 A | 8/2019 | | |
| CN | 110467536 A | 11/2019 | | |
| CN | 110615759 A | 12/2019 | | |
| CN | 111138298 A | * | 5/2020 | ........... C07B 59/001 |
| CN | 111377853 A | * | 7/2020 | ........... C07D 213/16 |
| WO | 2013172835 A1 | 11/2013 | | |
| WO | 2020046049 A1 | 3/2020 | | |

* cited by examiner

NITROGEN-CONTAINING COMPOUND, ORGANIC ELECTROLUMINESCENT DEVICE AND ELECTRONIC APPARATUS

CROSS REFERENCE TO RELATED APPLICATIONS

The present application claims the priority of Chinese patent application CN201911423492.4, filed on Dec. 31, 2019, and claims the priority of Chinese patent application CN202010402229.3, filed on May 13, 2020, the entirety of which is incorporated herein by reference.

TECHNICAL FIELD

The present application relates to the technical field of organic materials, and in particular to a nitrogen-containing compound, an organic electroluminescent device and an electronic apparatus.

BACKGROUND

An organic electroluminescent device, for example, an organic light-emitting diode (OLED), usually includes a cathode and an anode which are disposed oppositely, and a functional layer disposed between the cathode and the anode. The functional layer consists of multi-layer organic or inorganic films, and generally includes an organic light-emitting layer, a hole transport layer located between the organic light-emitting layer and the anode, and an electron transport layer located between the organic light-emitting layer and the cathode. When voltage is applied at both cathode and anode, an electric field is generated at both electrodes. Under the action of the electric field, electrons on the side of cathode will move towards an electroluminescent layer, and holes on the side of anode will also move towards an emitting layer, then electrons and holes bind with each other on the electroluminescent layer to form excitons. The excitons are in an excited state to release energy to the outside, such that the electroluminescent layer emits light to the outside.

In the prior art, CN104039778A and the like have disclosed a material for preparing an emitting layer in an organic electroluminescent device. However, it is still necessary to continuously research and develop a novel material, thus further improving the performance of the organic electroluminescent device.

The above information disclosed in the background part is only used to enhance the understanding to the background of the present application, and thus may include the information not constituting the prior art known to a person skilled in the art.

SUMMARY

The objective of the present application is to provide a nitrogen-containing compound, an organic electroluminescent device and an electronic apparatus, thereby improving the performance of the organic electroluminescent device.

To achieve the objective of the present application, the present application adopts the following technical solution:

According to one aspect of the present application, provided is a nitrogen-containing compound, and the nitrogen-containing compound has a structural formula as shown in the chemical formula 1:

Chemical formula 1

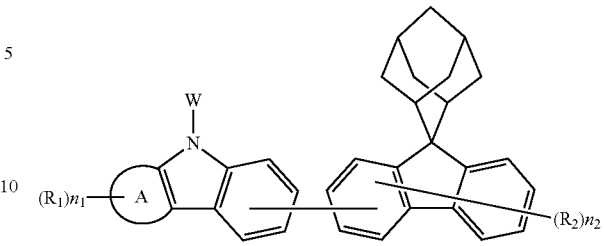

wherein, the ring A is a benzene ring, a fused aromatic ring having 10 to 14 ring-forming carbon atoms, or a fused heteroaromatic ring having 8 to 12 ring-forming carbon atoms;

$R_1$ and $R_2$ are the same or different from each other, and are each independently selected from deuterium, halogen, cyano, haloalkyl with 1 to 12 carbon atoms, alkyl with 1 to 12 carbon atoms, cycloalkyl with 3 to 12 carbon atoms, alkoxy with 1 to 12 carbon atoms, alkylthio with 1 to 12 carbon atoms, alkylsilyl with 1 to 12 carbon atoms, aryl with 6 to 20 carbon atoms and heteroaryl with 3 to 20 carbon atoms;

$n_1$ is the quantity of a substituent $R_1$, and $n_2$ is the quantity of a substituent $R_2$; when the ring A is the benzene ring, $n_1$ is 0, 1, 2, 3 or 4; when the ring A is the fused aromatic ring or the fused heteroaromatic ring, $n_1$ is 0, 1, 2, 3, 4, 5, 6, 7 or 8; when $n_1$ is greater than 1, any two of $R_1$ are the same or different;

$n_2$ is 0, 1, 2, 3, 4, 5 or 6; when $n_2$ is greater than 1, any two of $R_2$ are the same or different;

W is selected from substituted or unsubstituted aryl with 6 to 40 carbon atoms, substituted or unsubstituted heteroaryl with 3 to 40 carbon atoms.

According to a second aspect of the present application, provided is an organic electroluminescent device, and the organic electroluminescent device includes an anode and a cathode disposed oppositely, and an organic light-emitting layer disposed between the anode and the cathode; and the organic light-emitting layer includes the above nitrogen-containing compound.

According to a third aspect of the present application, provided is an electronic apparatus, and the electronic apparatus includes the above organic electroluminescent device.

The compound of the present disclosure contains a carbazole ring in its structure; the carbazole structure may be conjugated with a fluorenyl group to form a large conjugated plane. The large-plane conjugated structure as the core of the nitrogen-containing compound has stronger rigidity, such that the nitrogen-containing compound of the present disclosure has a high first triplet energy level, therefore, the nitrogen-containing compound of the present disclosure is suitable for as a host material of a luminescent layer in an organic electroluminescent device. Adamantyl and fluorenyl are connected by spiro, which may greatly increase the electron cloud density of the large-plane conjugated structure by hyperconjugation effect, thus enhancing the hole mobility of the nitrogen-containing compound, being conducive to promoting the transmission balance between holes and electrons in an emitting layer, and improving the efficiency performance of the organic electroluminescent device. Moreover, the promotion of the hole transport performance of the nitrogen-containing compound may improve the recombination rate of holes and electrons in an organic light-emitting layer, reduce or avoid that electrons transport to the hole transport layer after passing through the organic light-emitting layer, thereby effectively protecting the material of the hole transport layer from the impact of electrons and prolonging the lifetime of the organic electroluminescent device. Furthermore, adamantyl connected on fluorenyl by spiro has a large space volume and stronger rigidity, and thus may reduce the interaction force between the large-plane conjugated structures, decrease t-t stacking between molecules, and adjust the degree of intermolecular stacking, such that the nitrogen-containing compound may have a more stable amorphous state during film formation to improve the film-forming property of the nitrogen-containing compound, thus further prolonging the lifetime of the organic electroluminescent device.

BRIEF DESCRIPTION OF THE DRAWINGS

The exemplary embodiments will be described in detail with reference to the accompanying drawings to make the above and other features and advantages of the present disclosure more apparent.

Figure 1:
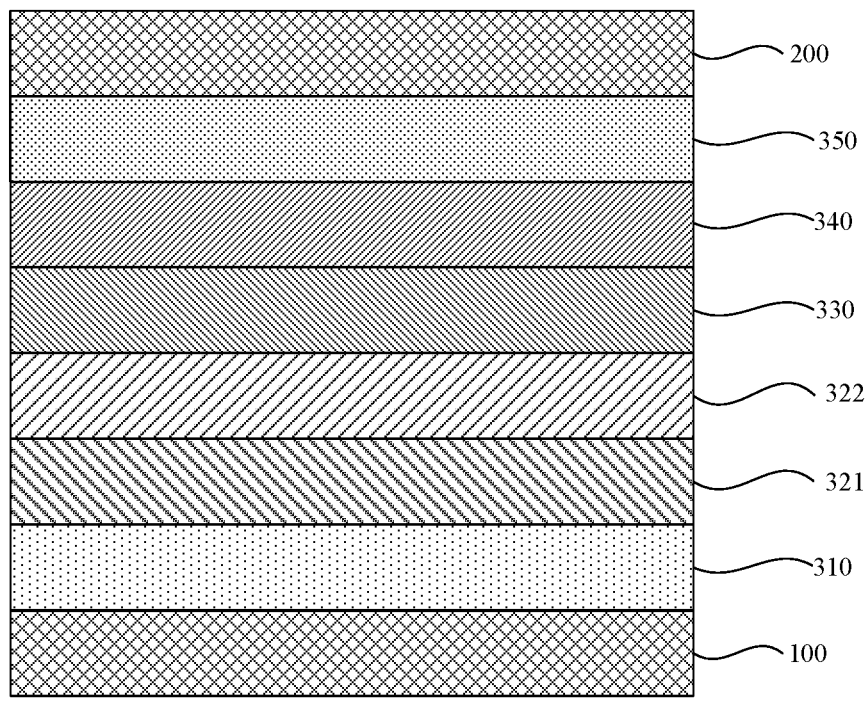
FIG. 1 is a structure diagram showing an organic electroluminescent device in an embodiment of the present disclosure.

In the drawings, reference numerals of the major components are described below:
  100: anode; 200: cathode; 310: hole injection layer; 321: hole transport layer; 322: electron barrier layer; 330: organic light-emitting layer; 340: electron transport layer; 350: electron injection layer; and 400: electronic apparatus.

DETAILED DESCRIPTION

Exemplary examples will be described more comprehensively by reference to the accompanying drawings. However, exemplary examples may be implemented in various forms, and should be not understood to be limited to the examples set forth therein. On the contrary, these examples are provided to make the present disclosure more comprehensive and intact, and the idea of the exemplary examples will be comprehensively conveyed to a person skilled in the art. The described features, structures or properties may be in combination with each other in one or more examples in any suitable way. In the following description, lots of specific details will be provided to give a thorough understanding to the examples of the present disclosure.

In the drawings, for the purpose of clear description, the thickness of regions and layers may be expanded. In the drawings, the same reference numeral denotes the same or similar structure and thus will be not described specifically any more.

In the present disclosure, "-⟩-" and "*-⟩-" have the same meaning, referring to a position binding to other substituents or binding sites.

In the present disclosure, the carbon number of W refers to the number of all the carbon atoms. For example, if W is selected from substituted arylene with 10 carbon atoms, and the total carbon number on the arylene and substituents thereof is 10; if W is 9,9-dimethylfluorenyl, the carbon number on the substituent fluorenyl 15, and the number of ring-forming carbon atoms on the W is 13.

In the present disclosure, when there is no specific definition provided additionally, "hetero" refers that one functional group includes at least one of B, N, O, S, Se, Si or P and other heteroatoms, and the rest are carbon and hydrogen. Unsubstituted alkyl may be a "saturated alkyl group" without any double bond or triple bond.

In the present disclosure, the modes of description used herein, "each . . . is independently", " . . . are each independently selected from"and" . . . is independently selected from" may be exchanged with each other, and should be understood in broad sense, which may mean that in different groups, specific items expressed by a same symbol are not influenced with each other, and also may further refer that in a same group, specific items expressed by a same symbol are not influenced with each other. For example, in the description

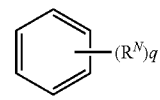

Q-1

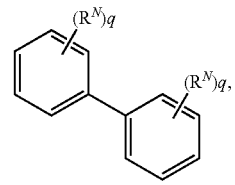

Q-2 each q is independently 0, 1, 2, or 3, and each R" is independently selected from hydrogen, F and Cl", the meaning is as follows: Formula Q-1 indicates that the benzene ring has q substituents R", and each R" may be the same or different, and options in each R" are not influenced with each other; Formula Q-2 indicates that each benzene ring on biphenyl has q substituents R", and the number q of the R" substituents on two benzene rings may be the same or different, and each R" may be the same or different, and options in each R" are not influenced with each other.

In the present disclosure, such a term "substituted or unsubstituted" refers to no substituent or substitution by one or more substituents. The substituent includes, but not limited to, deuterium, halogen (F, Cl, Br), cyano, alkyl, alkenyl, alkynyl, haloalkyl, aryl, heteroaryl, aryloxy, arylthio, silyl, alkylamino, arylamino, cycloalkyl, and heterocyclyl.

In the present disclosure, the term "optional" or "optionally" means that the subsequently described incident or environment may, but need not occur, which includes the occasion where the incident or environment occurs or does not occur. For example, in respect to the technical solution "optionally, two substituents connected to a same atom are connected with each other to form a saturated or unsaturated 5- to 18-membered aliphatic ring or 5- to 18-membered aromatic ring together with the atom to which they are jointly connected", the meaning is as follows: when there are two substituents connected to a same atom, the two substituents may be each independently present, or may be connected with each other, so as to form a saturated or unsaturated 5 to 18 membered aliphatic ring or 5- to 18-membered aromatic ring together with the atom to which they are jointly connected.

In the present disclosure, "alkyl" may include linear alkyl or branched alkyl. Alkyl may have 1 to 20 carbon atoms; in the present disclosure, a range of value, such as, "1 to 20" refers to each integer in a given range; for example, "1 to 20 carbon atoms" refer to alkyl which may contain 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. Alkyl may further be medium-sized alkyl having 1 to 10 carbon atoms. Alkyl may further be lower alkyl having 1 to 6 carbon atoms. In some further embodiments, the alkyl group contains 1 to 4 carbon atoms; and in some further embodiments, the alkyl group contains 1 to 3 carbon atoms. The alkyl group may be optionally substituted by one or more substituents described in the present disclosure. Examples of the alkyl group contain, but not limited to, methyl (Me, —$CH_3$), ethyl (Et, —$CH_2CH_3$), n-propyl (n-Pr, —$CH_2CH_2CH_3$)), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), and the like. Moreover, alkyl may be substituted or unsubstituted.

In the present disclosure, "alkenyl" refers to alkyl including one or more double bonds in a linear or branched hydrocarbon chain. Alkenyl may be substituted or unsubstituted. Alkenyl may have 1 to 20 carbon atoms; when the term is present in the present disclosure, a range of value, such as, "1 to 20" refers to each integer in a given range; for example, "1 to 20 carbon atoms" refer to alkenyl which may contain 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. For example, alkenyl may be ethenyl, butadiene, or 1,3,5-hexatriene.

In the present disclosure, cycloalkyl refers to a cyclic saturated hydrocarbon, containing monocyclic and polycyclic structures. Cycloalkyl may have 3 to 20 carbon atoms; a range of value, such as, "3 to 20" refers to each integer in a given range; for example, "3 to 20 carbon atoms" refer to cycloalkyl which may contain 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. Cycloalkyl may further be a small ring, common ring or large ring having 3 to 20 carbon atoms. Cycloalkyl may be further divided into a monocyclic ring-only one ring, dual rings-two rings or multiple rings-three or above rings. Cycloalkyl may be further divided into a spiro that one carbon atom is shared by two rings, a fused ring that two carbon atoms are shared by two rings, and a bridge ring that two or more carbon atoms are shared by two rings. Furthermore, cycloalkyl may be substituted or unsubstituted. In some embodiments, cycloalkyl is 5- to 10-membered cycloalkyl; in some other embodiments, cycloalkyl is 5- to 8-membered cycloalkyl; for example, examples of cycloalkyl may be, but not limited to, five-membered cycloalkyl, namely, cyclopentyl, six-membered cycloalkyl, namely, cyclohexyl, and ten-membered polycycloalkyl, e.g., adamantyl.

In the present disclosure, aryl refers to an optional functional group derived from an aromatic hydrocarbon ring or a substituent thereof. Aryl may be monocyclic aryl or polycyclic aryl, in other words, aryl may be monocyclic aryl, fused cyclic aryl, two or more monocyclic aryls conjugated via a carbon-carbon bond, monocyclic aryl and fused cyclic aryl conjugated via a carbon-carbon bond, and two or more fused cyclic aryls conjugated via a carbon-carbon bond. That is, two or more aromatic groups conjugated via a carbon-carbon bond may be regarded as aryl of the present disclosure. Aryl is free of B, N, O, S, Se, Si, or P, or other hetero atoms. For example, in the present disclosure, phenyl, biphenyl, terphenylyl and the like are aryl. Examples of aryl may include, but not limited to, phenyl, naphthyl, fluorenyl, anthracyl, phenanthryl, biphenyl, terphenylyl, quarterbiphenyl, quinquephenyl, hexaobiphenyl, benzo[9,10]phenanthryl, pyrenyl, perylenyl, benzofluoranthenyl, chrysenyl, 9,9-dimethylfluorenyl, 9,9-diphenylfluorenyl, spirobifluorenyl, indenyl, and the like.

In this description, the two expressions of "6 to 30 carbon atoms substituted or unsubstituted aryl" and "substituted or unsubstituted aryl with 6 to 30 carbon atoms" have the same meaning, namely, the total carbon number on the aryl and substituents thereof is 6 to 30. In the present disclosure, substituted aryl refers that one or more hydrogen atoms in aryl are substituted by other groups. For example, at least one hydrogen atom is substituted by a D atom, F, Cl, I, CN, hydroxy, amino, branched alkyl, linear alkyl, cycloalkyl, alkoxy, alkylamino, alkylthio, or other groups. It should be understood that the carbon number of the substituted aryl refers to the total carbon number on the aryl and substituents on the aryl. For example, substituted aryl with 18 carbon atoms refers that the total carbon number on the aryl and substituents thereof is 18. For example, 9,9-dimethylfluorenyl is substituted aryl with 15 carbon atoms.

In the present disclosure, heteroaryl may be heteroaryl including at least one of B, O, N, P, Si, Se and S as a hetero atom. Heteroaryl may be monocyclic heteroaryl or polycyclic heteroaryl; in other words, heteroaryl may be a single aromatic ring system, or a multi-aromatic ring system conjugated via a carbon-carbon bond; any aromatic ring system is an aromatic monocyclic ring or an aromatic fused ring, and any aromatic ring system contains the hetero atom. The "heteroaryl" in the present disclosure may include 1, 2, 3, 4, 5, 6, 7, 8, 9 or 10 hetero atoms optionally selected from B, O, N, P, Si, Se and S; and the carbon number may be 3 to 40; in some examples, the carbon number of heteroaryl may be 3 to 30; in some other examples, the carbon number of heteroaryl may be 3 to 20, or 3 to 18, or 3 to 12, or 12 to 18, or 3 to 20. For example, the carbon atom of heteroaryl may be further 3, 5, 6, 7, 8, 9, 10, 11, 12, 13, 14, 15, 16, 18, 20 or 40; of course, the carbon atom may be further other quantity, but will be not enumerated one by one here.

In this description, the two expressions of "3 to 30 carbon atoms substituted or unsubstituted heteroaryl" and "substituted or unsubstituted heteroaryl with 3 to 30 carbon atoms" have the same meaning, namely, the total carbon number on the heteroaryl and substituents thereof is 3-30.

For example, heteroaryl may include, but not limited to, thienyl, furyl, pyrryl, imidazolyl, thiazolyl, oxazolyl, dioxazolyl, triazolyl, pyridyl, dipyridyl, pyrimidyl, triazinyl, acridinyl, pyridazinyl, pyrazinyl, quinolyl, quinazolinyl, quinoxalinyl, phenoxazinyl, phthalazinyl, pyridinopyrimidyl, pyridinopyrazinyl, pyrazino-pyrazinyl, isoquinolyl, indolyl, carbazolyl, benzoxazolyl, benzimidazolyl, benzothiazolyl, benzocarbazolyl, benzothienyl, dibenzothiophenyl, thienothienyl, benzofuryl, phenanthrolinyl, isoxazolyl, thiadiazolyl, benzothiazolyl, phenothiazinyl, silicon-fluorenyl, dibenzofuryl, and N-arylcarbazolyl (e.g., N-phenylcarbazolyl), N-heteroarylcarbazolyl (e.g., N-pyridylcarbazolyl), N-alkylcarbazolyl (e.g., N-methylcarbazolyl), and the like. Thienyl, furyl, phenanthrolinyl, and the like are heteroaryl groups of a single aromatic ring system; N-arylcarbazolyl, and N-heteroarylcarbazolyl are heteroaryl groups of a polycyclic system conjugated via a carbon-carbon bond.

The heteroaryl having 3 to 18 ring-forming carbon atoms in the present disclosure refers to that the carbon number on the heteroaromatic ring in heteroaryl is 3 to 18, and the carbon number in the substituent of heteroaryl is not included. The carbon number on heteroaryl may be 3 to 18, 3 to 12, 3 to 8, but not limited thereto.

In the present disclosure, the understanding to aryl may be applied to arylene; the understanding to heteroaryl may be similarly applied to heteroarylene; the understanding to alkyl may be applied to alkylene, and the understanding to cycloalkyl may be applied to cycloalkylene.

In the present disclosure, the cyclic system formed by n atoms is, namely, an n-membered ring. For example, phenyl is 6-membered aryl. 6- to 10-membered aromatic ring may refer to a benzene ring, an indene ring, a naphthalene and the like.

In the present disclosure, the "ring" contains a saturated ring and unsaturated ring; the saturated ring is namely, cycloalkyl and heterocycloalkyl; the unsaturated ring is namely, cycloalkenyl, heterocycloalkenyl, aryl and heteroaryl.

The delocalized connecting bond in the present disclosure refers to a single bond "*–$\xi$–" or "–$\xi$–" stretching out of the cyclic system, indicating that one end of the connecting bond may be connected to any position in the cyclic system penetrated by the bond, and another end is connected with the rest part of a compound molecule. For example, as shown in the Formula (X) below, the naphthyl denoted by the Formula (X) is connected with other positions of a molecule via two delocalized connecting bonds penetrating dual rings, and the meaning includes any possible connecting mode as shown in Formulas (X-1)-(X-10).

(X)

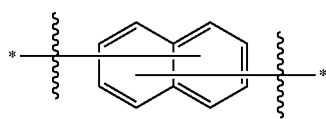

(X-1)

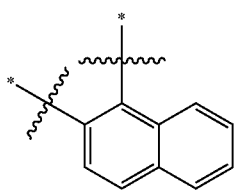

(X-2)

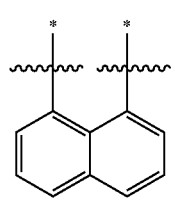

(X-3)

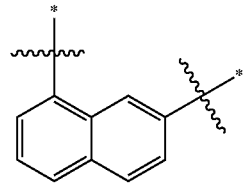

(X-4)

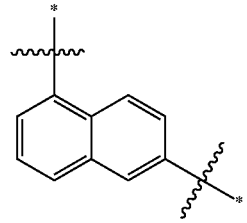

(X-5)

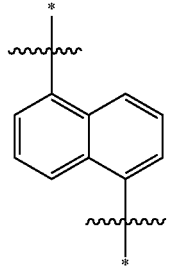

(X-6)

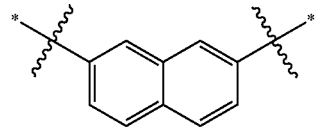

(X-7)

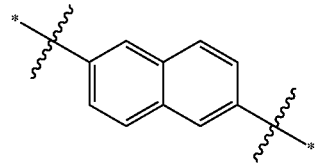

(X-8)

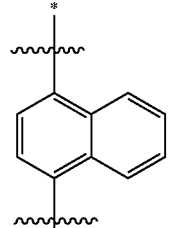

(X-9)

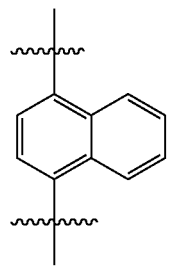

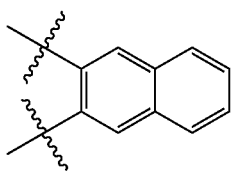
(X-10)

For example, as shown in the Formula (X') below, the phenanthryl denoted by the Formula (X') is connected with other positions of a molecule via a delocalized connecting bond stretching out of the middle part from one side of a benzene ring, and the meaning includes any possible connecting mode as shown in Formulas (X'-1)-(X'-4).

(X')

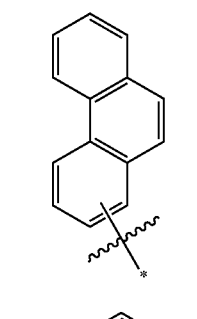
(X'-1)

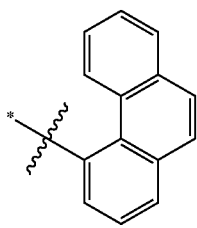
(X'-2)

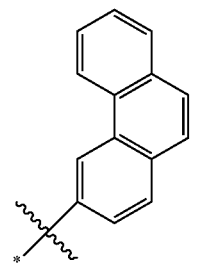
(X'-3)

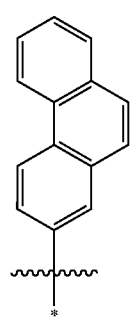

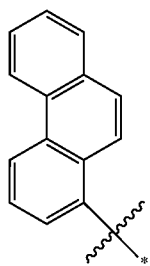
(X'-4)

The delocalized substituent in the present disclosure refers to a substituent connected via a single bond stretching out of the center of a cyclic system, indicating that the substituent may be connected to any possible position in the cyclic system. For example, as shown in the Formula (Y) below, the substituent R denoted by the Formula (Y) is connected with a quinoline ring via a delocalized connecting bond, and the meaning includes any possible connecting mode as shown in Formulas (Y-1)-(Y-7).

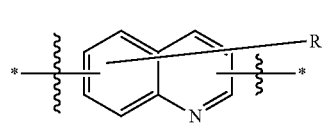
(Y)

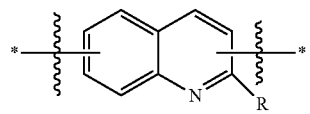
(Y-1)

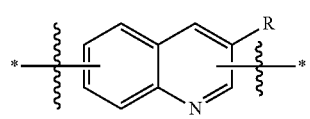
(Y-2)

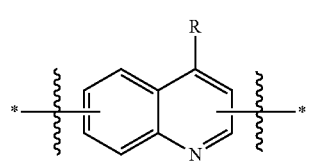
(Y-3)

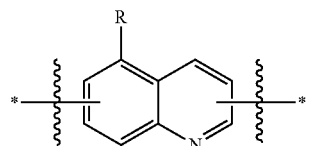
(Y-4)

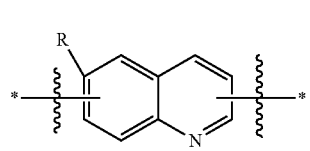
(Y-5)

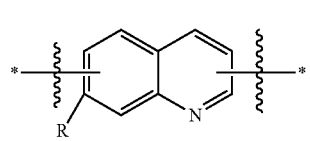
(Y-6)

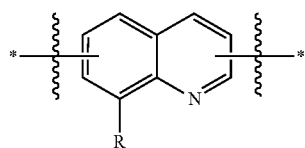
(Y-7)

The present disclosure provides a nitrogen-containing compound, and the nitrogen-containing compound has a structural formula as shown in the chemical formula 1.

Chemical formula 1

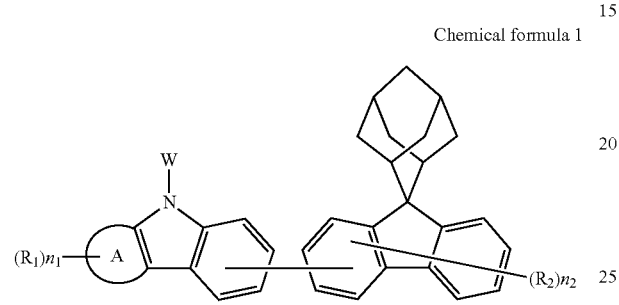

where, the ring A is a benzene ring, a fused aromatic ring having 10 to 14 ring-forming carbon atoms, or a fused heteroaromatic ring having 8 to 12 ring-forming carbon atoms;

$R_1$ and $R_2$ are the same or different from each other, and are each independently selected from deuterium, halogen, cyano, haloalkyl with 1 to 12 carbon atoms, alkyl with 1 to 12 carbon atoms, cycloalkyl with 3 to 12 carbon atoms, alkoxy with 1 to 12 carbon atoms, alkylthio with 1 to 12 carbon atoms, alkylsilyl with 1 to 12 carbon atoms, aryl with 6 to 20 carbon atoms and heteroaryl with 3 to 20 carbon atoms;

$n_1$ is the quantity of the substituent $R_1$, and $n_2$ is the quantity of the substituent $R_2$; when the ring A is a benzene ring, $n_1$ is 0, 1, 2, 3 or 4; when the ring A is a fused aromatic ring or a fused heteroaromatic ring, $n_1$ is 0, 1, 2, 3, 4, 5, 6, 7 or 8; when $n_1$ is greater than 1, any two of $R_1$ are the same or different;

$n_2$ is 0, 1, 2, 3, 4, 5 or 6; when $n_2$ is greater than 1, any two of $R_2$ are the same or different;

W is selected from substituted or unsubstituted aryl with 6 to 40 carbon atoms, substituted or unsubstituted heteroaryl with 3 to 40 carbon atoms.

In the present disclosure, the ring A refers to

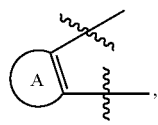

and may be selected from a benzene ring, fused aromatic ring, fused heteroaryl, for example, may be selected from a naphthalene ring, an anthracene ring, a phenanthrene ring, a quinoline ring and the like.

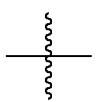

denotes a chemical bond. For example, in the compound the ring A is a naphthalene ring, the substituent $R_1$ on the ring A is hydrogen. It should be understood that the ring A includes at least one benzene ring structure, such that the nitrogen-containing compound of the present disclosure includes at least one carbazole structure.

The carbazole structure may be conjugated with a fluorenyl group to form a large conjugated plane. The large-plane conjugated structure as the core of the nitrogen-containing compound has stronger rigidity, such that the nitrogen-containing compound of the present disclosure has a high first triplet energy level. Therefore, the nitrogen-containing compound of the present disclosure is suitable for as a host material of a luminescent layer in an organic electroluminescent device. Adamantyl and fluorenyl are connected by spiro, which may greatly increase the electron cloud density of the large-plane conjugated structure by hyperconjugation effect, thus enhancing the hole mobility of the nitrogen-containing compound, being conducive to promoting the transport balance between holes and electrons in an emitting layer, and improving the efficiency performance of the organic electroluminescent device. Moreover, the promotion of the hole transport performance of the nitrogen-containing compound may improve the recombination rate of holes and electrons in an organic light-emitting layer, reduce or avoid that electrons transport to the hole transport layer after passing through the organic light-emitting layer, thereby effectively protecting the material of the hole transport layer from the impact of electrons and prolonging the lifetime of the organic electroluminescent device. Furthermore, adamantyl connected on fluorenyl by spiro has a large space volume and stronger rigidity, and thus may reduce the interaction force between the large-plane conjugated structure, decrease R-r stacking between molecules, and adjust the degree of intermolecular stacking, such that the nitrogen-containing compound may have a more stable amorphous state during film formation to improve the film-forming property of the nitrogen-containing compound, thus further prolonging the lifetime of the organic electroluminescent device.

In the present disclosure, the carbon number of $R_1$, $R_2$ and W refers to the number of all the carbon atoms. For example, if W is selected from $C_{10}$ aryl, and the total carbon number on the aryl and substituents thereof is 10. For another example, if W is p-tert-butylphenyl, W is substituted phenyl with 10 carbon atoms, and the number of ring-forming carbon atoms on the W is 6.

In the present disclosure, when there is no specific definition provided additionally, "hetero" refers that one functional group includes at least one of B, N, O, S, Se, Si or P and other heteroatoms, and the rest are carbon and hydrogen. Unsubstituted alkyl may be a "saturated alkyl group" without any double bond or triple bond.

It should be understood that the carbon number of the substituted aryl refers to the total carbon number on the aryl and substituents on the aryl. For example, substituted aryl with 18 carbon atoms refers that the total carbon number on the aryl and substituents thereof is 18. For example, 9,9-dimethylfluorenyl is substituted aryl with 15 carbon atoms.

In some embodiments, substituents in the W are the same or different from each other, and are each independently selected from the group consisting of deuterium; halogen; cyano; alkyl with 1 to 12 carbon atoms; haloalkyl with 1 to 12 carbon atoms; cycloalkyl with 3 to 10 carbon atoms; heterocycloalkyl with 2 to 10 carbon atoms; aralkyl with 7 to 10 carbon atoms; heteroaralkyl with 4 to 10 carbon atoms; aryl with 6 to 30 carbon atoms optionally substituted by 0, 1, 2 or 3 substituents selected from deuterium, F, Cl, Br, cyano, alkyl, aryl and heteroaryl; heteroaryl with 3 to 30 carbon atoms optionally substituted by 0, 1, 2 or 3 substituents selected from deuterium, F, Cl, Br, cyano, alkyl, aryl and heteroaryl; alkoxy with 1 to 12 carbon atoms; alkylthio with 1 to 12 carbon atoms; trialkylsilyl with 3 to 12 carbon atoms; arylsilyl with 6 to 18 carbon atoms; aryloxy with 6 to 20 carbon atoms and arylthio with 6 to 20 carbon atoms;

in the W, when the same atom has two substituents, optionally, the two substituents connected to the same atom are connected with each other to form a saturated or unsaturated 5- to 18-membered aliphatic ring or 5- to 18-membered aromatic ring together with the atom to which they are jointly connected. In some embodiments, the nitrogen-containing compound of the present disclosure has a structural formula as shown in any one of the chemical formulas (f-1) to

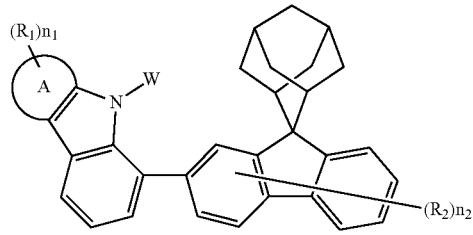

(f-1)

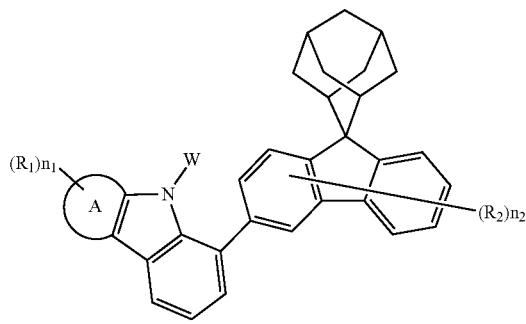

(f-2)

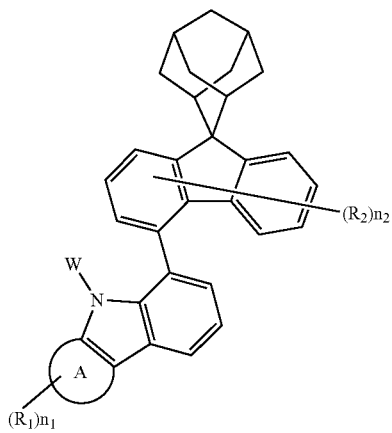

(f-3)

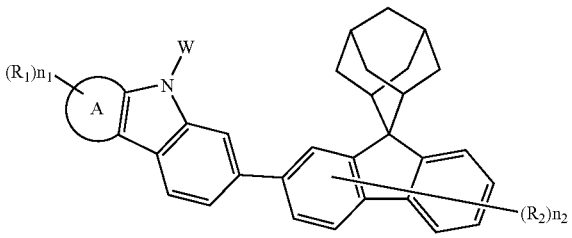

(f-4)

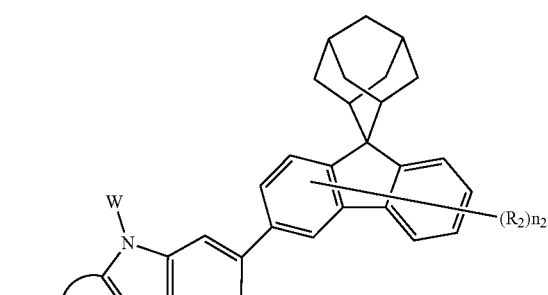

(f-5)

(f-6)
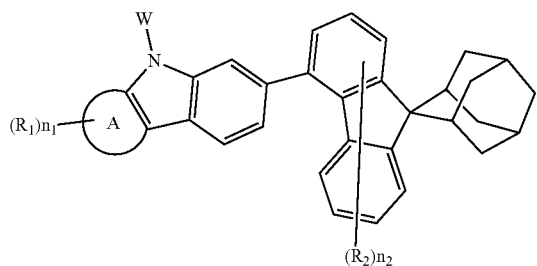
(f-7)
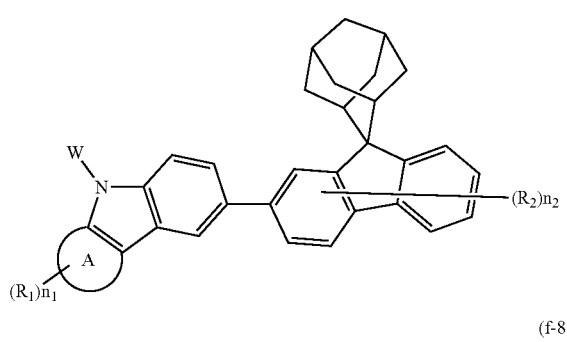
(f-8)
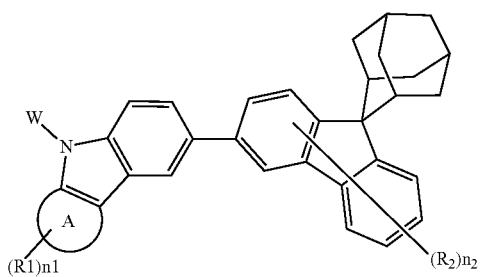
(f-9)
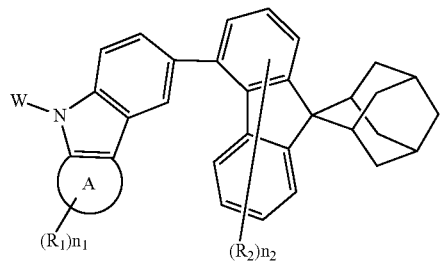
(f-10)
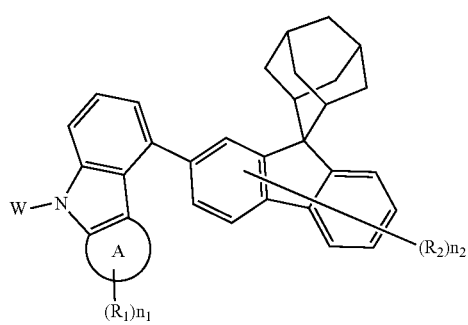
(f-11)
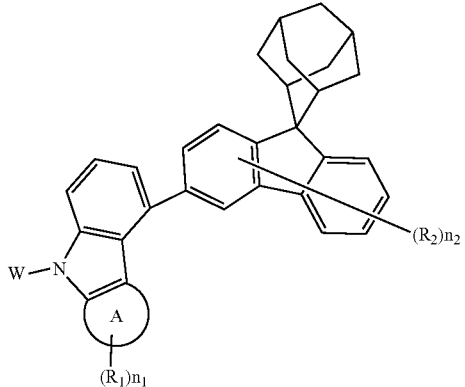
(f-12)
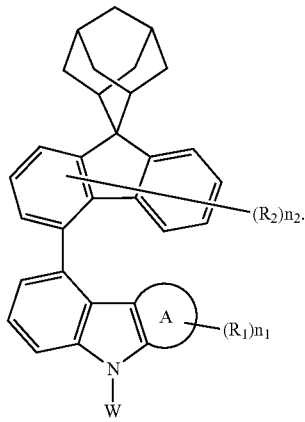
In some embodiments, the ring A in the structural formula 1 of the nitrogen-containing compound of the present disclosure is a benzene ring or naphthalene ring.
Optionally, the nitrogen-containing compound of the present disclosure has a structural formula as shown in any one of chemical formulas (U-2) to (U-15):
U-2
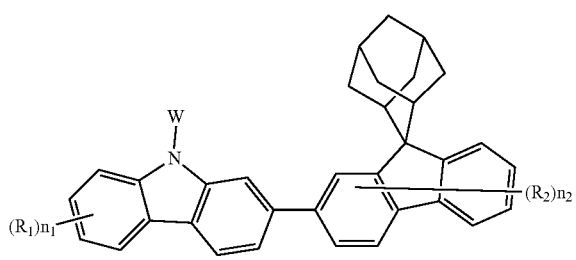
U-3
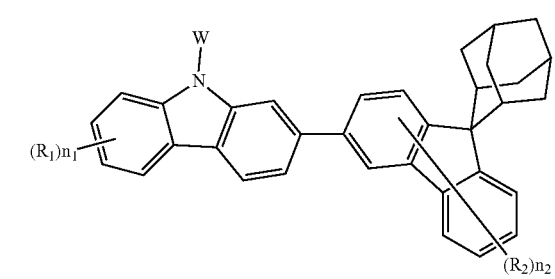

U-4
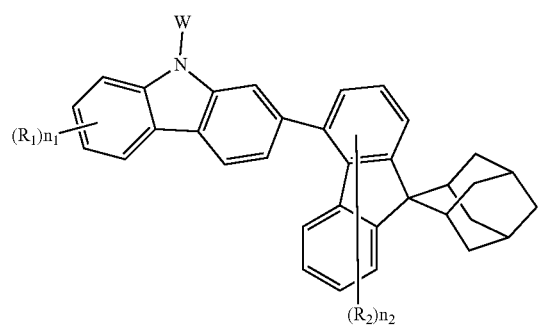
U-5
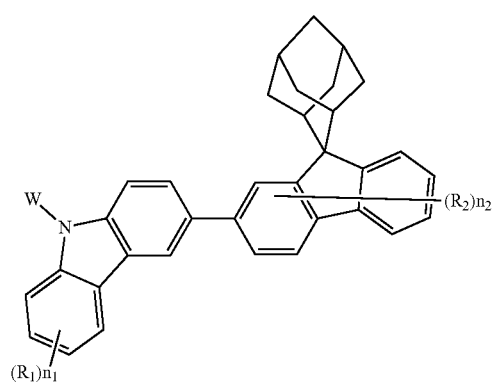
U-6
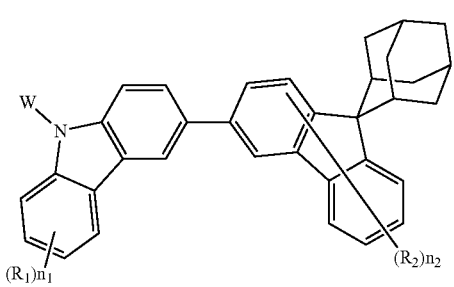
U-7
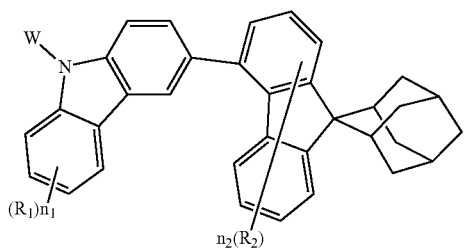
U-8
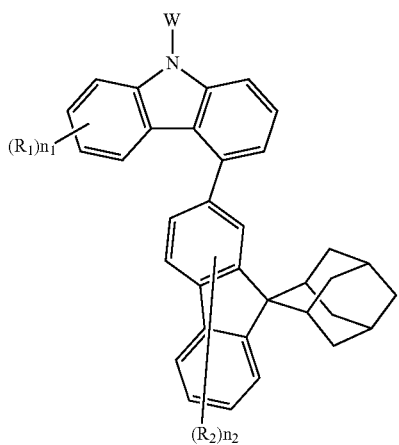
U-9
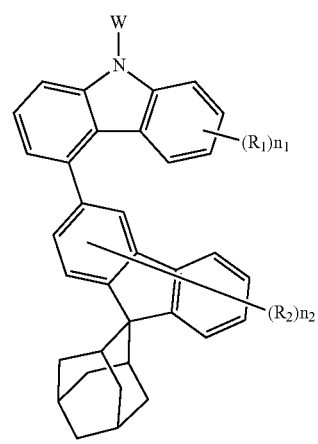
U-10
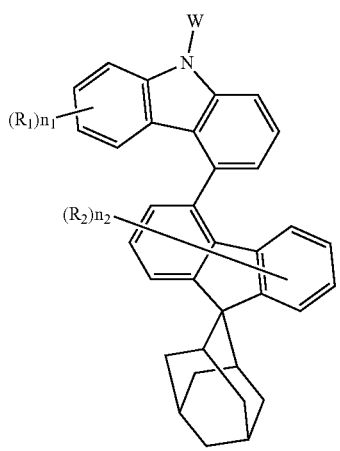

-continued

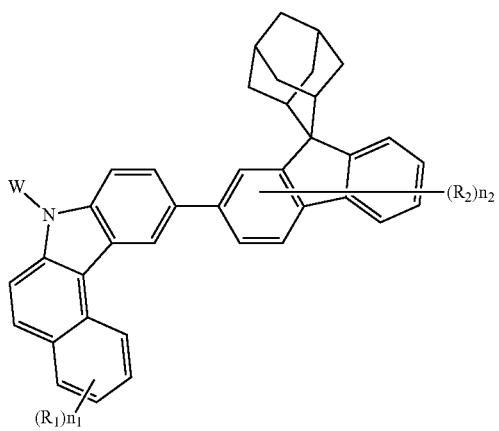
U-11

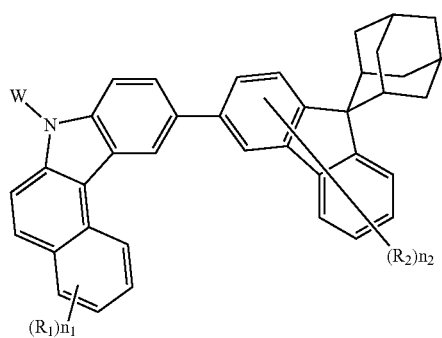
U-12

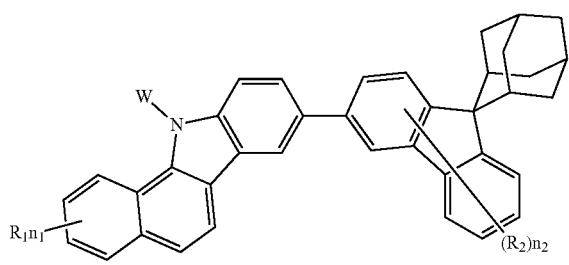
U-13

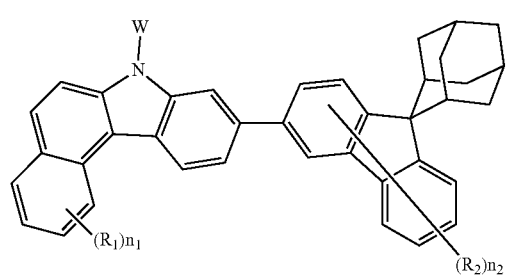
U-14

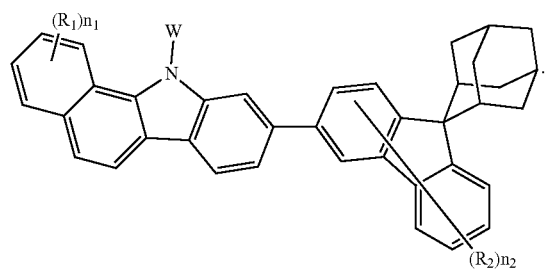
U-15

When the nitrogen-containing compound of the present disclosure is selected from the structures as shown in the chemical formulas (U-11) to (U-15), the ring A in the nitrogen-containing compound is a fused aromatic ring structure. Therefore, the nitrogen-containing compound has a larger-plane conjugated structure, stronger rigidity, and higher electron cloud density, such that the nitrogen-containing compound has a stronger hole transport capability, which thus may improve the recombination rate of holes and electrons in an organic light-emitting layer, reduce or avoid that electrons transport to the hole transport layer after passing through the organic light-emitting layer, thereby effectively protecting the material of the hole transport layer from the impact of electrons and prolonging the lifetime of the organic electroluminescent device.

In some detailed examples, $R_1$ and $R_2$ are each independently selected from hydrogen, deuterium, F, Cl, Br, cyano, methyl, isopropyl, ethylisopropyl, cyclopropyl, tert-butyl, ethyoxyl, trifluoromethyl, trimethylsilyl, phenyl, pyridyl, pyrimidyl, triazinyl and the like.

In some detailed embodiments of the present disclosure, W is

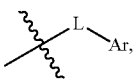

where, L is each independently selected from a single bond, substituted or unsubstituted arylene with 6 to 20 carbon atoms, substituted or unsubstituted heteroarylene with 3 to 20 carbon atoms; Ar is selected from substituted or unsubstituted aryl with 6 to 30 carbon atoms, substituted or unsubstituted heteroaryl with 3 to 30 carbon atoms; substituents in the $Ar_1$ and L are the same or different from each other, and are each independently selected from deuterium, F, Cl, Br, cyano, aryl with 6 to 20 carbon atoms, heteroaryl with 3 to 20 carbon atoms, alkylsilyl with 3 to 18 carbon atoms, arylsilyl with 6 to 18 carbon atoms, alkyl with 1 to 12 carbon atoms, alkoxy with 1 to 12 carbon atoms, haloalkyl with 1 to 12 carbon atoms, alkenyl with 2 to 12 carbon atoms, cycloalkyl with 3 to 10 carbon atoms, heterocycloalkyl with 2 to 12 carbon atoms, alkylamino with 1 to 10 carbon atoms, alkylthio with 1 to 10 carbon atoms, aryloxy with 6 to 18 carbon atoms, and arylthio with 6 to 18 carbon atoms.

In some further embodiments, W is

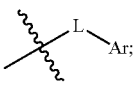

where, L is each independently selected from a single bond, substituted or unsubstituted arylene with 6 to 20 carbon atoms, substituted or unsubstituted heteroarylene with 3 to 20 carbon atoms; Ar is selected from substituted or unsubstituted aryl with 6 to 30 carbon atoms, and substituted or unsubstituted heteroaryl with 3 to 30 carbon atoms;

The substituents in the Ar and L are the same or different from each other, and are each independently selected from deuterium, F, Cl, Br, cyano, aryl with 6 to 15 carbon atoms optionally substituted by 0, 1, 2, or 3 substituents selected from deuterium, F, Cl, Br and cyano; heteroaryl with 3 to 12 carbon atoms optionally substituted by 0, 1, 2, or 3 substituents selected from deuterium, F, Cl, Br and cyano;

trialkylsilyl with 3 to 12 carbon atoms, arylsilyl with 8 to 18 carbon atoms, alkyl with 1 to 12 carbon atoms, alkoxy with 1 to 12 carbon atoms, haloalkyl with 1 to 12 carbon atoms, alkenyl with 2 to 12 carbon atoms, cycloalkyl with 3 to 10 carbon atoms, heterocycloalkyl with 2 to 12 carbon atoms, alkylthio with 1 to 10 carbon atoms, aryloxy with 6 to 12 carbon atoms, and arylthio with 6 to 12 carbon atoms; when the same atom in L and Ar has two substituents, optionally, the two substituents connected to the same atom are connected with each other to form a saturated or unsaturated 5- to 13-membered aliphatic ring or 5- to 13-membered aromatic ring together with the atom to which they are jointly connected.

Optionally, L is selected from a single bond or the group consisting of the following substituents:

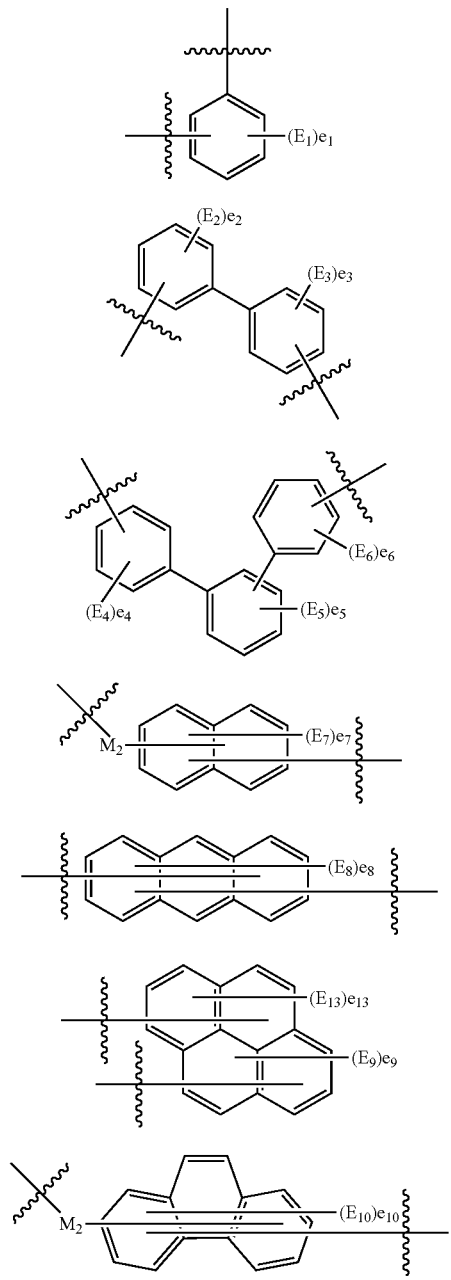

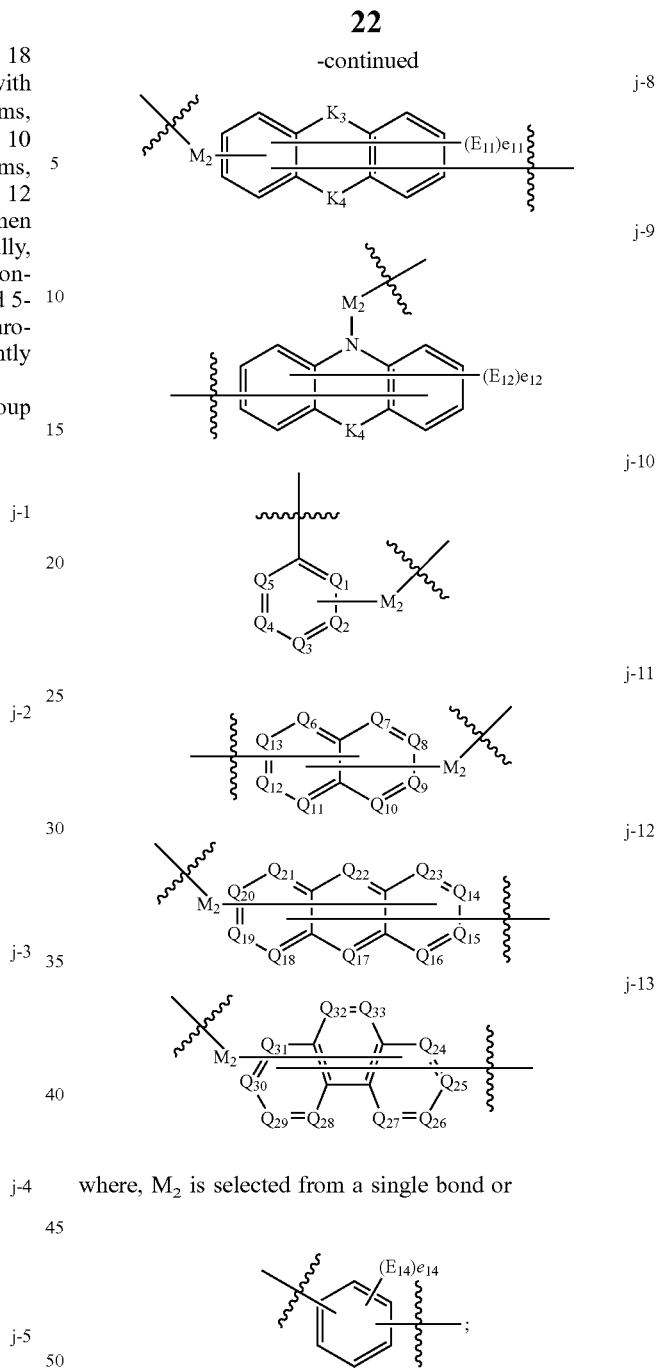

where, $M_2$ is selected from a single bond or $Q_1$ to $Q_5$ are each independently selected from N or $C(J_1)$, and at least one of $Q_1$ to $Q_5$ is selected from N; when two or more of $Q_1$ to $Q_5$ are selected from $C(J_1)$, any two of $J_1$ are the same or different;

$Q_6$ to $Q_{13}$ are each independently selected from N or $C(J_2)$, and at least one of $Q_6$ to $Q_{13}$ is selected from N; when two or more of $Q_6$ to $Q_{13}$ are selected from $C(J_2)$, any two of $J_2$ are the same or different;

$Q_{14}$ to $Q_{23}$ are each independently selected from N or $C(J_3)$, and at least one of $Q_{14}$ to $Q_{23}$ is selected from N; when two or more of $Q_{14}$ to $Q_{23}$ are selected from $C(J_3)$, any two of $J_3$ are the same or different;

$Q_{24}$ to $Q_{33}$ are each independently selected from N or $C(J_4)$, and at least one of $Q_{24}$-$Q_{33}$ is selected from N; when two or more of $Q_{24}$ to $Q_{33}$ are selected from $C(J_4)$, any two of $J_4$ are the same or different;

$E_1$ to $E_{14}$ and $J_1$ to $J_4$ are each independently selected from: hydrogen, deuterium, F, Cl, Br, cyano, heteroaryl with 3 to 20 carbon atoms, aryl with 6 to 20 carbon atoms, trialkylsilyl with 3 to 12 carbon atoms, arylsilyl with 8 to 12 carbon atoms, alkyl with 1 to 10 carbon atoms, haloalkyl with 1 to 10 carbon atoms, alkenyl with 2 to 6 carbon atoms, alkynyl with 2 to 6 carbon atoms, cycloalkyl with 3 to 10 carbon atoms, heterocycloalkyl with 2 to 10 carbon atoms, alkoxy with 1 to 10 carbon atoms, alkylamino with 1 to 10 carbon atoms, arylthio with 1 to 10 carbon atoms, aryloxy with 6 to 18 carbon atoms, arylamino with 6 to 18 carbon atoms, and arylthio with 6 to 18 carbon atoms;

$e_r$ is the number of substituents $E_r$, r is any integer of 1 to 14; when r is selected from 1, 2, 3, 4, 5, 6, 9, 13 or 14, $e_r$ is selected from 1, 2, 3, or 4; when r is selected from 7 or 11, $e_r$ is selected from 1, 2, 3, 4, 5, or 6; when r is 12, $e_r$ is selected from 1, 2, 3, 4, 5, 6, or 7; when r is selected from 8 or 10, $e_r$ is selected from 1, 2, 3, 4, 5, 6, 7, or 8; when $e_r$ is greater than 1, any two of $E_r$ are the same or different;

$K_3$ is selected from O, S, Se, $N(E_{15})$, $C(E_{16}E_{17})$, and $Si(E_{16}E_{17})$, wherein, $E_{15}$, $E_{16}$ and $E_{17}$ are each independently selected from: aryl with 6 to 20 carbon atoms, alkyl with 1 to 10 carbon atoms, alkenyl with 2 to 6 carbon atoms, cycloalkyl with 3 to 10 carbon atoms, and heterocycloalkyl with 2 to 10 carbon atoms; or $E_{16}$ and $E_{17}$ are connected with each other to form a saturated or unsaturated 5- to 13-membered ring together with the atom to which they are jointly connected;

$K_4$ is selected from O, S, Se, $N(E_{15})$, $C(E_{19}E_{20})$, and $Si(E_{19}E_{20})$, wherein, $E_{15}$, $E_{19}$ and $E_{20}$ are each independently selected from: aryl with 6 to 20 carbon atoms, alkyl with 1 to 10 carbon atoms, alkenyl with 2 to 6 carbon atoms, cycloalkyl with 3 to 10 carbon atoms, and heterocycloalkyl with 2 to 10 carbon atoms; or $E_{19}$ and $E_{20}$ are connected with each other to form a saturated or unsaturated 5- to 13-membered ring together with the atom to which they are jointly connected.

In the present disclosure, L may be

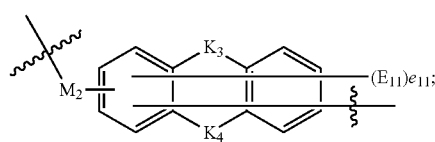

when $K_4$ is a single bond, and $K_3$ is $C(E_{16}E_{17})$, the meaning of $E_{16}$ and $E_{17}$ ring formation refers that a spiro may be formed on a 9 site of fluorenyl, for example, L may be

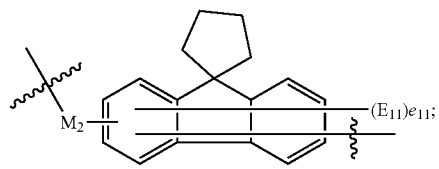

of course, the carbon number on the ring formed by linking $E_{16}$ and $E_{17}$ may be further other values, but will be not enumerated one by one here.

Optionally, $E_1$ to $E_{14}$ and $J_1$ to $J_4$ in the above structures are each independently selected from: hydrogen, deuterium, F, Cl, Br, cyano, heteroaryl with 3 to 12 carbon atoms, aryl with 6 to 15 carbon atoms, trialkylsilyl with 3 to 12 carbon atoms, arylsilyl with 8 to 12 carbon atoms, alkyl with 1 to 10 carbon atoms, haloalkyl with 1 to 10 carbon atoms, alkenyl with 2 to 6 carbon atoms, alkynyl with 2 to 6 carbon atoms, cycloalkyl with 3 to 10 carbon atoms, heterocycloalkyl with 2 to 10 carbon atoms, alkoxy with 1 to 10 carbon atoms, alkylamino with 1 to 10 carbon atoms, arylthio with 1 to 10 carbon atoms, aryloxy with 6 to 18 carbon atoms, arylamino with 6 to 18 carbon atoms, and arylthio with 6 to 18 carbon atoms.

Optionally, only one of $Q_1$ to $Q_5$ is selected from N.

Preferably, only one of $Q_6$ to $Q_{13}$ is selected from N.

Preferably, only one of $Q_{14}$ to $Q_{23}$ is selected from N.

Preferably, only one of $Q_{24}$ to $Q_{33}$ is selected from N.

Optionally, the L is selected from a single bond or an unsubstituted $L_1$, or a substituted $L_1$, where the unsubstituted $L_1$ is selected from the group consisting of the following groups:

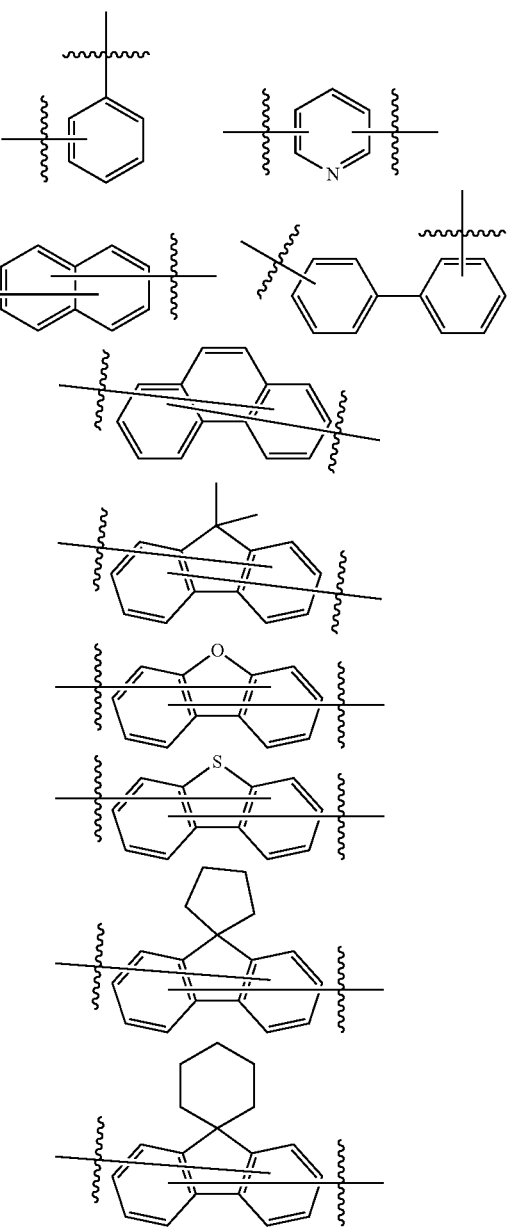

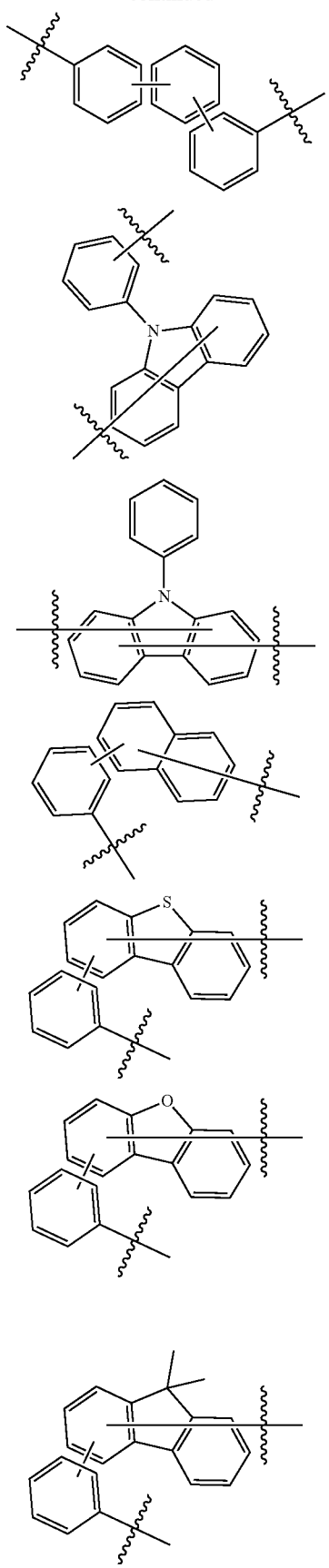

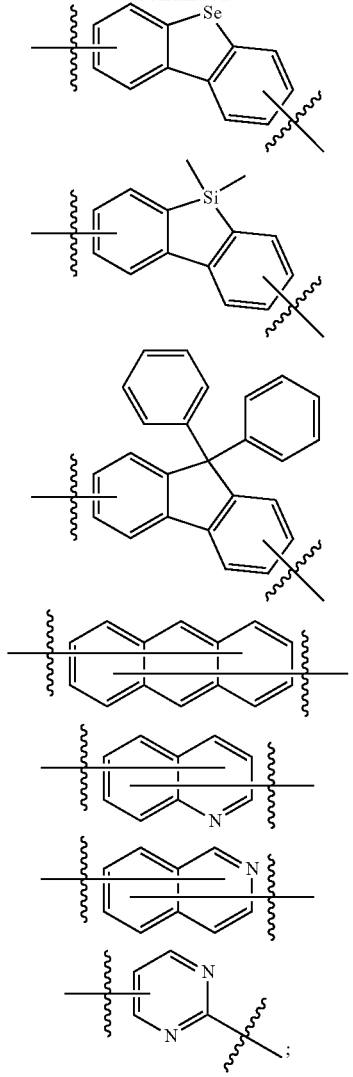

the substituted $L_1$ is a group formed by substituting the unsubstituted $L_1$ by one or more of substituents selected from deuterium, F, Cl, Br, cyano, alkyl with 1 to 6 carbon atoms, cycloalkyl with 6 to 10 carbon atoms and aryl with 6 to 12 carbon atoms; and when the substituted $L_1$ has a plurality of substituents, any two of substituents are the same or different.

In some examples of the present disclosure, the L is selected from one of a single bond, substituted or unsubstituted phenylene, substituted or unsubstituted biphenylene, substituted or unsubstituted terphenylene, substituted or unsubstituted naphthylene, substituted or unsubstituted 9,9-dimethylfluorenylidene, substituted or unsubstituted 9,9-dimethyl-9H-9-silafluorenylidene, substituted or unsubstituted dibenzofurylene, substituted or unsubstituted dibenzothiophenylene, substituted or unsubstituted quinolylene, substituted or unsubstituted isoquinolylene, substituted or unsubstituted carbazolylene, substituted or unsubstituted phenanthrylene, substituted or unsubstituted anthrylene, substituted or unsubstituted pyridylidene, substituted or unsubstituted spirobifluorenylidene, spiro[cyclopentane-1,9'-fluorenylidene], and spiro[cyclohexane-1,9'-fluorenylidene]; or a bivalent group formed by linking two or three of the above bivalent groups via a single bond;

substituents in L are the same or different from each other, and are each independently selected from the group consisting of deuterium, F, Cl, cyano, methyl, ethyl, isopropyl, n-propyl, tert-butyl, methoxy, ethyoxyl, trifluoromethyl, trimethylsilyl, phenyl, cyano-substituted phenyl, fluoro-substituted phenyl, naphthyl, cyclopentyl, and cyclohexyl.

In some examples of the present disclosure, Ar may be selected from aryl or electron-rich heteroaryl; hetero atoms on the electron-rich heteroaryl may enhance the electron cloud density of a conjugated system of heteroaryl generally, for example, lone pair electrons on hetero atoms may participate in the conjugated system to increase the electron cloud density of the conjugated system of heteroaryl. For example, the electron-rich heteroaryl may include, but not limited to, carbazolyl, dibenzofuryl, dibenzothiazolyl, furyl, pyrryl, and the like. Since aryl and electron-rich heteroaryl may effectively enhance the electron cloud density of the nitrogen-containing compound, and may adjust the HOMO energy level of the nitrogen-containing compound, the nitrogen-containing compound will have better hole transport capability. In this way, the nitrogen-containing compound may serve as a host material for a hole-type organic light-emitting layer, and matched with a host material of an electron-type organic light-emitting layer used for transporting electrons to jointly form a host material of the organic light-emitting layer.

In some detailed embodiments of the present disclosure, Ar is selected from a substituent as shown in chemical formulas i-1 to i-11:

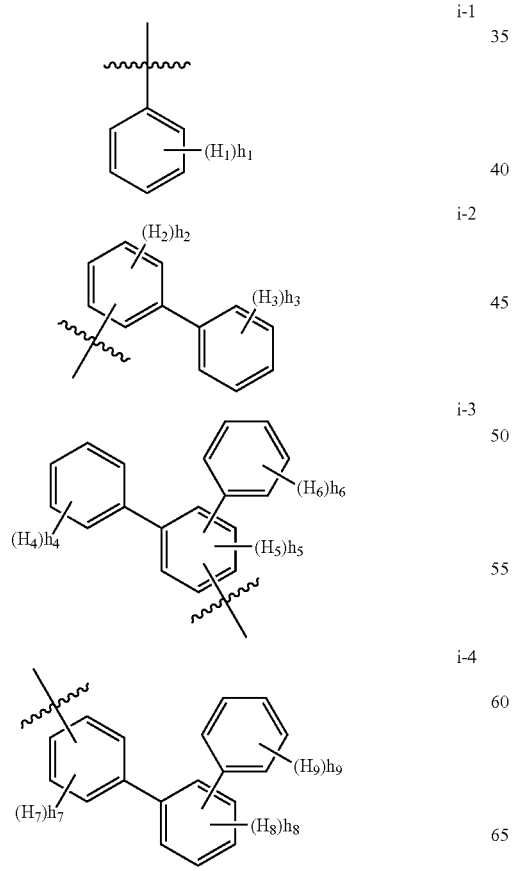

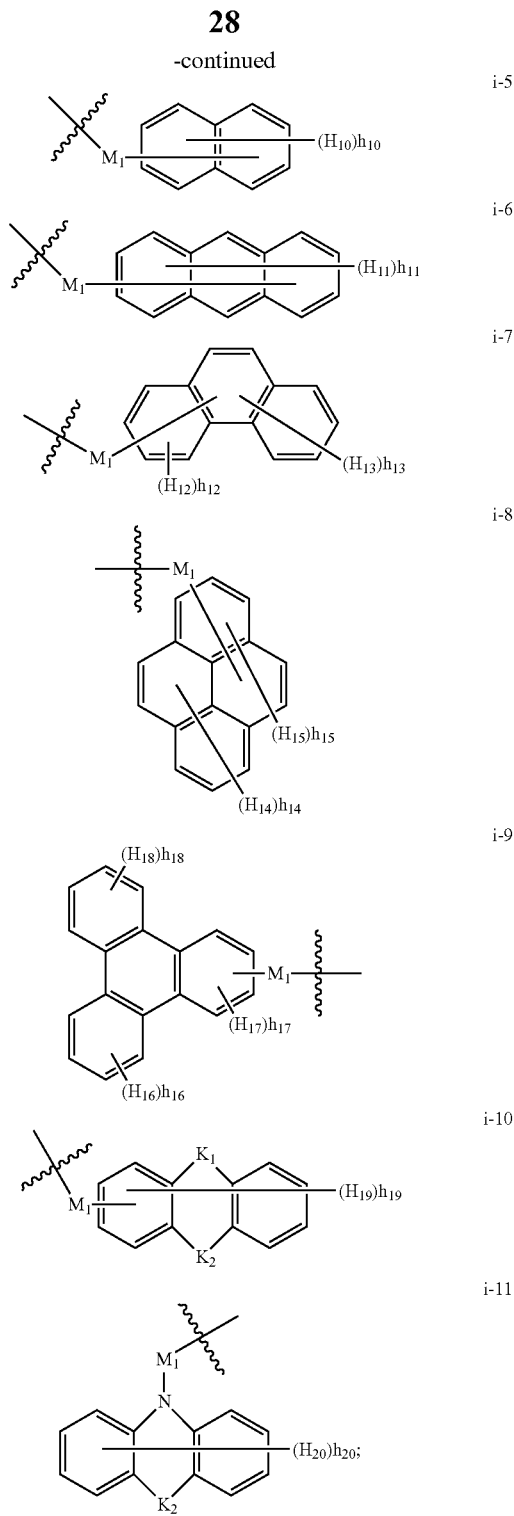

wherein, $M_1$ is selected from a single bond or

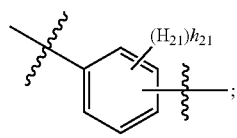

$H_1$ to $H_{21}$ are each independently selected from: hydrogen, deuterium, F, Cl, Br, cyano, alkoxy with 1 to 10 carbon atoms, alkylamino with 1 to 10 carbon atoms, alkylthio with 1 to 10 carbon atoms, trialkylsilyl with 3 to 12 carbon atoms, arylsilyl with 8 to 12 carbon atoms, alkyl with 1 to 10 carbon atoms, cycloalkyl with 3 to 10 carbon atoms, and heterocycloalkyl with 2 to 10 carbon atoms; any one of $H_4$ to $H_{20}$ may be further independently selected from aryl with 6 to 20 carbon atoms;

$h_k$ is the number of substituent $H_k$, k is any integer of 1 to 21; when k is selected from 5 or 17, $h_k$ is selected from 1, 2, or 3; when k is selected from 2, 7, 8, 12, 15, 16, 18 or 21, $h_k$ is selected from 1, 2, 3, or 4; when k is selected from 1, 3, 4, 6, 9 or 14, $h_k$ is selected from 1, 2, 3, 4, or 5; when k is 13, $h_k$ is selected from 1, 2, 3, 4, 5, or 6; when k is selected from 10 or 19, $h_k$ is selected from 1, 2, 3, 4, 5, 6 or 7; when k is selected from 20, $h_k$ is selected from 1, 2, 3, 4, 5, 6, 7 or 8; when k is 11, $h_k$ is selected from 1, 2, 3, 4, 5, 6, 7, 8 or 9; when $h_k$ is greater than 1, any two of $H_k$ are the same or different;

$K_1$ is selected from O, S, Se, $N(H_{22})$, $C(H_{23}H_{24})$, and $Si(H_{23}H_{24})$, wherein, $H_{22}$, $H_{23}$ and $H_{24}$ are each independently selected from: aryl with 6 to 20 carbon atoms, alkyl with 1 to 10 carbon atoms, alkenyl with 2 to 6 carbon atoms, cycloalkyl with 3 to 10 carbon atoms, and heterocycloalkyl with 2 to 10 carbon atoms; or $H_{23}$ and $H_{24}$ are connected with each other to form a saturated or unsaturated 5- to 13-membered ring together with the atom to which they are jointly connected;

$K_2$ is selected from O, S, Se, $N(H_{25})$, $C(H_{26}H_{27})$, and $Si(H_{26}H_{27})$, wherein, $H_{25}$, $H_{26}$ and $H_{27}$ are each independently selected from: aryl with 6 to 20 carbon atoms, alkyl with 1 to 10 carbon atoms, alkenyl with 2 to 6 carbon atoms, cycloalkyl with 3 to 10 carbon atoms, and heterocycloalkyl with 2 to 10 carbon atoms; or $H_{26}$ and $H_{27}$ are connected with each other to form a saturated or unsaturated 5- to 13-membered ring together with the atom to which they are jointly connected. Here, the understanding to the technical solution "$H_{26}$ and $H_{27}$ optionally form a ring" is consistent with that in other technical solutions (when $E_{16}$ and $E_{17}$ are connected to form a ring).

Optionally, Ar is selected from an unsubstituted $Ar_1$, or a substituted $Ar_1$, where the unsubstituted $Ar_1$ is selected from the group consisting of the following groups:

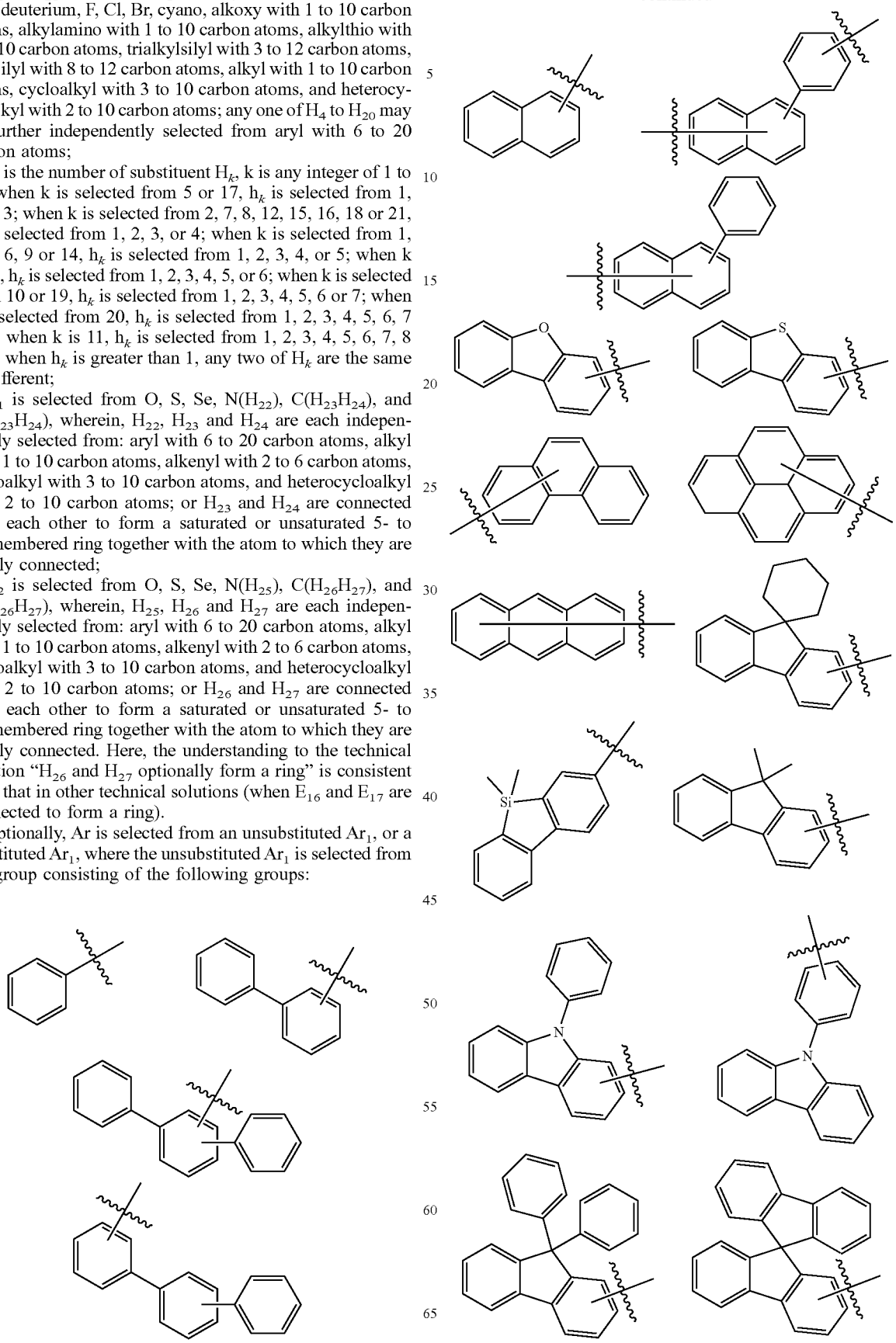

-continued

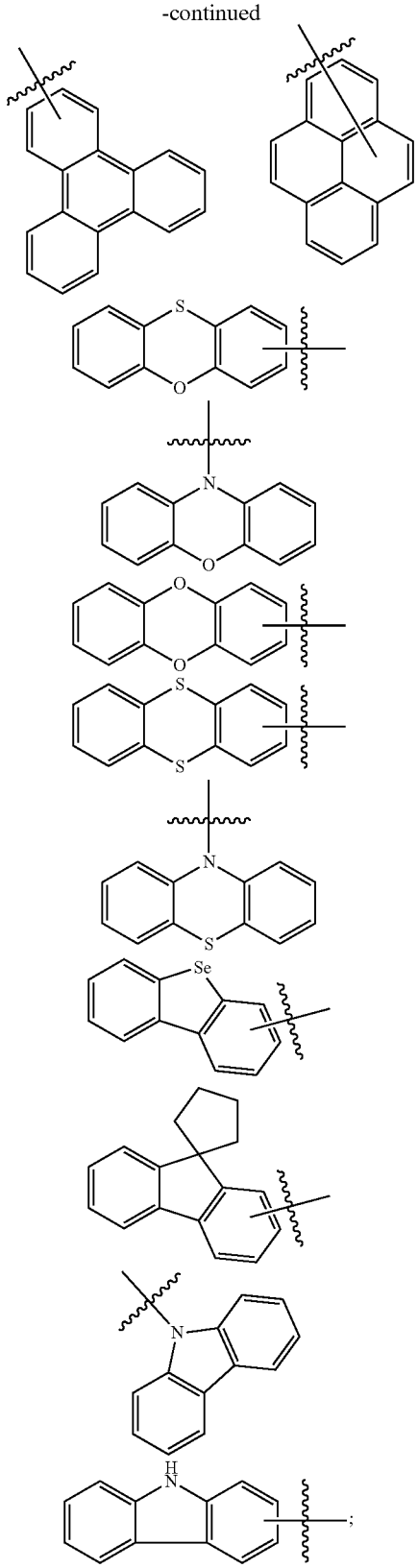

wherein, the substituted $Ar_1$ is a group formed by substituting the unsubstituted $Ar_1$ by one or more of substituents selected from deuterium, F, Cl, Br, cyano, alkyl with 1 to 6 carbon atom, cycloalkyl with 3 to 10 carbon atom, aryl with 6 to 20 carbon atom, alkoxy with 1 to 4 carbon atom, haloalkyl with 1 to 4 carbon atom, and alkylsilyl with 3 to 9 carbon atom; and when the substituted $Ar_1$ has a plurality of substituents, any two of substituents are the same or different.

Further, the above substituted $Ar_1$ is substituted by 1, 2, 3, 4 or 5 substituents independently selected from deuterium, F, Cl, cyano, trifluoromethyl, trimethylsilyl, methyl, ethyl, isopropyl, tert-butyl, methoxy, ethyoxyl, isopropoxy, trifluoromethyl, cyclopentyl, cyclohexyl, phenyl, naphthyl, pyridyl, pyrimidyl, quinolyl, and isoquinolyl; each substituent is the same or different.

In some examples, Ar is selected from one of substituted or unsubstituted phenyl, substituted or unsubstituted biphenyl, substituted or unsubstituted triphenyl, substituted or unsubstituted naphthyl, substituted or unsubstituted 9,9-dimethylfluorenyl, substituted or unsubstituted 9,9-dimethyl-9H-9-silafluorenyl, substituted or unsubstituted dibenzofuryl, substituted or unsubstituted dibenzothiophenyl, substituted or unsubstituted carbazolyl, substituted or unsubstituted phenanthryl, substituted or unsubstituted anthryl, substituted or unsubstituted spirobifluorenyl, spiro[cyclopentane-1,9'-fluorenylidene], spiro[cyclohexane-1,9'-fluorenylidene], pyrenyl, perylenyl phenoxytheophyllinyl, phenoxazinyl, phenothiazinyl, dibenzodioxinyl, and thianthrenyl; or a group formed by linking two or three of the above groups via a single bond; the Ar is optionally substituted by 0, 1, 2, 3, 4, or 5 substituents independently selected from deuterium, F, Cl, cyano, methyl, ethyl, isopropyl, n-propyl, tert-butyl, methoxy, ethyoxyl, trifluoromethyl, trimethylsilyl, phenyl, cyano-substituted phenyl, fluoro-substituted phenyl, naphthyl, cyclopentyl, and cyclohexyl.

In some more detailed embodiments, Ar is selected from the group consisting of the following substituents:

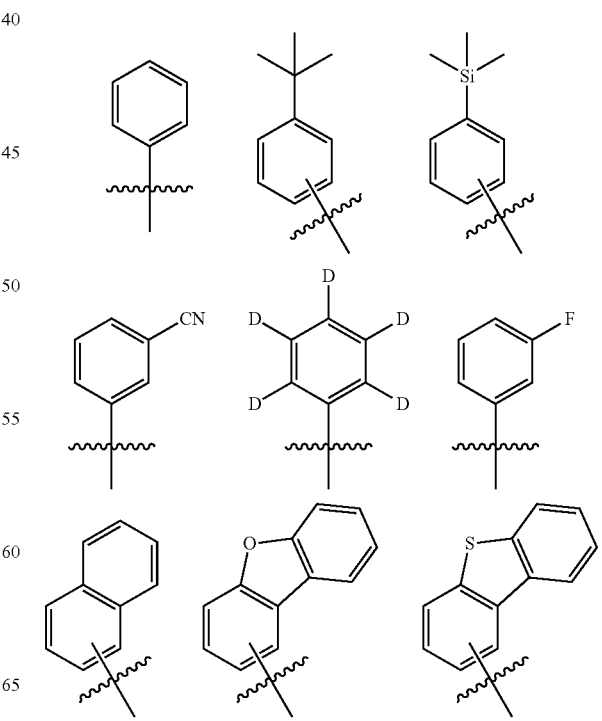

-continued

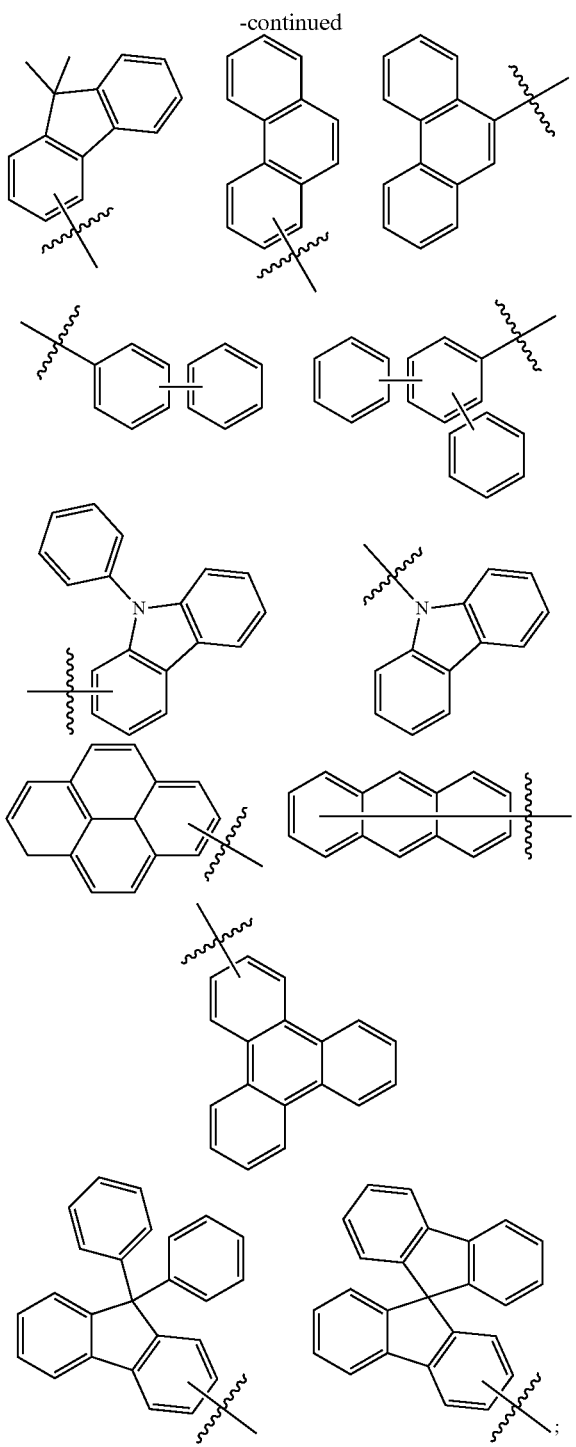

In the present disclosure, Ar is not limited to the above groups.

In some examples of the present disclosure, Ar may be an electron-deficiency heteroaryl (also called electron-deficient heteroaryl); hetero atoms thereon may reduce the electron cloud density of a conjugated system of heteroaryl generally, for example, lone pair electrons on hetero atoms do not participate in the conjugated system, and hetero atoms have stronger electronegativity, such that the electron cloud density of a conjugated system drops. For example, the electron deficiency heteroaryl may include, but not limited to, pyridyl, pyrimidyl, cyanuro, quinolyl, isoquinolyl, benzopyrazolyl, benzimidazolyl, quinoxalinyl, phenanthrolinyl, and the like. In this way, Ar may form an electron transport core moiety of the nitrogen-containing compound, such that the nitrogen-containing compound may effectively achieve electronic transmission, and may effectively balance the transmission rate between electrons and holes in the organic light-emitting layer. In this way, the nitrogen-containing compound may not only serve as a host material for a bipolar organic light-emitting layer to simultaneously transmit electrons and holes, but also serve as a host material of an electron-type organic light-emitting layer to be matched with a host material of a hole-type organic light-emitting layer.

Optionally, Ar is selected from the group consisting of substituents as shown in chemical formulas i-12 to i-18:

i-12

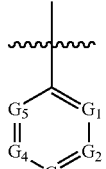

i-13

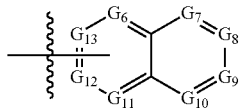

i-14

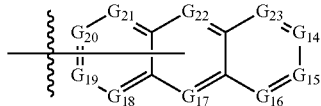

i-15

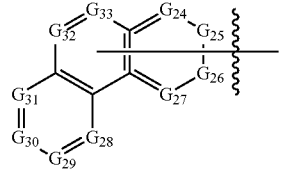

i-16

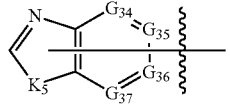

i-17

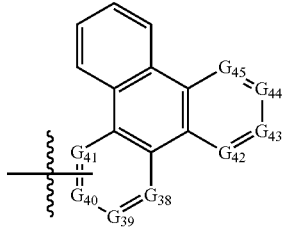

i-18

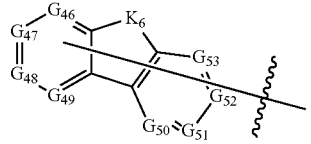

wherein, $G_1$ to $G_5$ are each independently selected from: N or $C(F_1)$, and at least one of $G_1$ to $G_5$ is selected from N;

when two or more of $G_1$ to $G_5$ are selected from $C(F_1)$, any two of $F_1$ are the same or different;

$G_6$ to $G_{13}$ are each independently selected from N or $C(F_2)$, and at least one of $G_6$ to $G_{13}$ is selected from N; when two or more of $G_6$ to $G_{13}$ are selected from $C(F_2)$, any two of $F_2$ are the same or different;

$G_{14}$ to $G_{23}$ are each independently selected from N or $C(F_3)$, and at least one of $G_{14}$ to $G_{23}$ is selected from N; when two or more of $G_{14}$ to $G_{23}$ are selected from $C(F_3)$, any two of $F_3$ are the same or different;

$K_6$ is selected from O, S, Se, $C(V_1V_2)$, $N(V_3)$ or $Si(V_1V_2)$;

$G_{24}$ to $G_{33}$ are each independently selected from N or $C(F_4)$, and at least one of $G_{24}$ to $G_{33}$ is selected from N; when two or more of $G_{24}$ to $G_{33}$ are selected from $C(F_4)$, any two of $F_4$ are the same or different;

$K_5$ is selected from O, S, Se, $N(V_4)$;

$G_{34}$ to $G_{37}$ are each independently selected from N or $C(F_5)$, and when two or more of $G_{34}$ to $G_{37}$ are selected from $C(F_5)$, any two of $F_5$ are the same or different;

$G_{38}$ to $G_{45}$ are each independently selected from N or $C(F_6)$, and at least one of $G_{38}$ to $G_{45}$ is selected from N; when two or more of $G_{38}$ to $G_{45}$ are selected from $C(F_6)$, any two of $F_6$ are the same or different;

$G_{46}$ to $G_{53}$ are each independently selected from N or $C(F_7)$, and at least one of $G_{46}$ to $G_{53}$ is selected from N; when two or more of $G_{46}$ to $G_{53}$ are selected from $C(F_7)$, any two of $F_7$ are the same or different;

$F_1$ to $F_7$ are each independently selected from: hydrogen, deuterium, F, Cl, Br, cyano, aryl with 6 to 20 carbon atoms, heteroaryl with 3 to 20 carbon atoms, trialkylsilyl with 3 to 12 carbon atoms, arylsilyl with 8 to 12 carbon atoms, alkyl with 1 to 10 carbon atoms, haloalkyl with 1 to 10 carbon atoms, alkenyl with 2 to 6 carbon atoms, cycloalkyl with 3 to 10 carbon atoms, heterocycloalkyl with 2 to 10 carbon atoms, alkoxy with 1 to 10 carbon atoms, alkylamino with 1 to 10 carbon atoms, arylthio with 1 to 10 carbon atoms, aryloxy with 6 to 18 carbon atoms, and arylthio with 6 to 18 carbon atoms;

$V_1$ to $V_4$ are each independently selected from: aryl with 6 to 20 carbon atoms, heteroaryl with 3 to 20 carbon atoms, alkyl with 1 to 10 carbon atoms, cycloalkyl with 3 to 10 carbon atoms, and heterocycloalkyl with 2 to 10 carbon atoms; or $V_1$ and $V_2$ are connected with each other to form a saturated or unsaturated 5- to 13-membered ring together with the atom to which they are jointly connected.

Preferably, at least two of $Q_1$ to $Q_5$ are selected from N;
Preferably, at least two of $Q_6$ to $Q_{13}$ are selected from N;
Preferably, at least two of $Q_{14}$ to $Q_{23}$ are selected from N;
Preferably, at least two of $Q_{24}$ to $Q_{33}$ are selected from N;
Preferably, at least two of $Q_{38}$ to $Q_{45}$ are selected from N;
Preferably, at least two of $Q_{46}$ to $Q_{53}$ are selected from N.

In some other embodiments, optionally, Ar is selected from the group consisting of the following substituents:

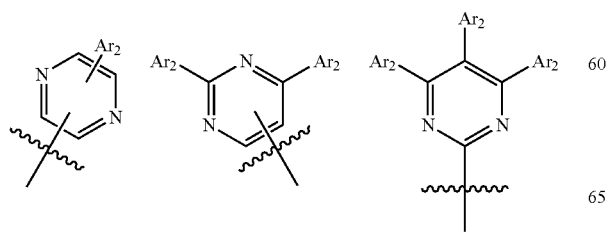

-continued

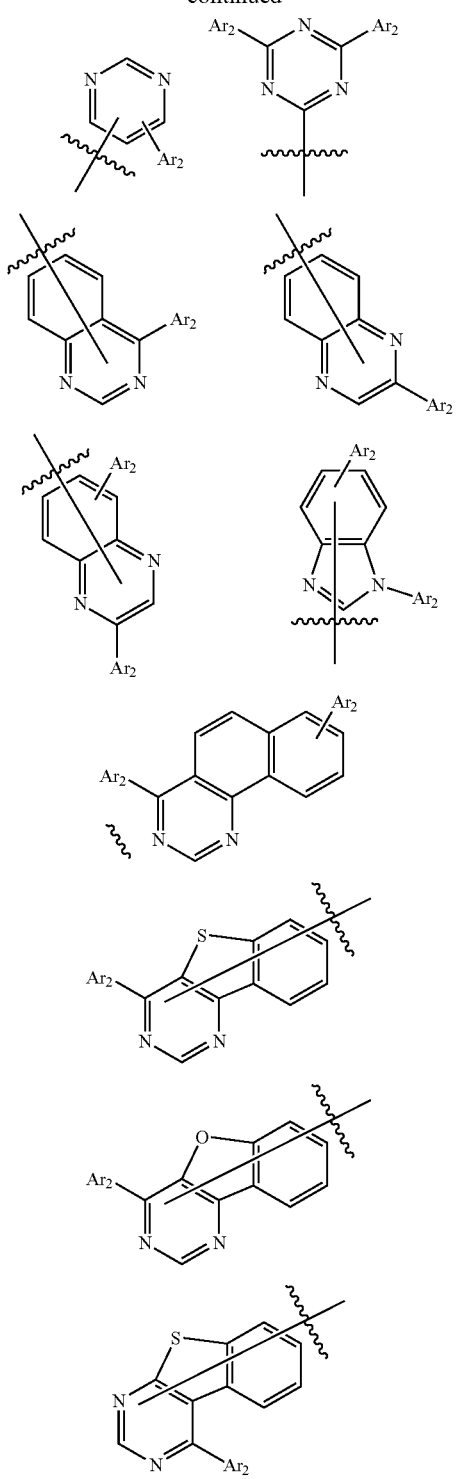

-continued

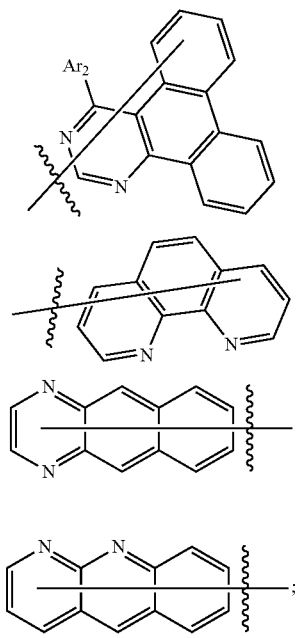

wherein, Ar₂ is selected from hydrogen, deuterium, substituted or unsubstituted aryl with 6 to 20 carbon atoms, substituted or unsubstituted heteroaryl with 3 to 20 carbon atoms; any two of Ar₂ are the same or different;

substituents in Ar₂ are selected from deuterium, F, Cl, cyano, alkyl with 1 to 6 carbon atoms, alkoxy with 1 to 6 carbon atoms, alkylamino with 1 to 6 carbon atoms, cycloalkyl with 3 to 10 carbon atoms, aryl with 6 to 20 carbon atoms, heteroaryl with 3 to 20 carbon atoms, alkoxy with 1 to 4 carbon atoms, haloalkyl with 1 to 4 carbon atoms, and alkylsilyl with 3 to 9 carbon atoms; and when Ar₂ has a plurality of substituents, any two of the substituents are the same or different.

Further, the Ar₂ is selected from: hydrogen, substituted or unsubstituted phenyl, substituted or unsubstituted naphthyl, substituted or unsubstituted anthracyl, substituted or unsubstituted phenanthryl, substituted or unsubstituted perylenyl, substituted or unsubstituted fluoranthracyl, substituted or unsubstituted chrysenyl, substituted or unsubstituted biphenyl, substituted or unsubstituted terphenyl, substituted or unsubstituted fluorenyl, substituted or unsubstituted dibenzothiophenyl, substituted or unsubstituted dibenzofuryl, substituted or unsubstituted N-phenylcarbazolyl, substituted or unsubstituted carbazole-9-yl-phenyl, substituted or unsubstituted pyridyl, substituted or unsubstituted pyrimidyl, substituted or unsubstituted pyrazinyl, substituted or unsubstituted quinolyl, substituted or unsubstituted isoquinolyl, substituted or unsubstituted quinazolinyl, substituted or unsubstituted benzoxazinyl, substituted or unsubstituted triphenyl;

substituents in Ar₂ are independently selected from F, deuterium, cyano, trifluoromethyl, trimethylsilyl, methyl, ethyl, isopropyl, tert-butyl, methoxy, ethyoxyl, isopropoxy, trifluoromethyl, cyclopentyl, cyclohexyl, phenyl, naphthyl, pyridyl, pyrimidyl, quinolyl, and isoquinolyl.

Optionally, the number of substituents on Ar₂ is 0, 1, 2, 3, 4 or 5.

In some more detailed embodiments, Ar is selected from the group consisting of the following substituents:

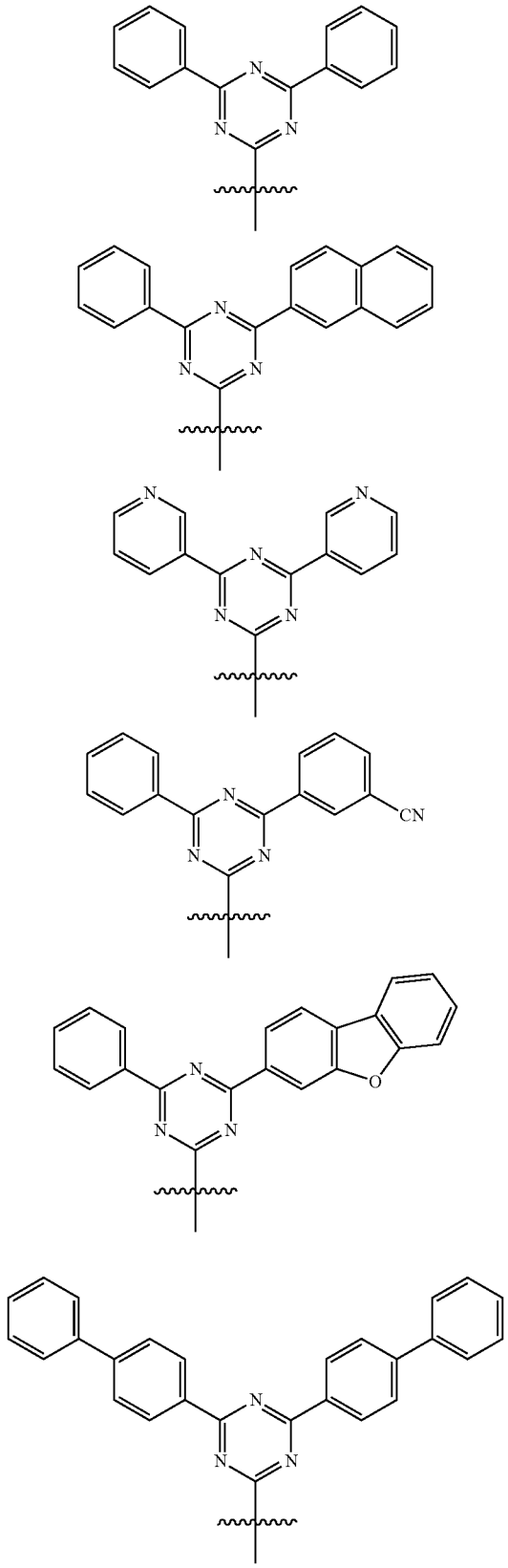

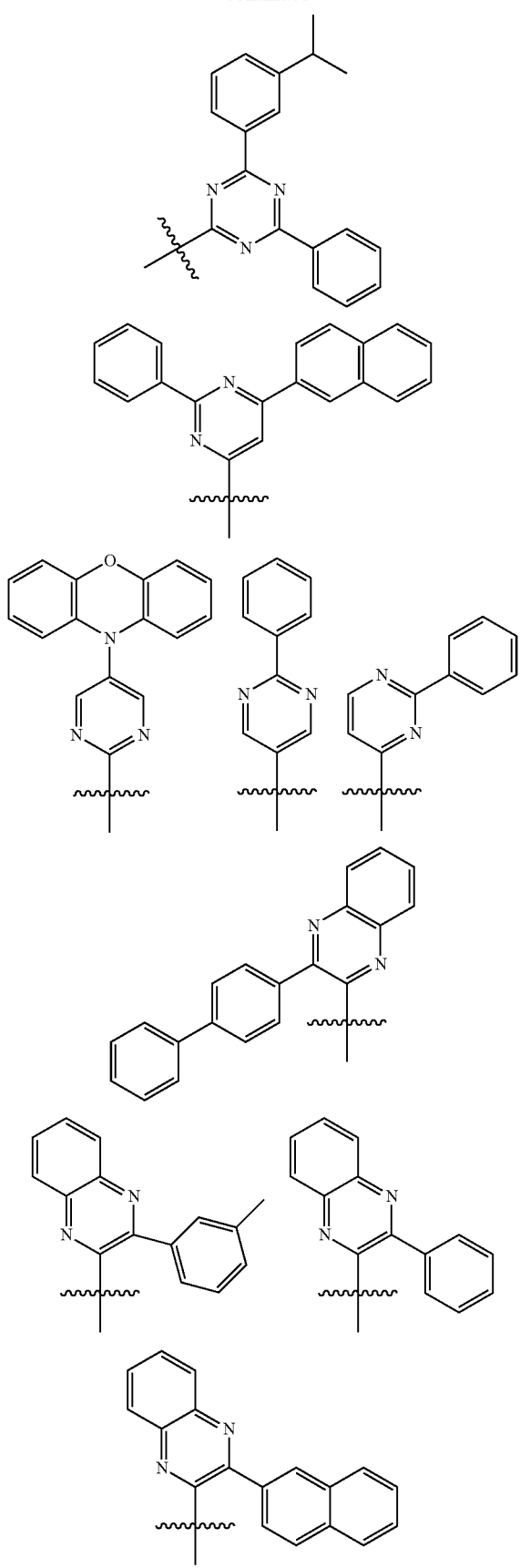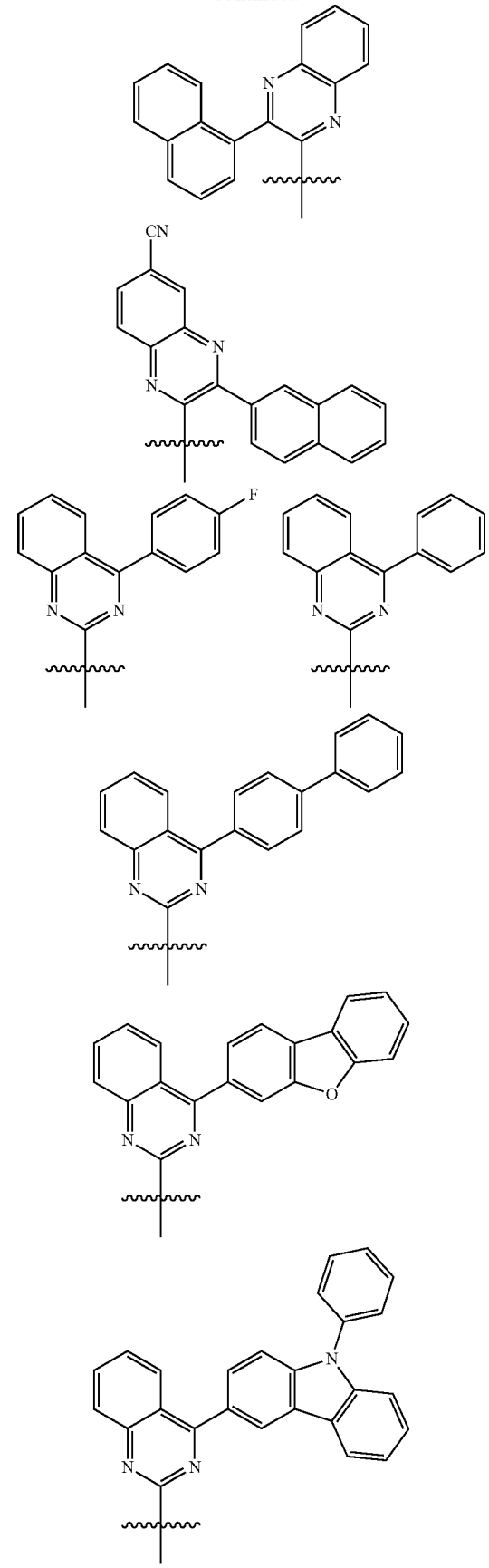

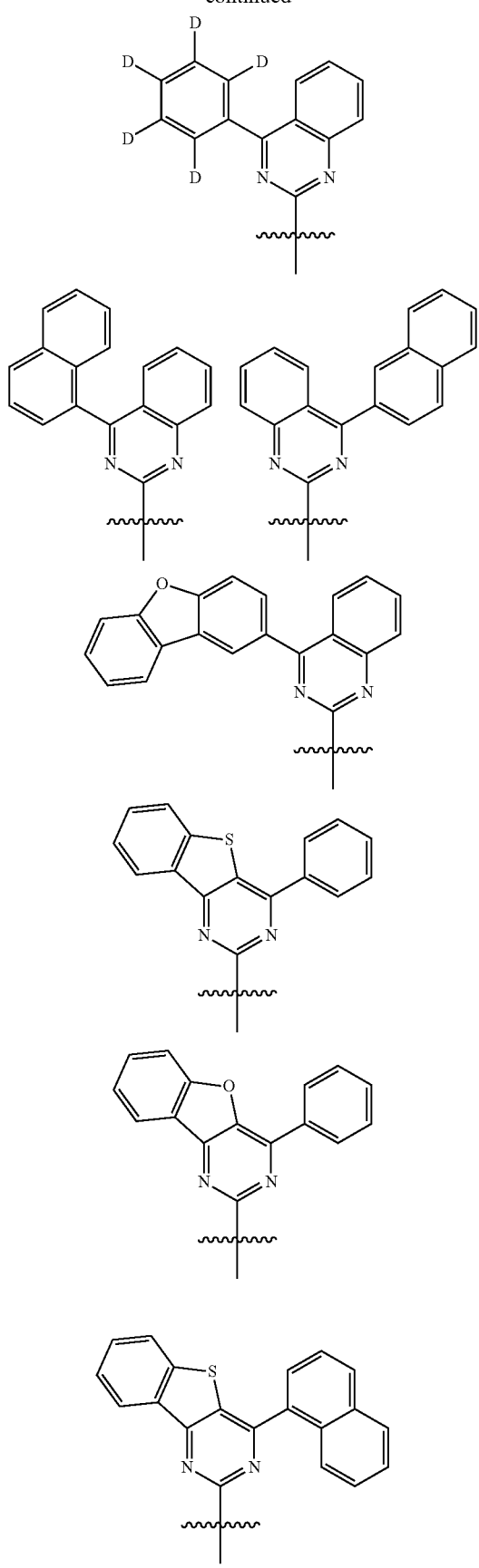
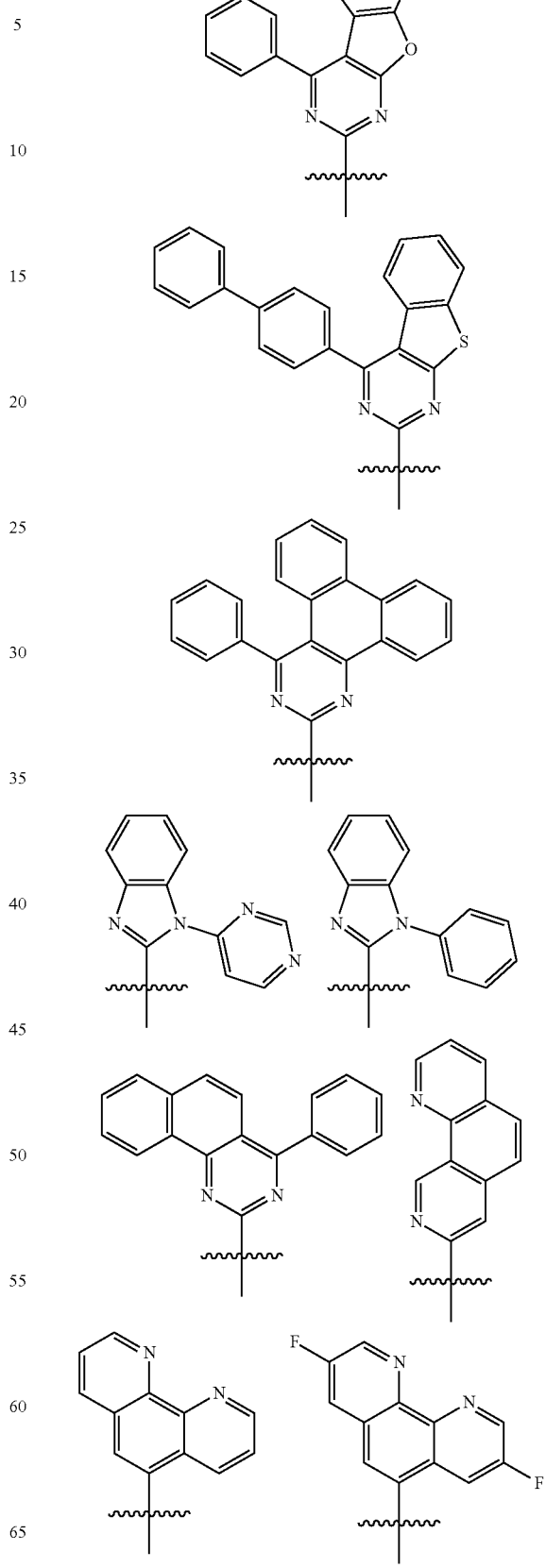

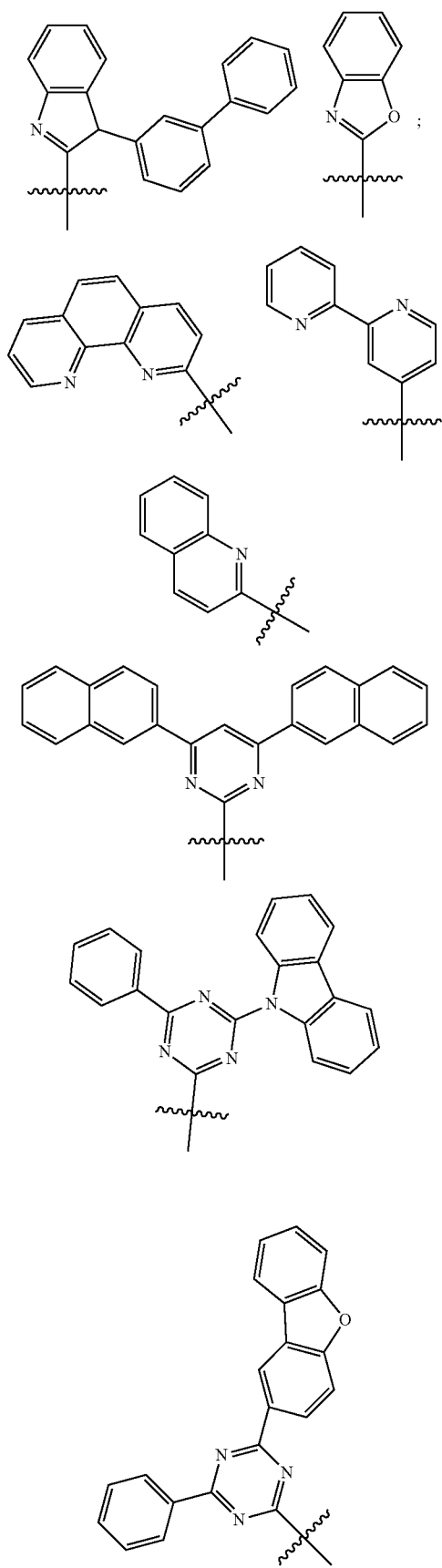
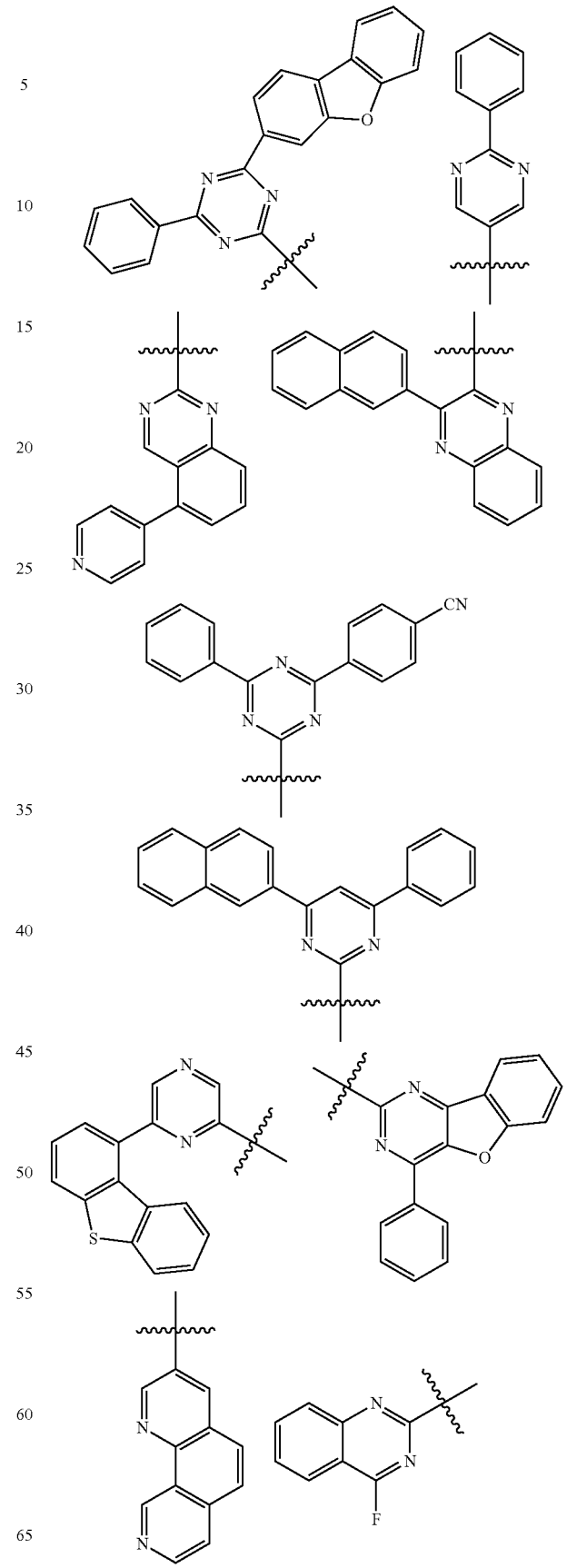

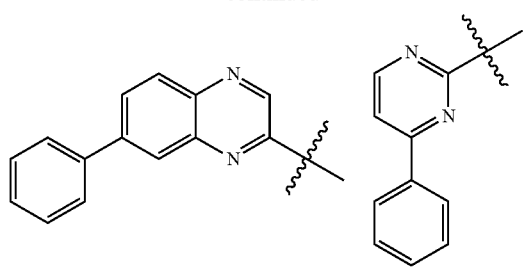

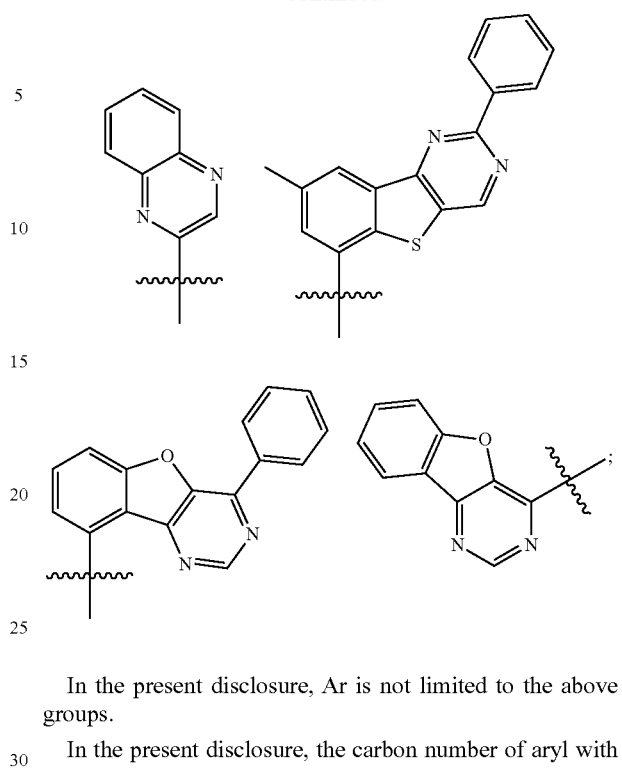

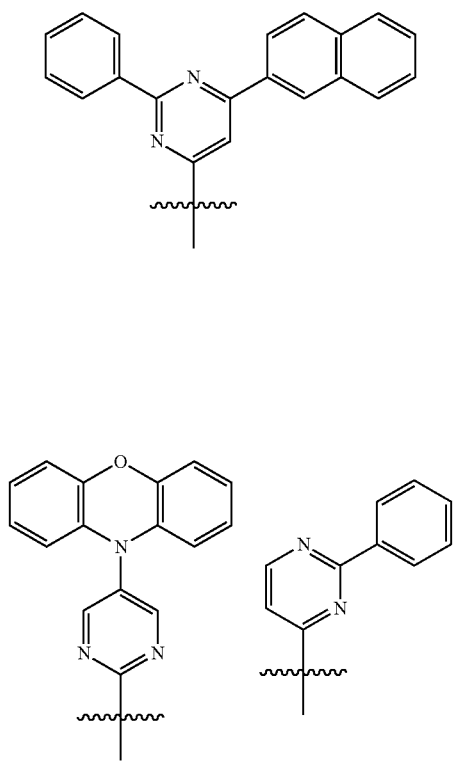

In the present disclosure, Ar is not limited to the above groups.

In the present disclosure, the carbon number of aryl with 6 to 20 carbon atoms is, for example, 6 (phenyl), 10 (naphthyl), 12 (biphenyl), 13 (fluorenyl), 14, 15 (dimethyl-fluorenyl), 16, and the like. The carbon number of heteroaryl with 3 to 18 carbon atoms is, for example, 5, 8, 12, 15, and the like.

In the present disclosure, specific examples of trialkylsilyl with 3 to 12 carbon atoms include, but not limited to, trimethylsilyl, triethylsilyl, and the like.

In the present disclosure, specific examples of with 3 to 10 carbon atoms cycloalkyl include, but not limited to, cyclopentyl, cyclohexyl, adamantyl, and the like.

Optionally, the nitrogen-containing compound is selected from the group consisting of the following compounds 1 to 143:

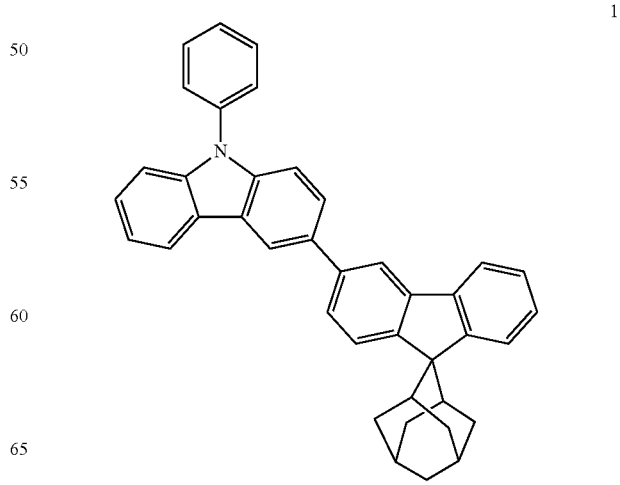

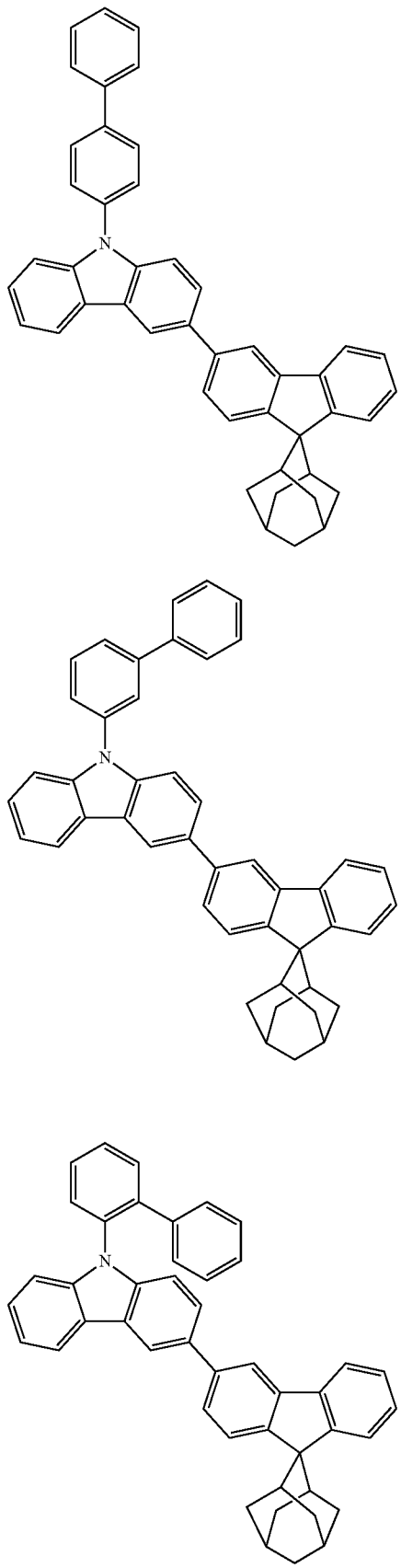
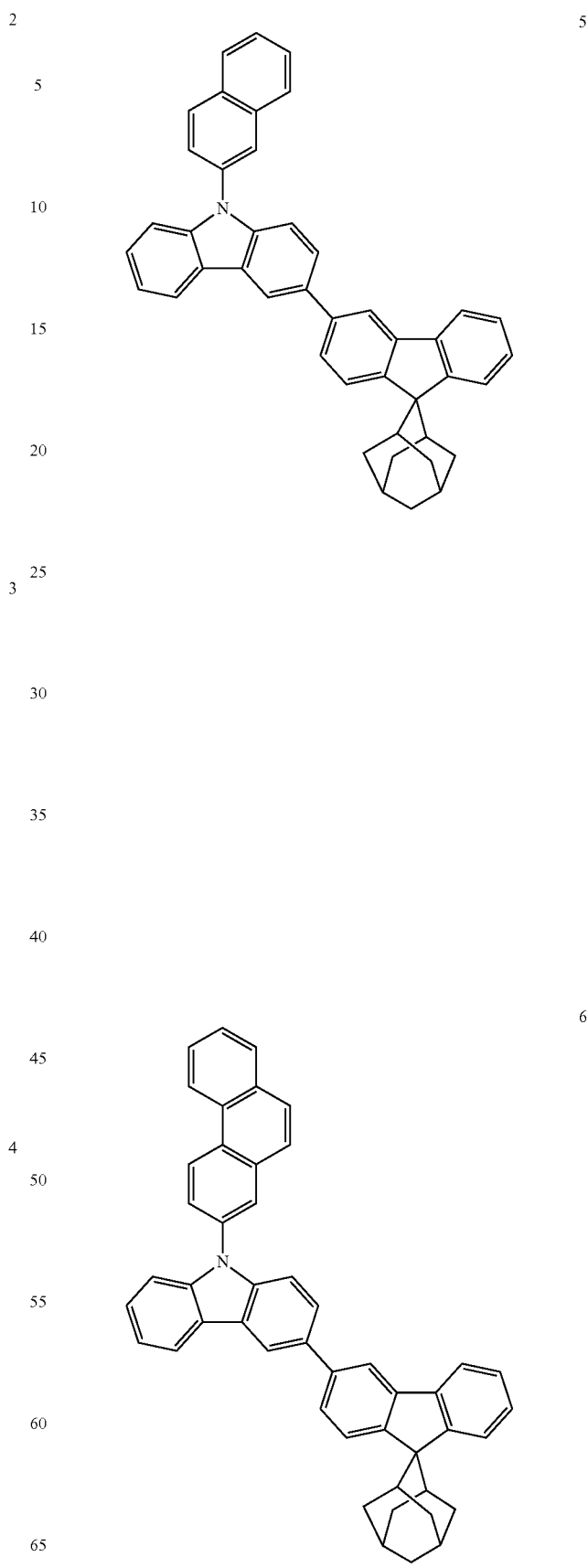

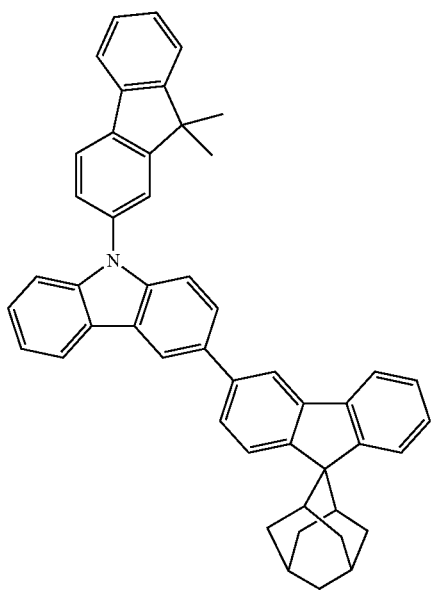
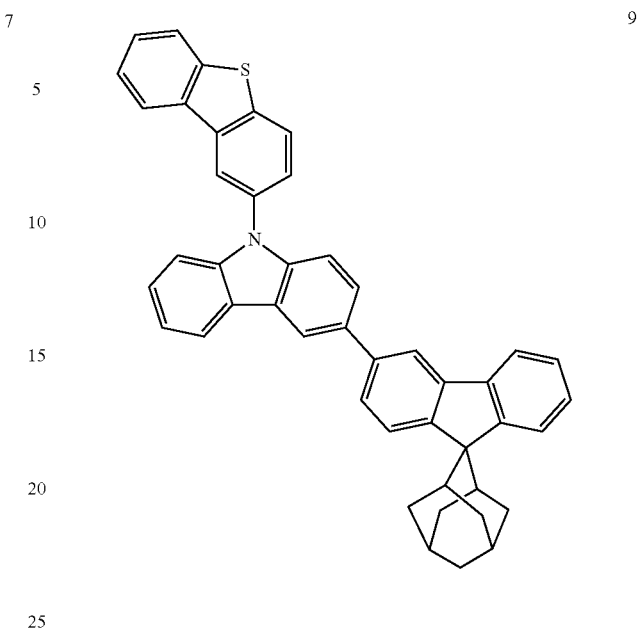
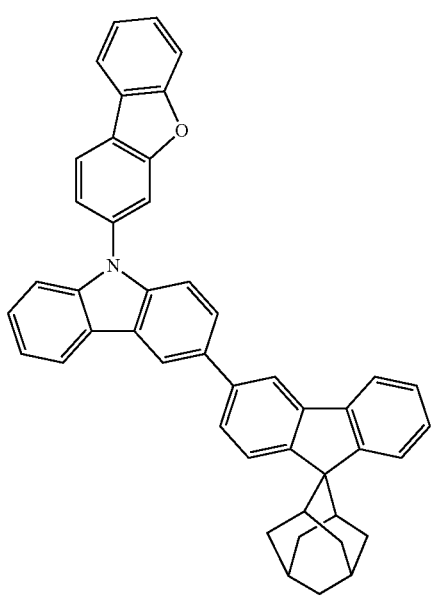
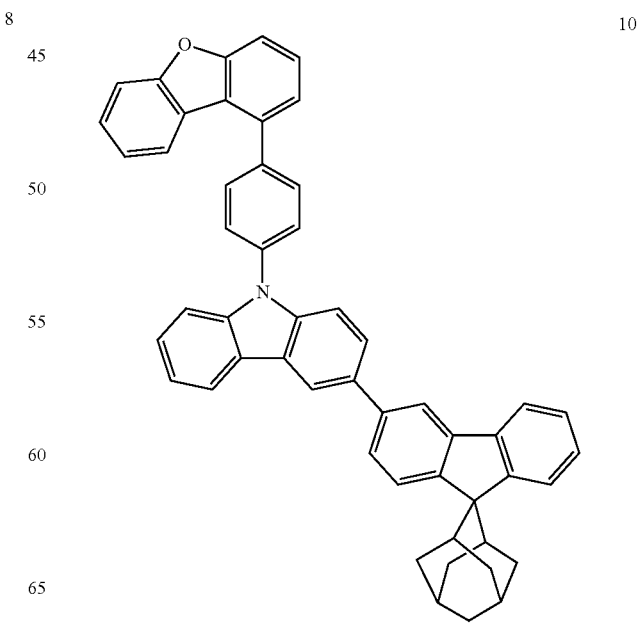

11
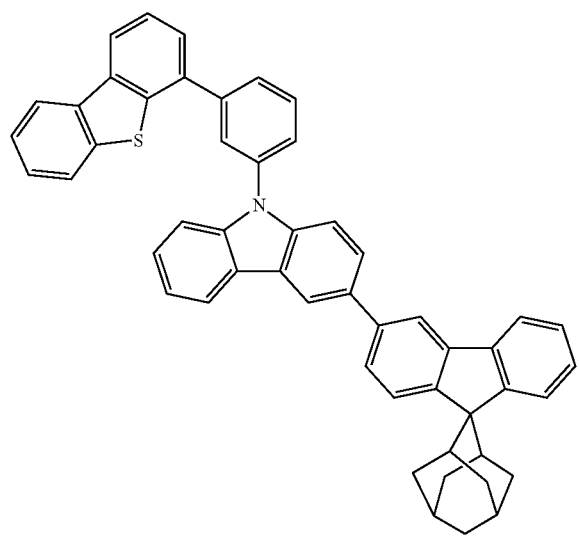
13
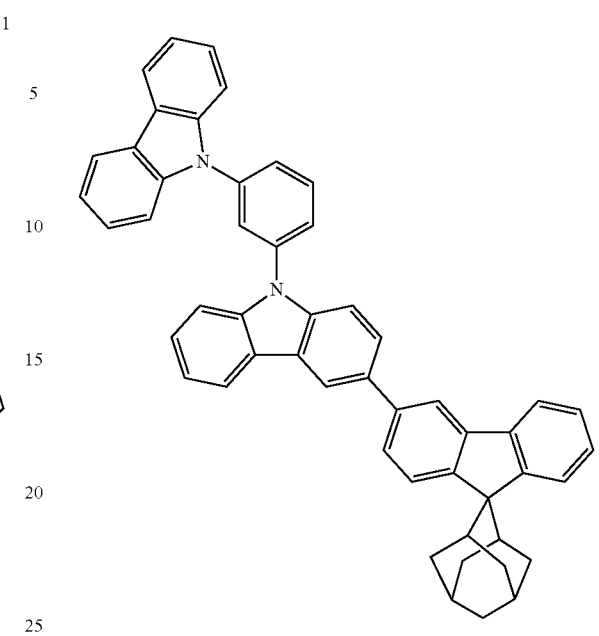
12
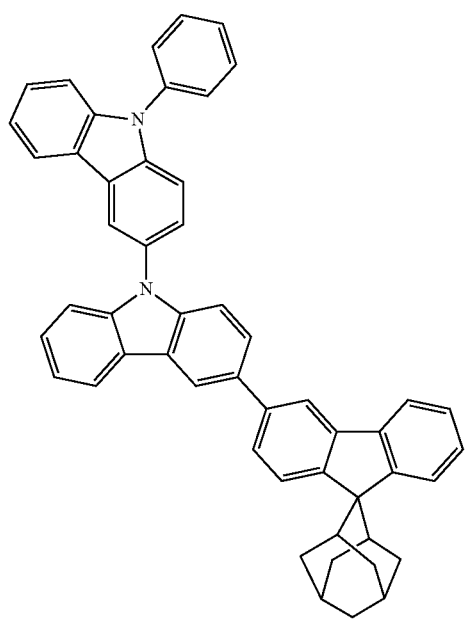
14
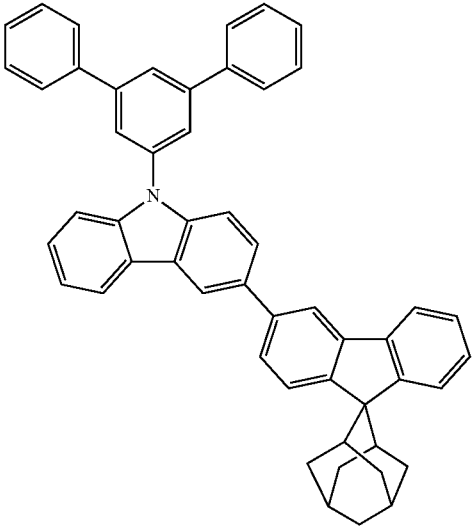

15
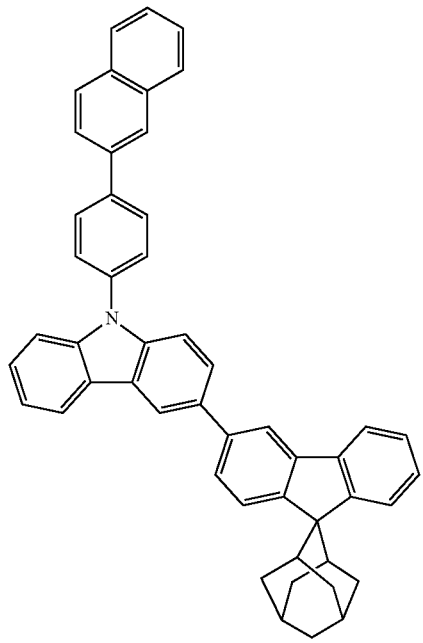
16
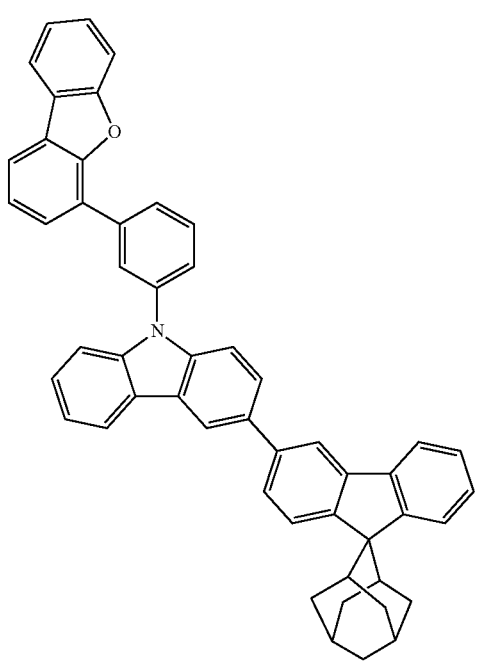
17
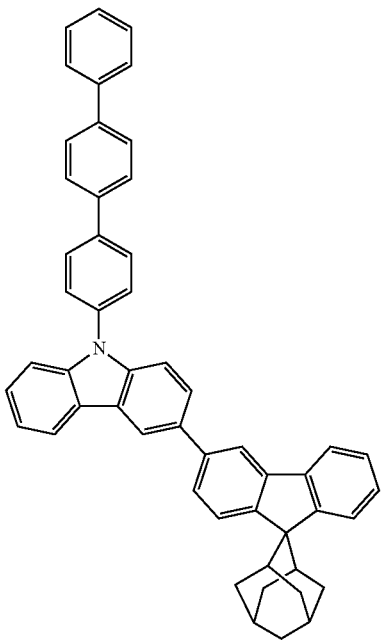
18
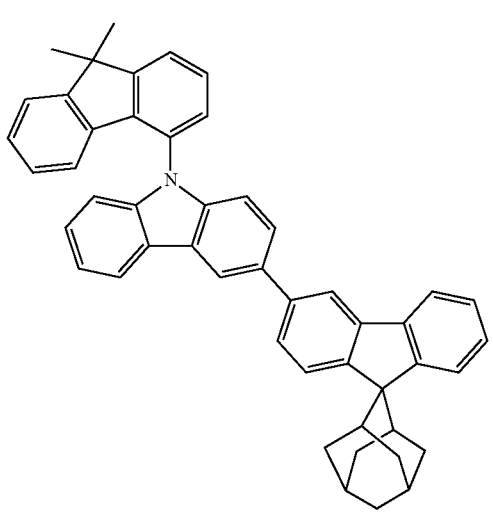

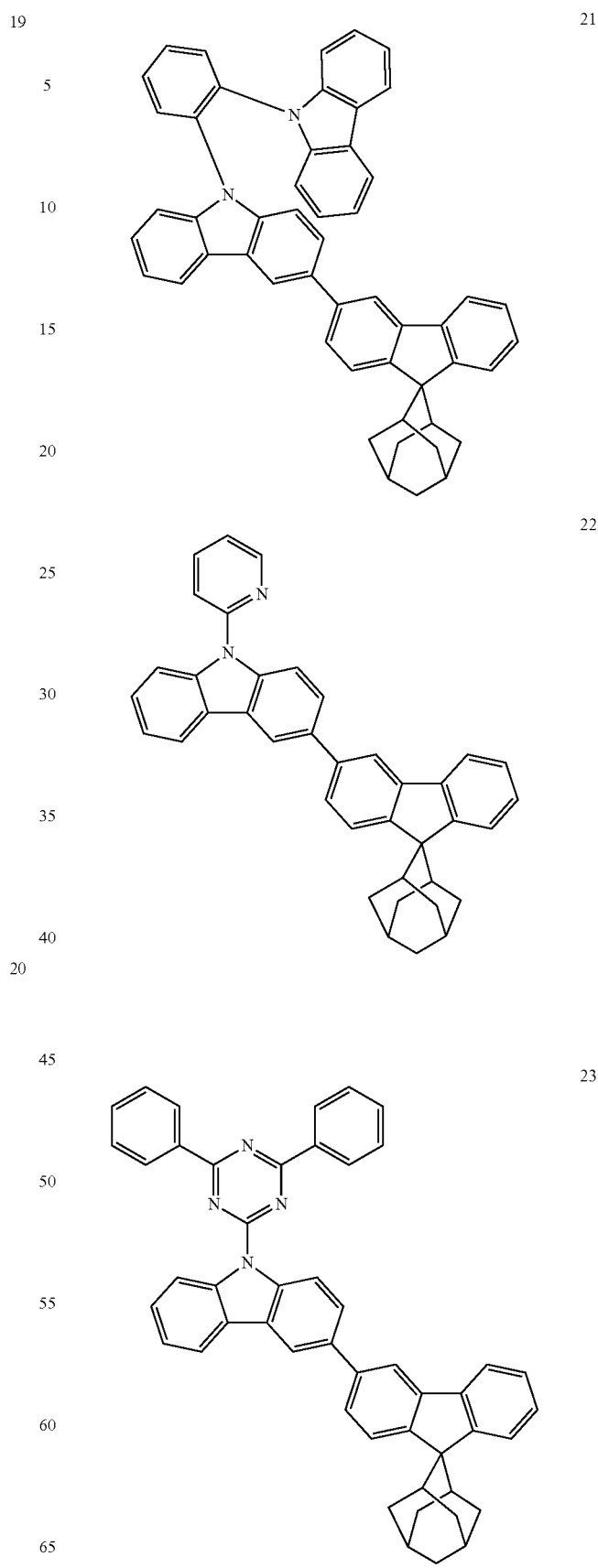

24
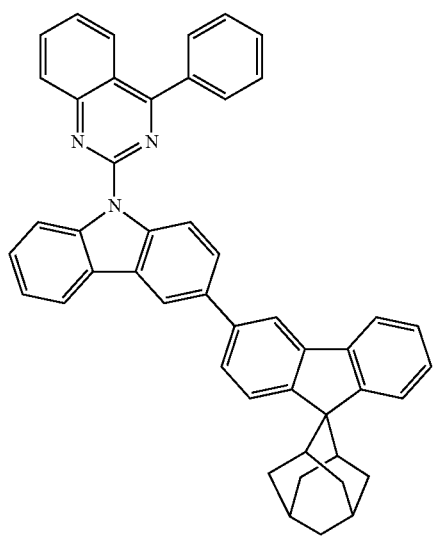
25
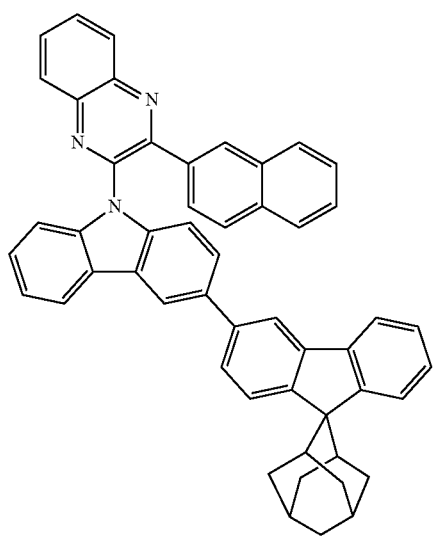
26
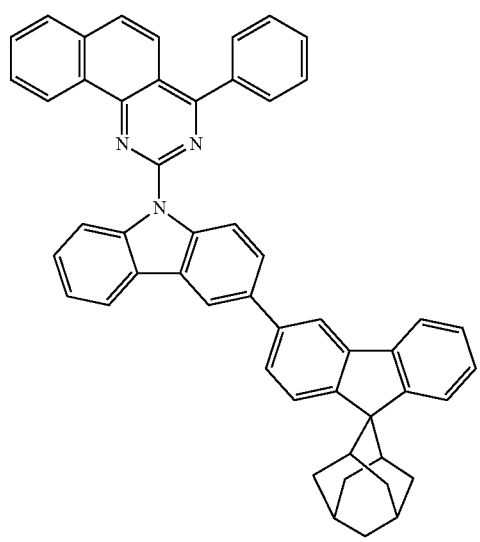
27
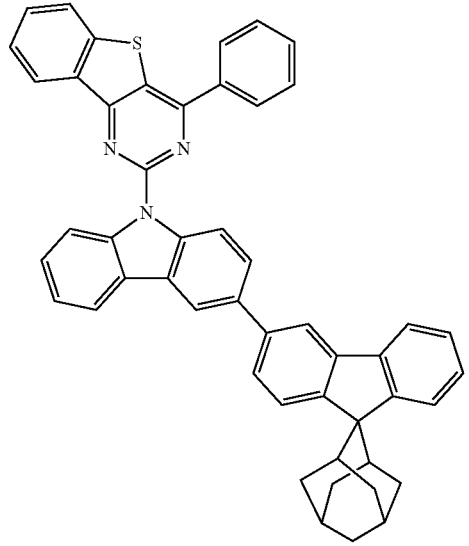
28
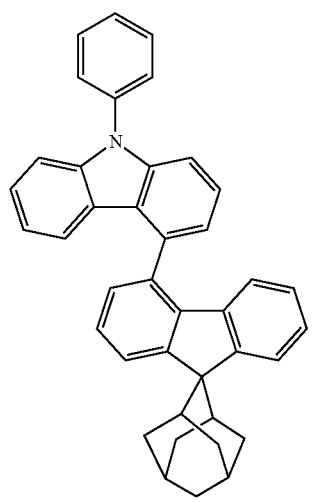
29
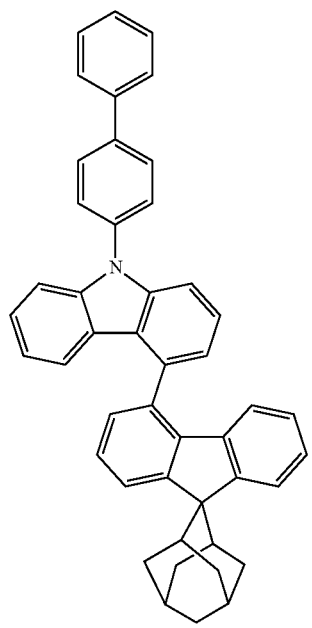

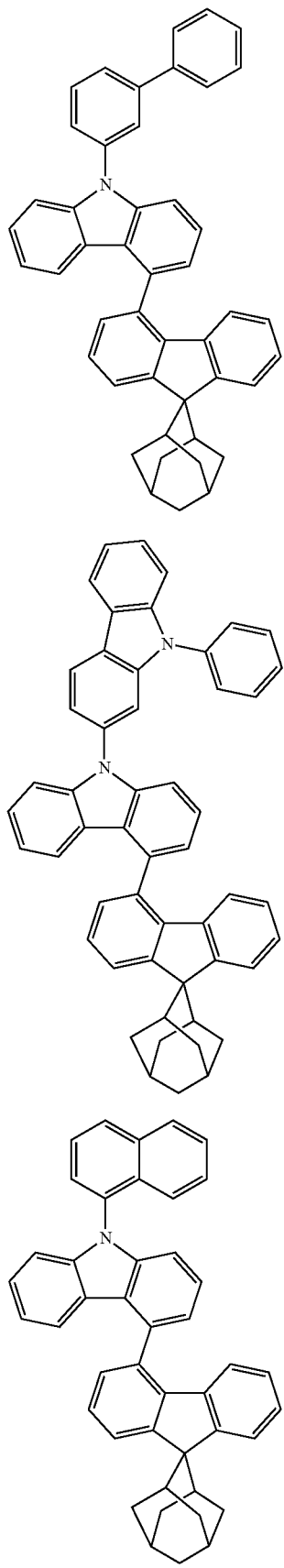

35
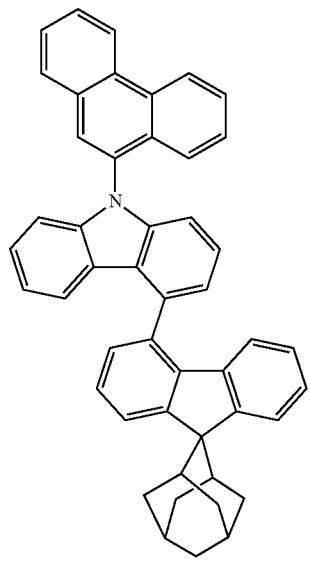
36
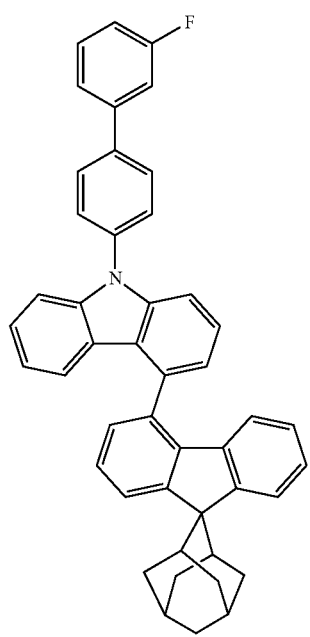
37
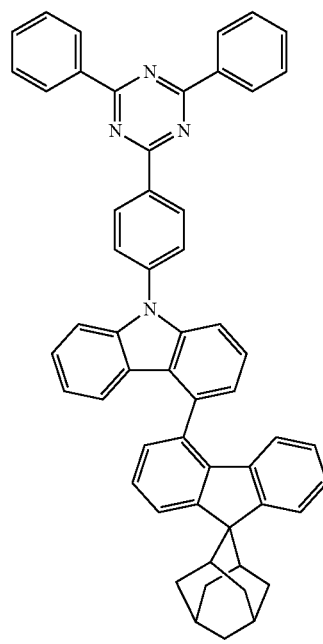
38
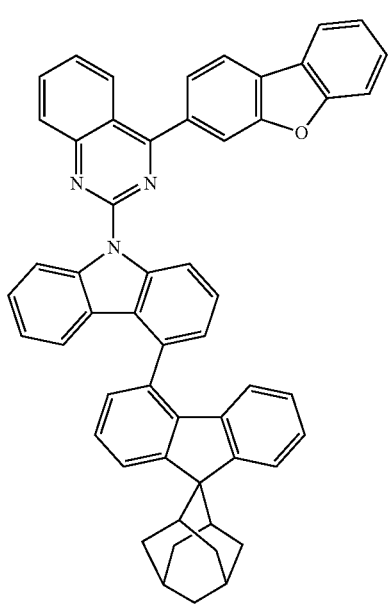
39
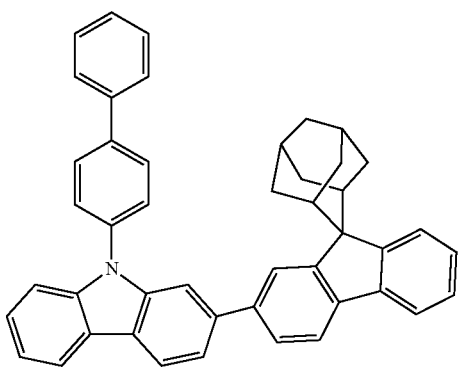

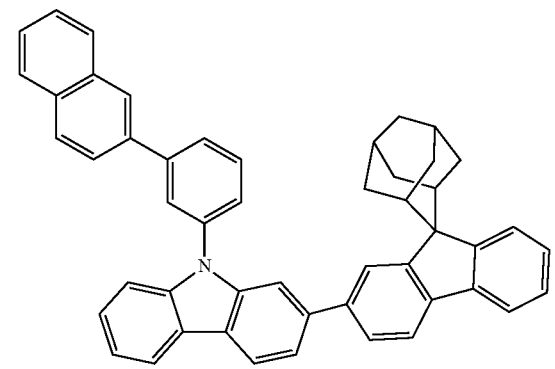
40
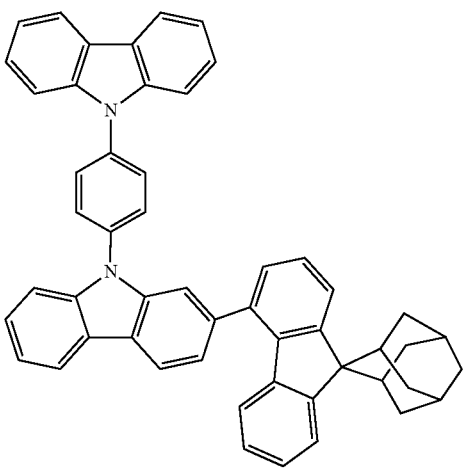
44
41
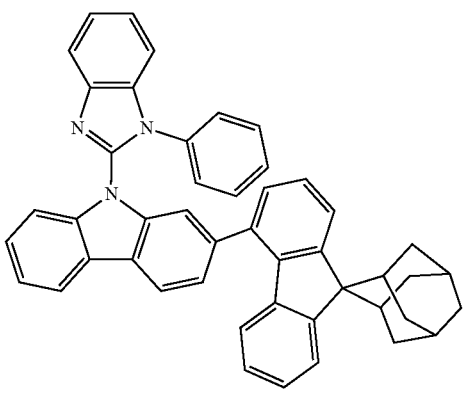
45
42
43
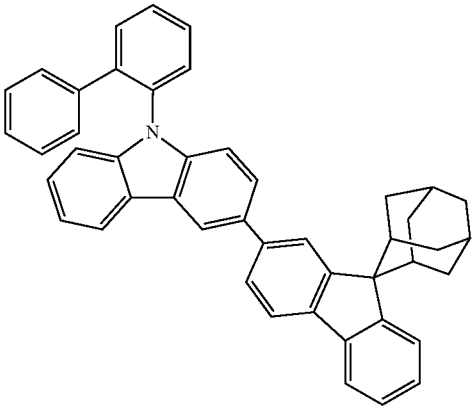
46

47
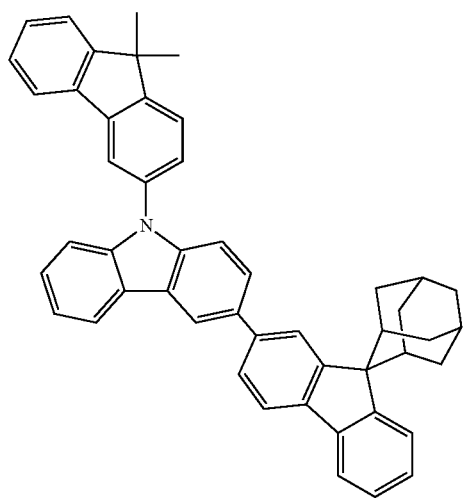
48
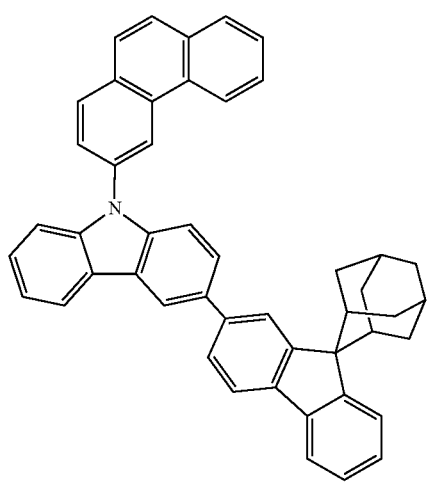
49
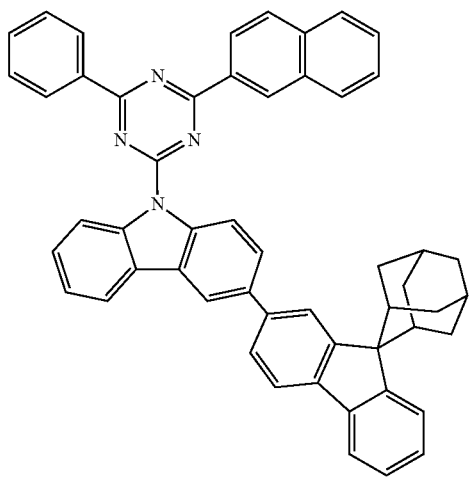
50
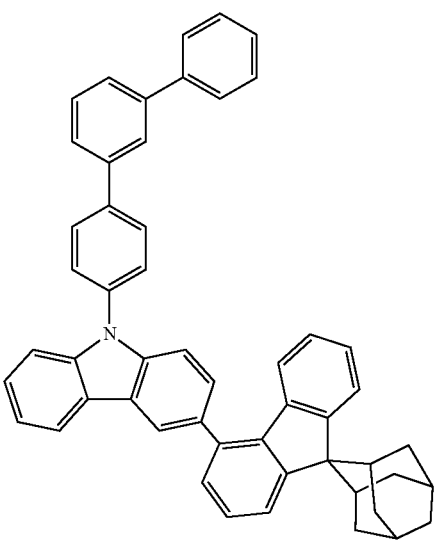
51
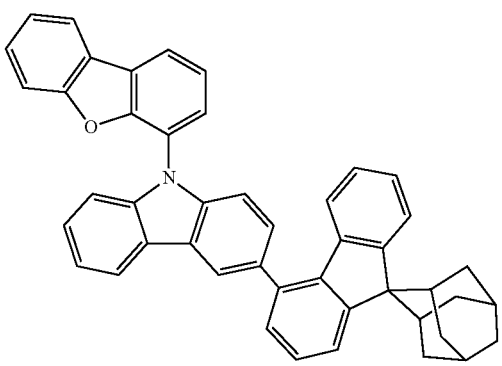
52
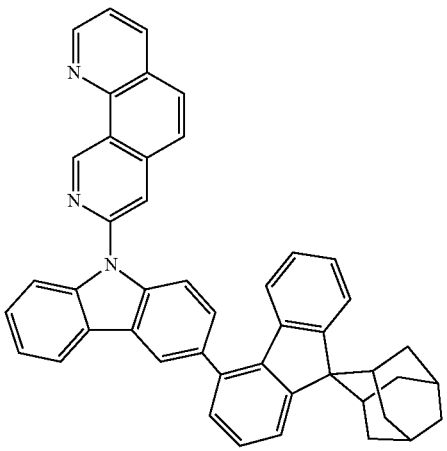

53
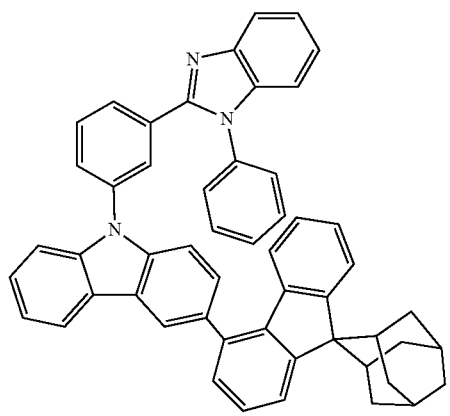
54
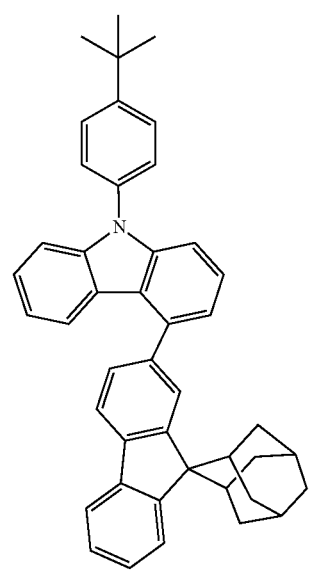
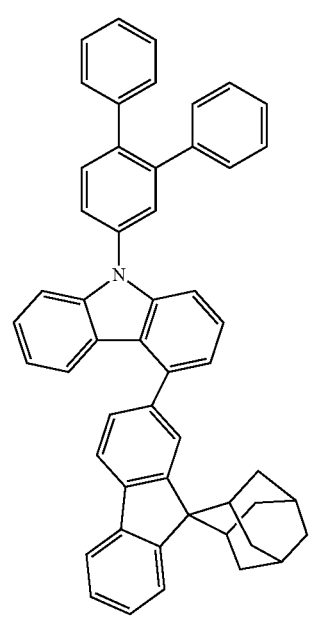
56
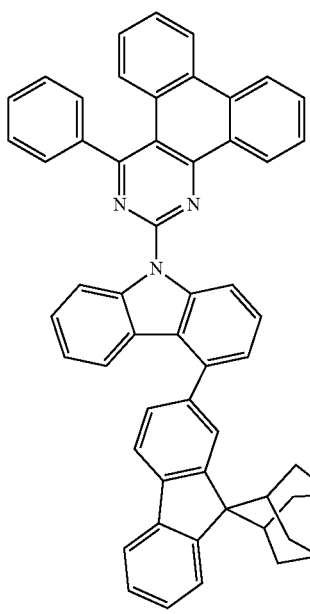
57
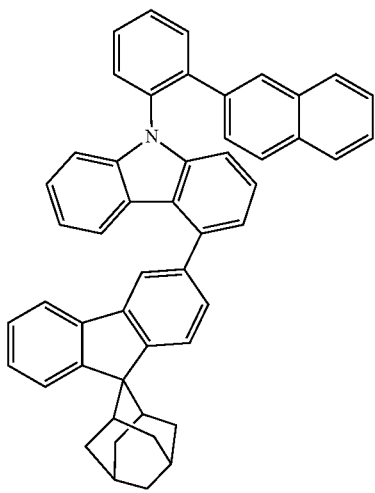

58
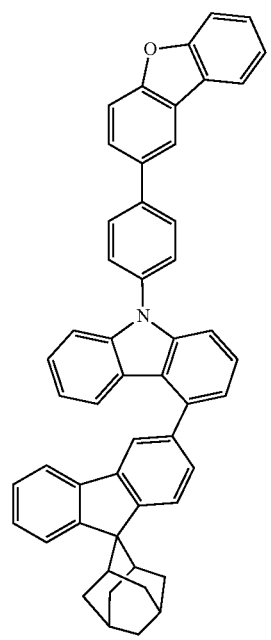
59
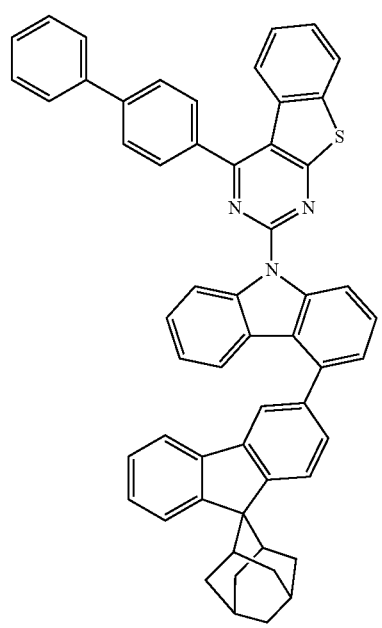
60
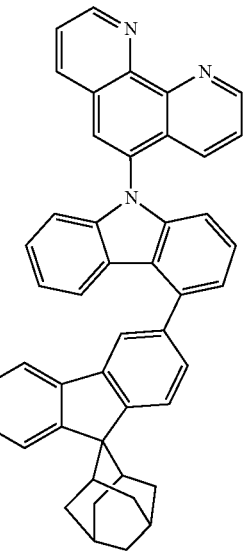
61
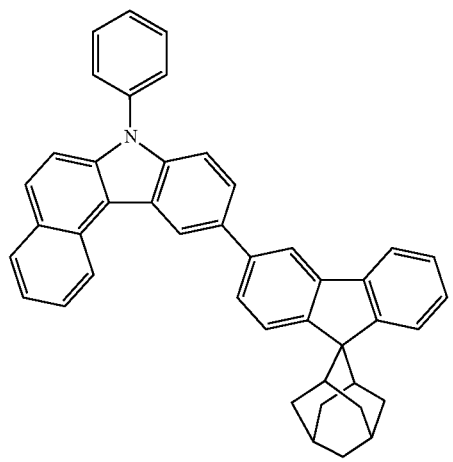
62
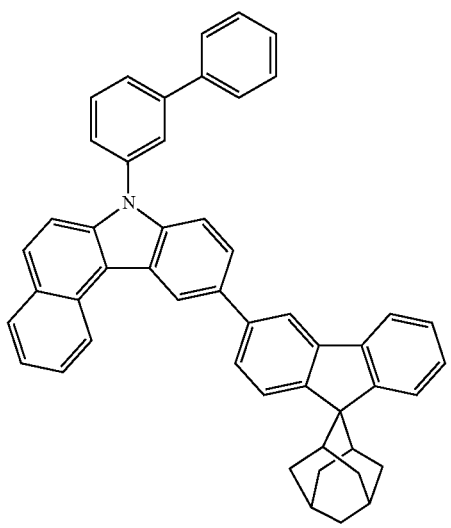

63
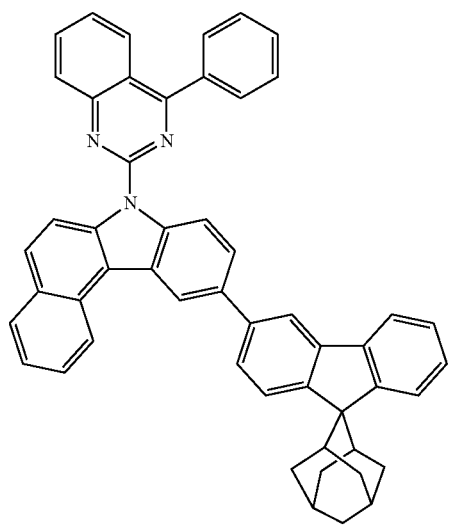
64
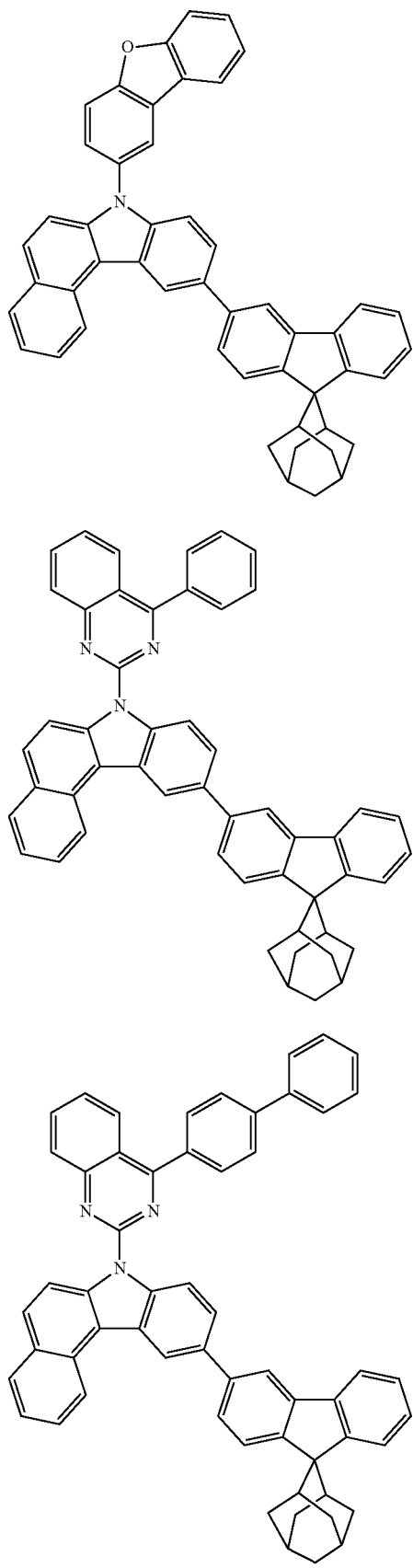
65
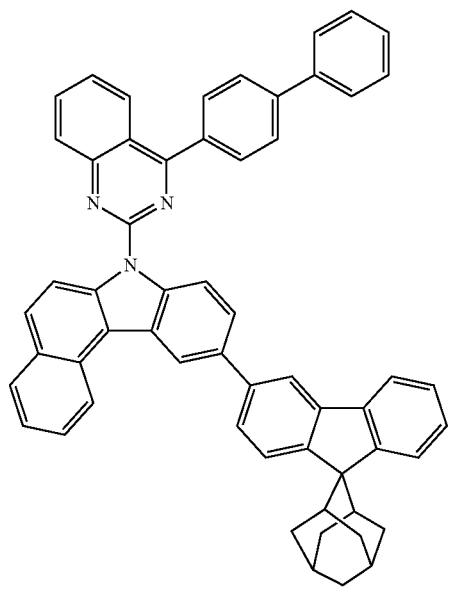
66
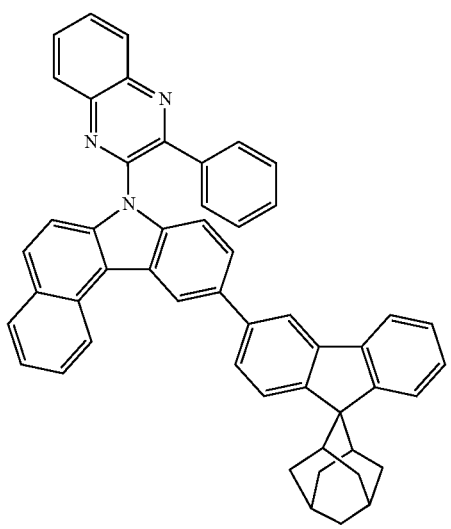
67
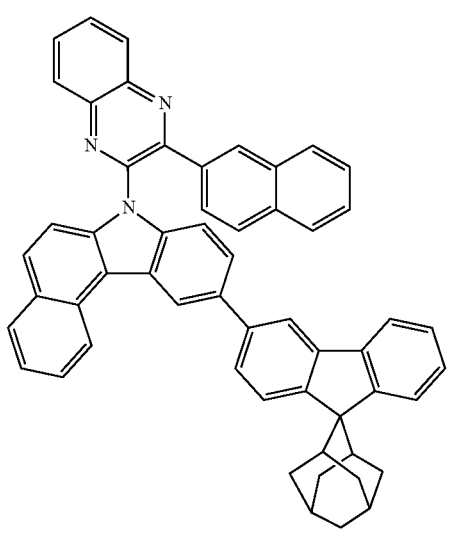
68
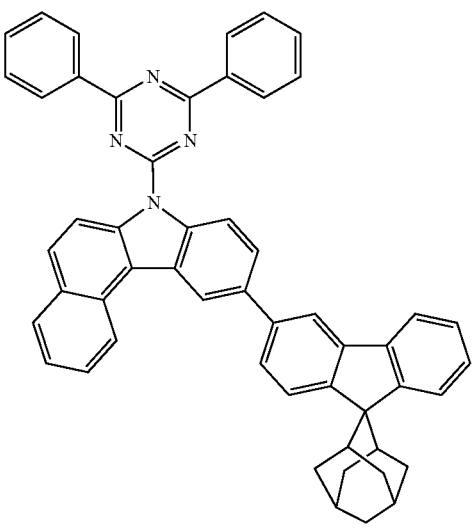

73
69
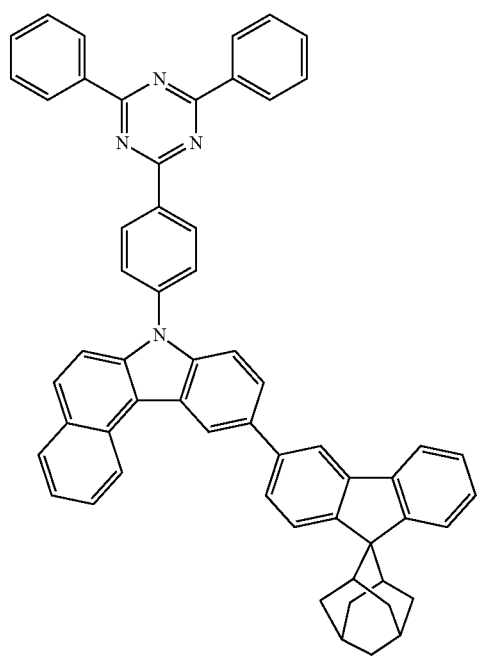
70
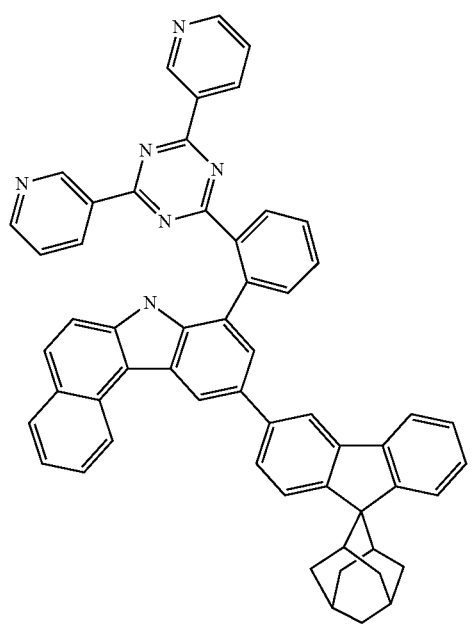
74
71
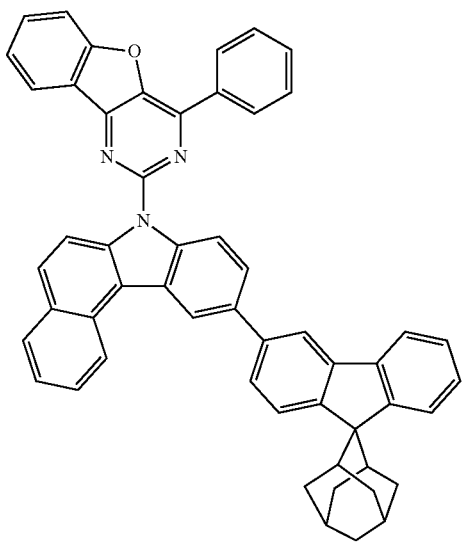
72
73

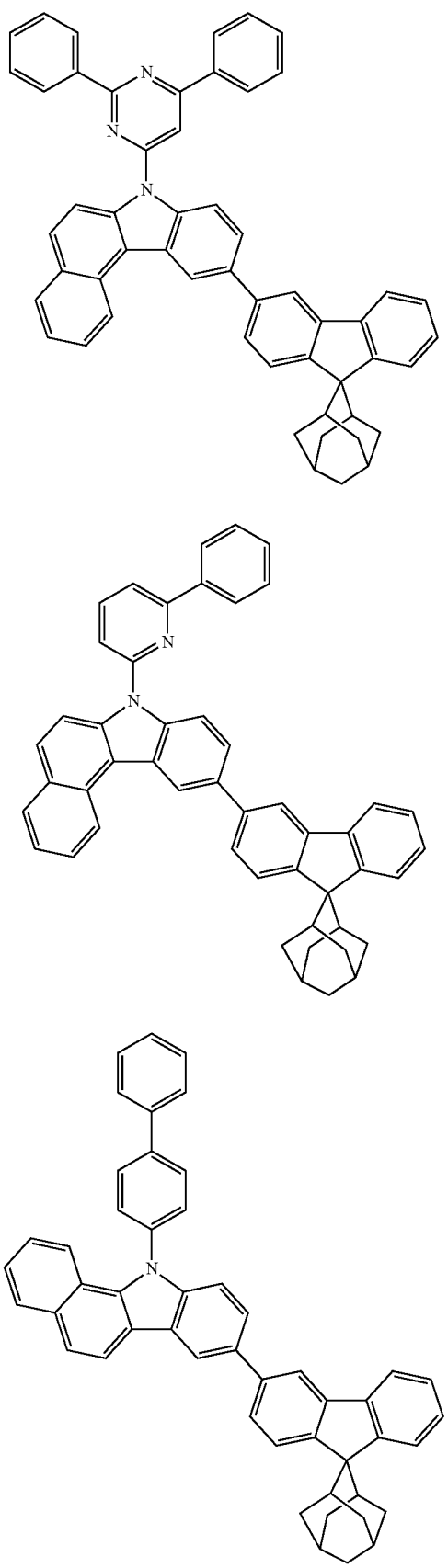

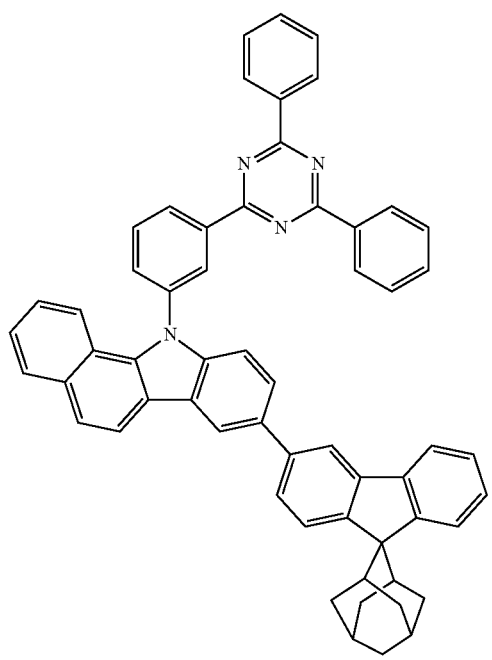
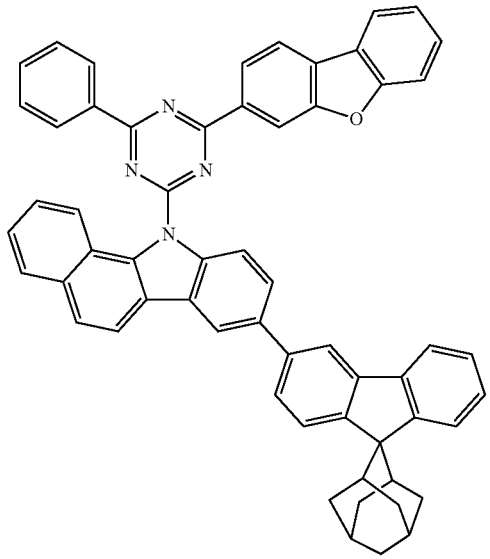

83
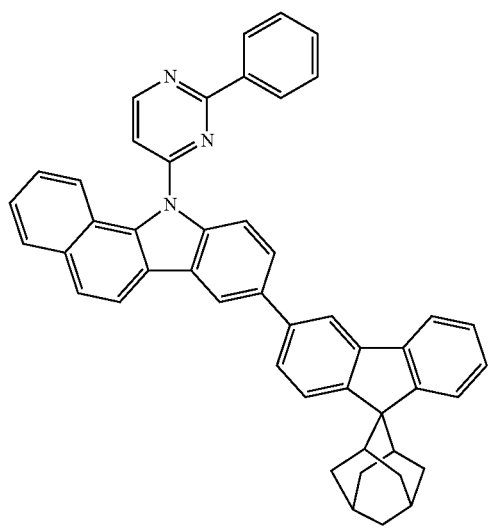
85
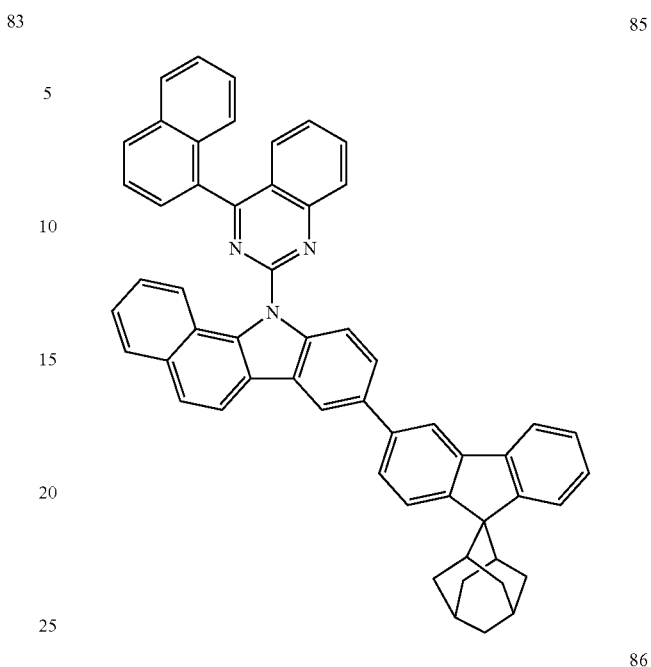
86
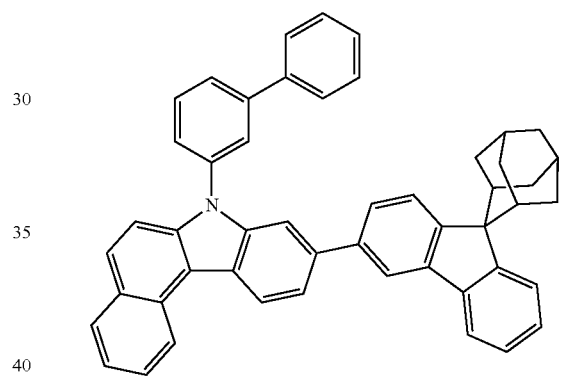
84
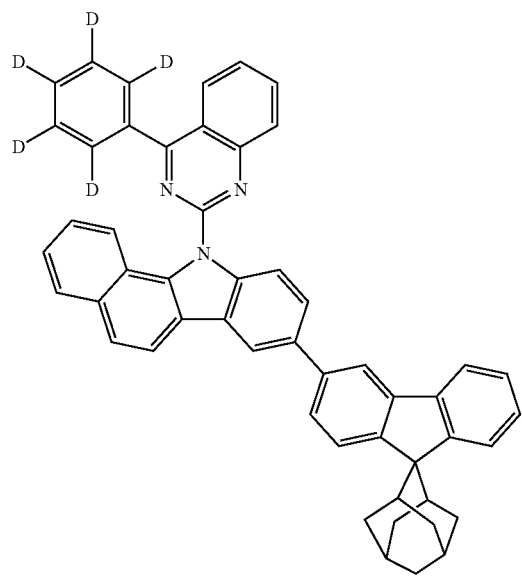
87

81
-continued
88
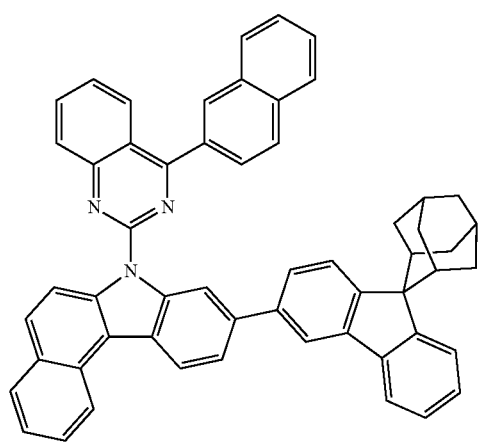
89
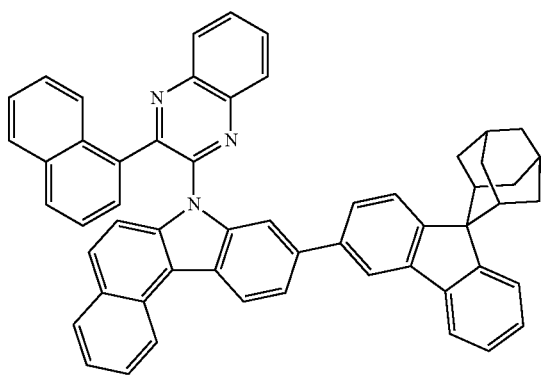
90
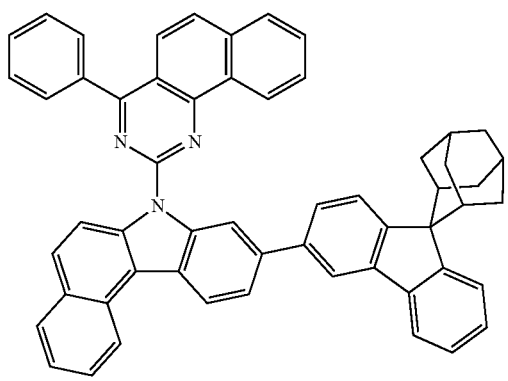
82
-continued
91
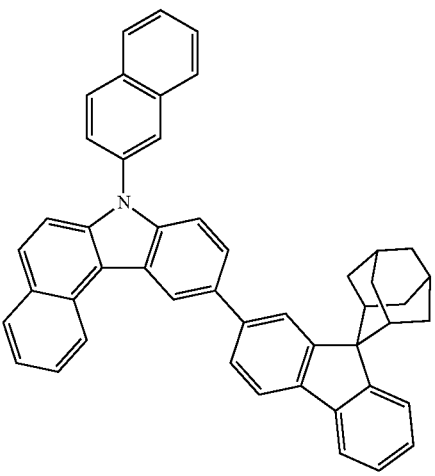
92
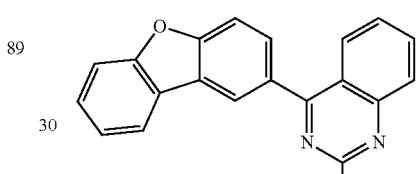
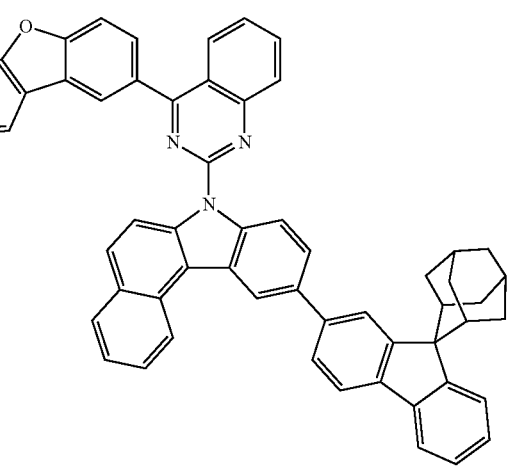
93
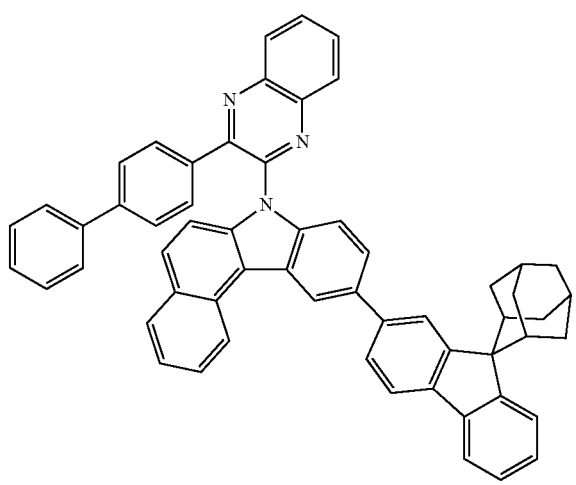

94
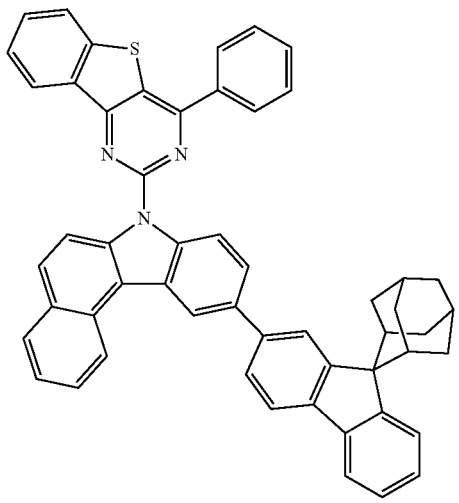
95
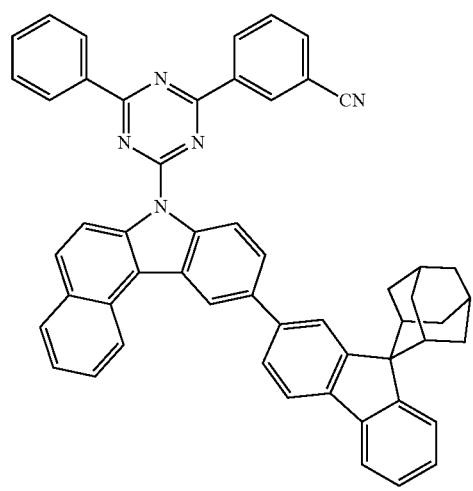
96
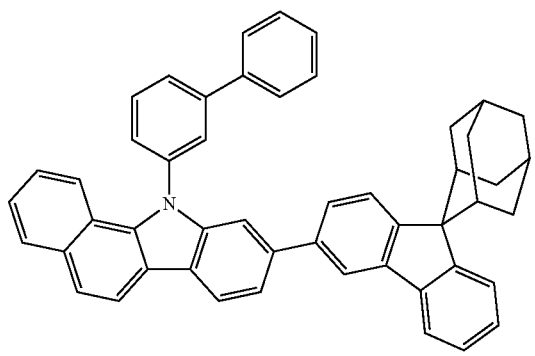
97
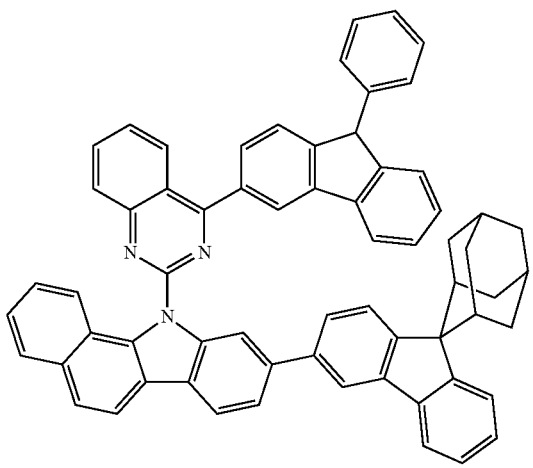
98
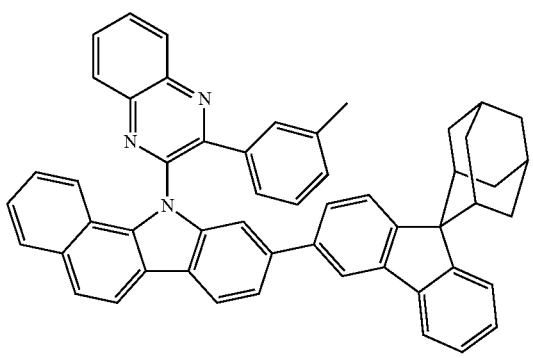
99
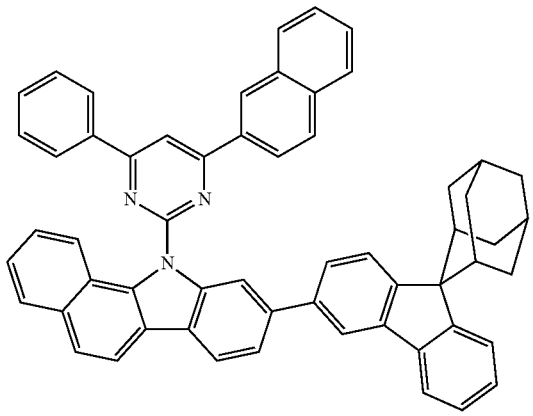

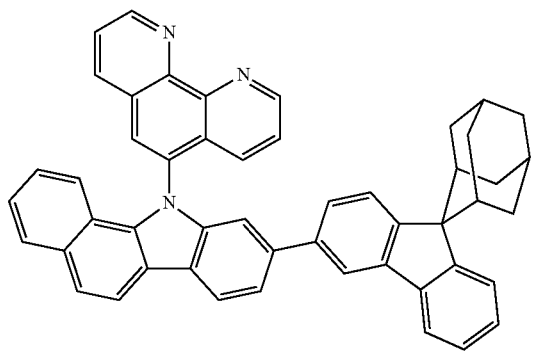
100
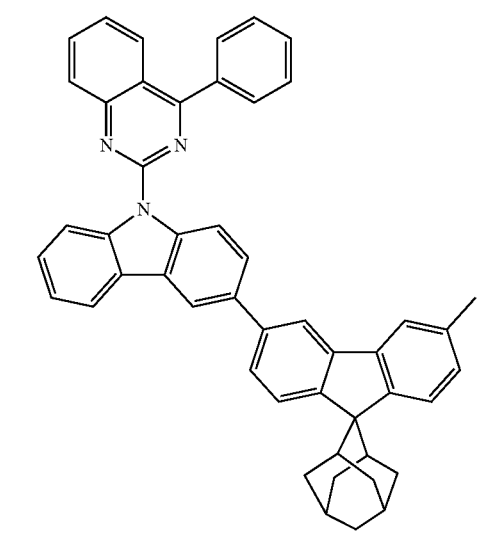
101
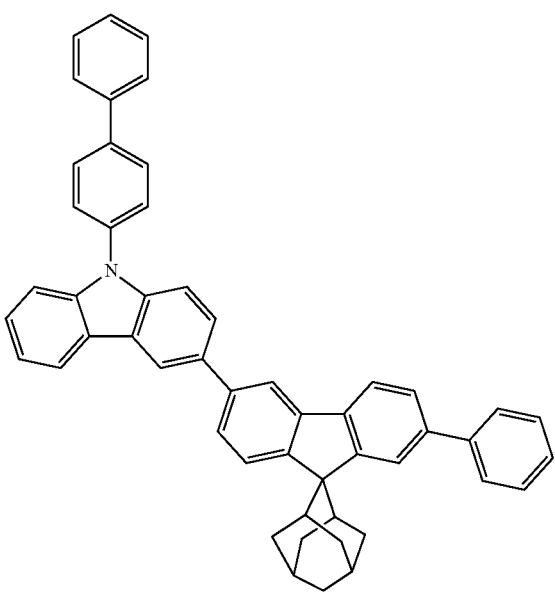
102
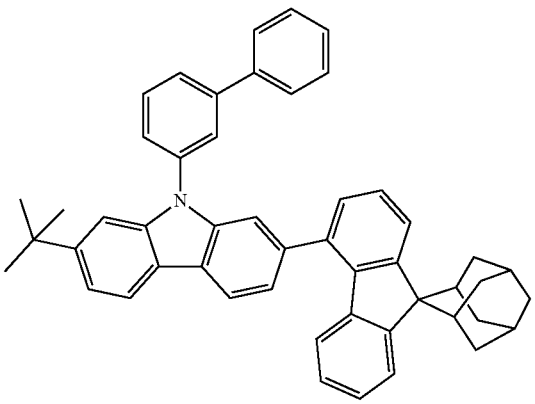
103
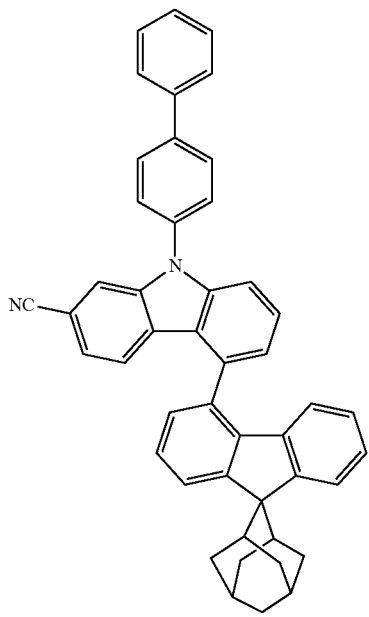
104
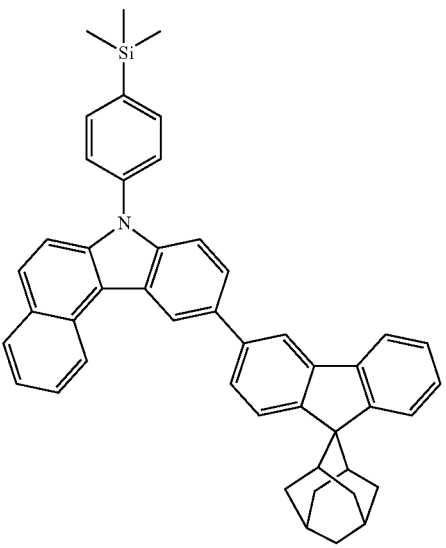
105

87
-continued
106
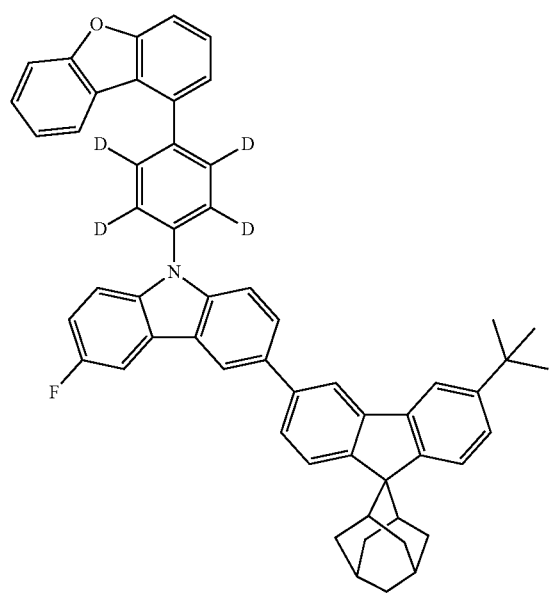
107
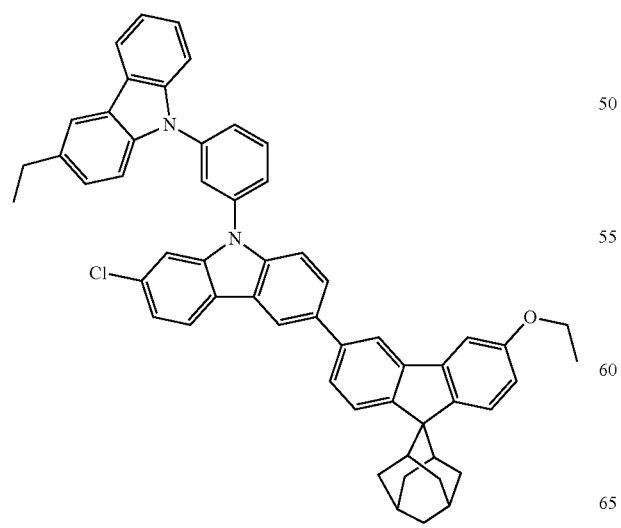
88
-continued
108
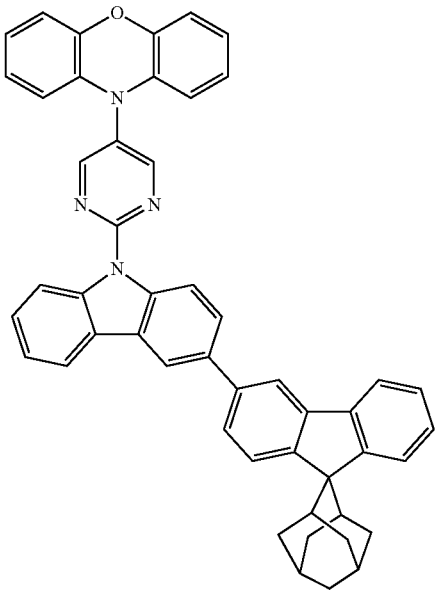
109
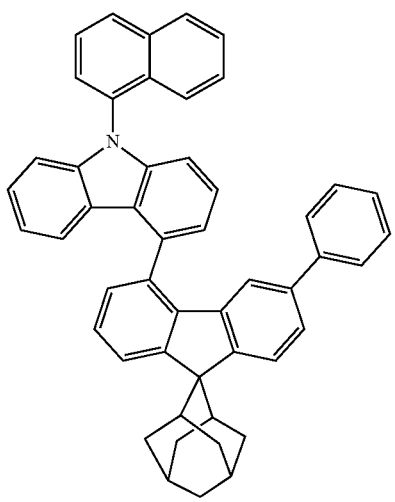

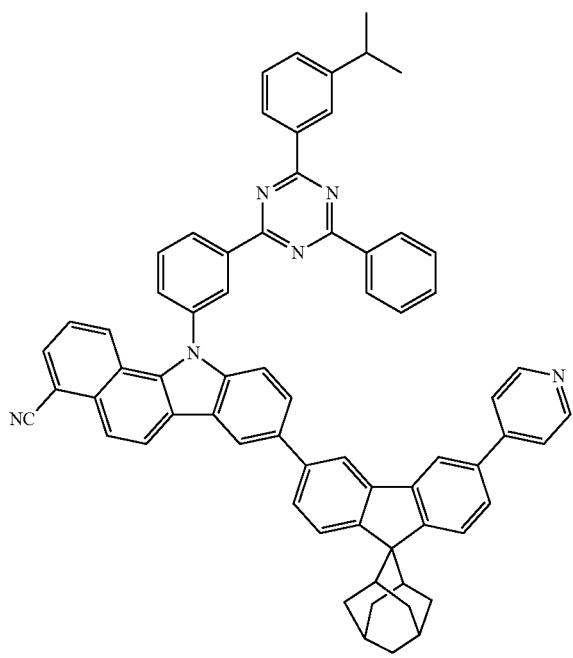
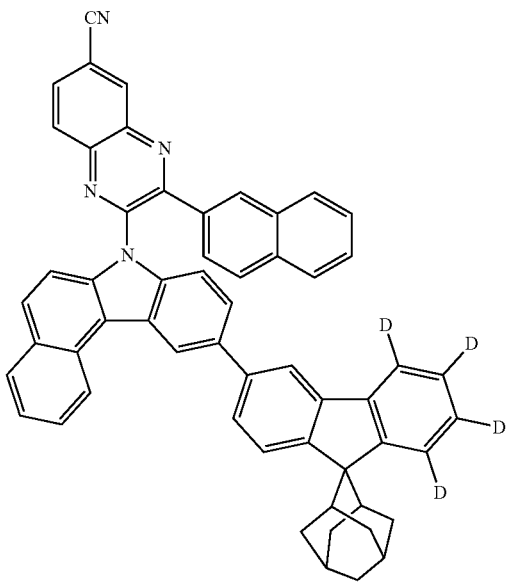

91
-continued
115
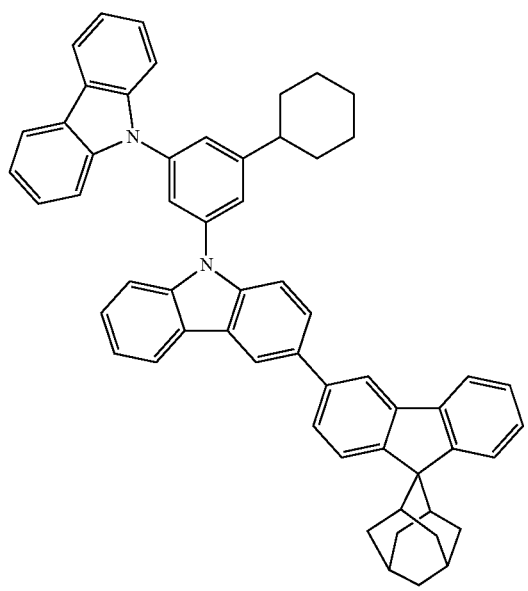
116
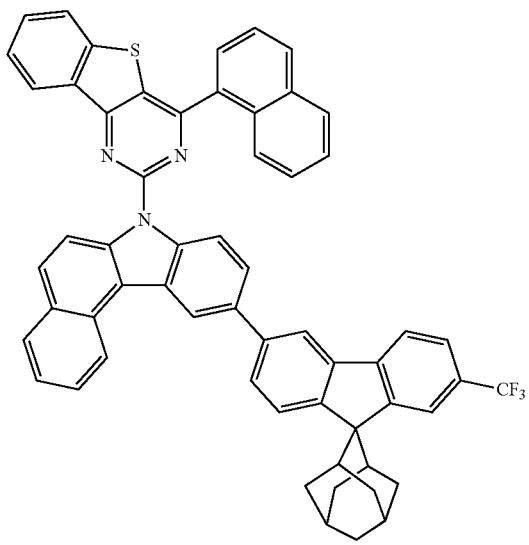
92
-continued
117
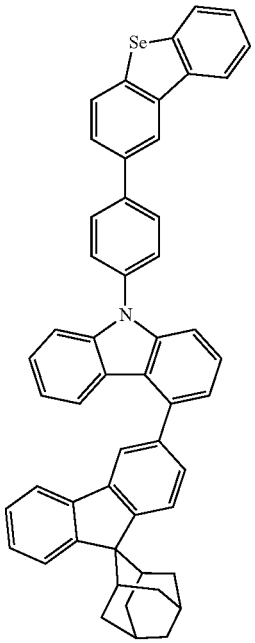
118
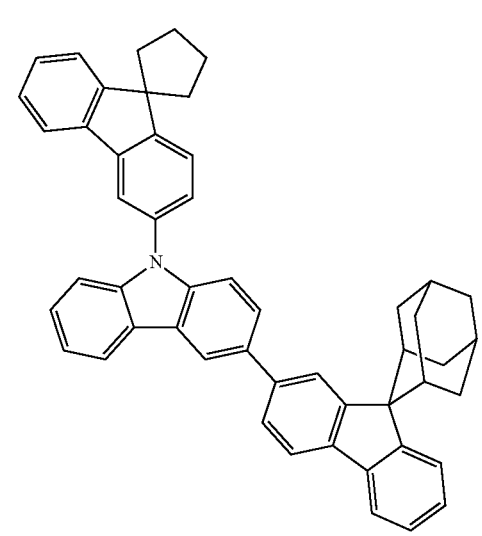

-continued
119
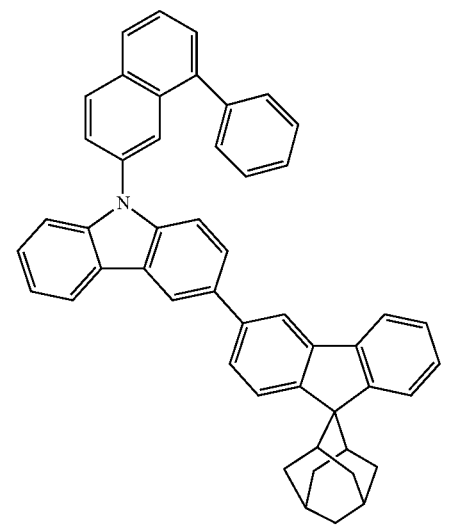
120
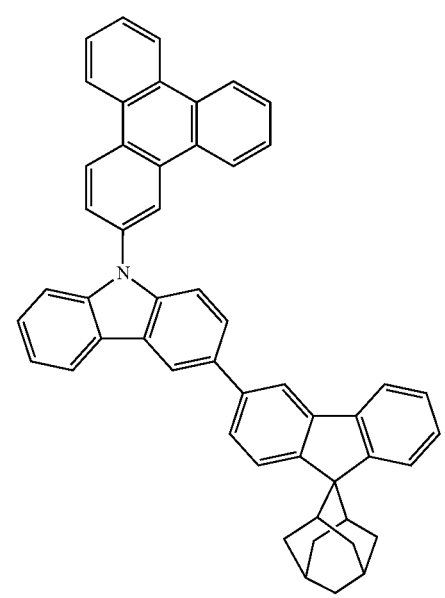
121
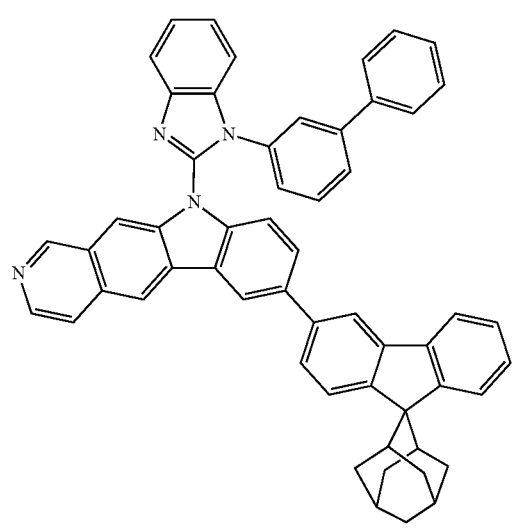
-continued
122
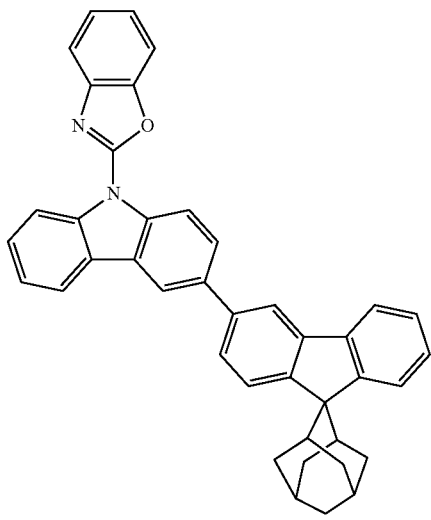
123
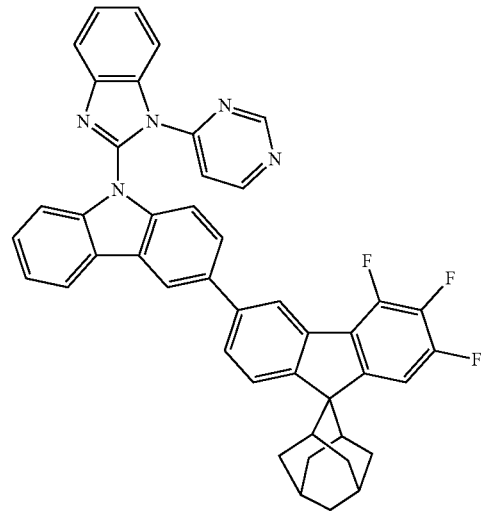
124
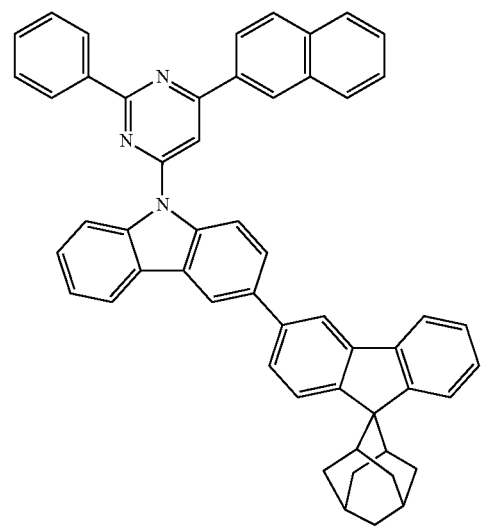

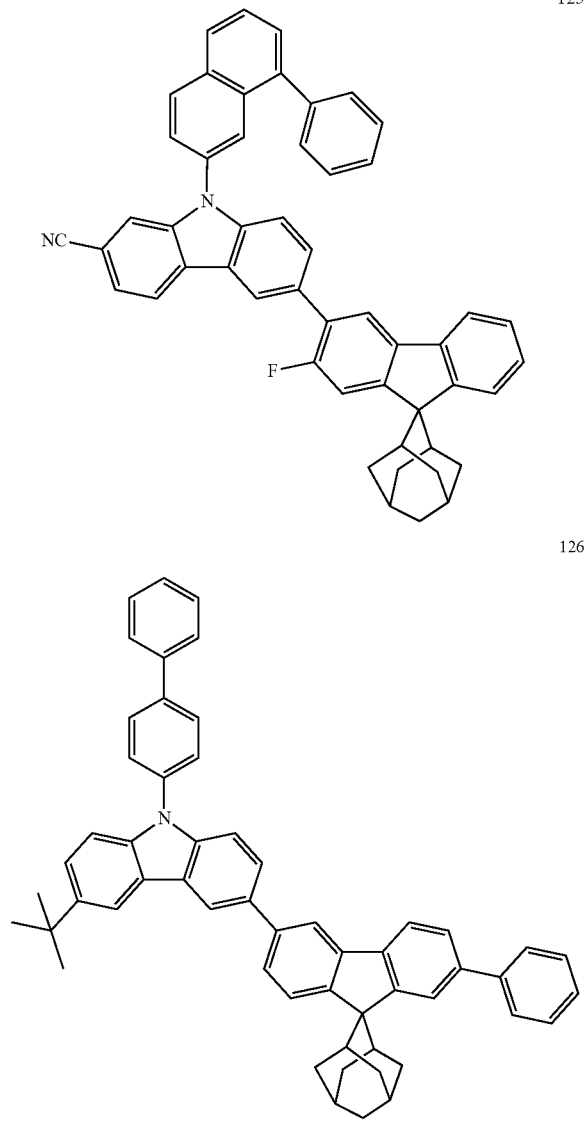
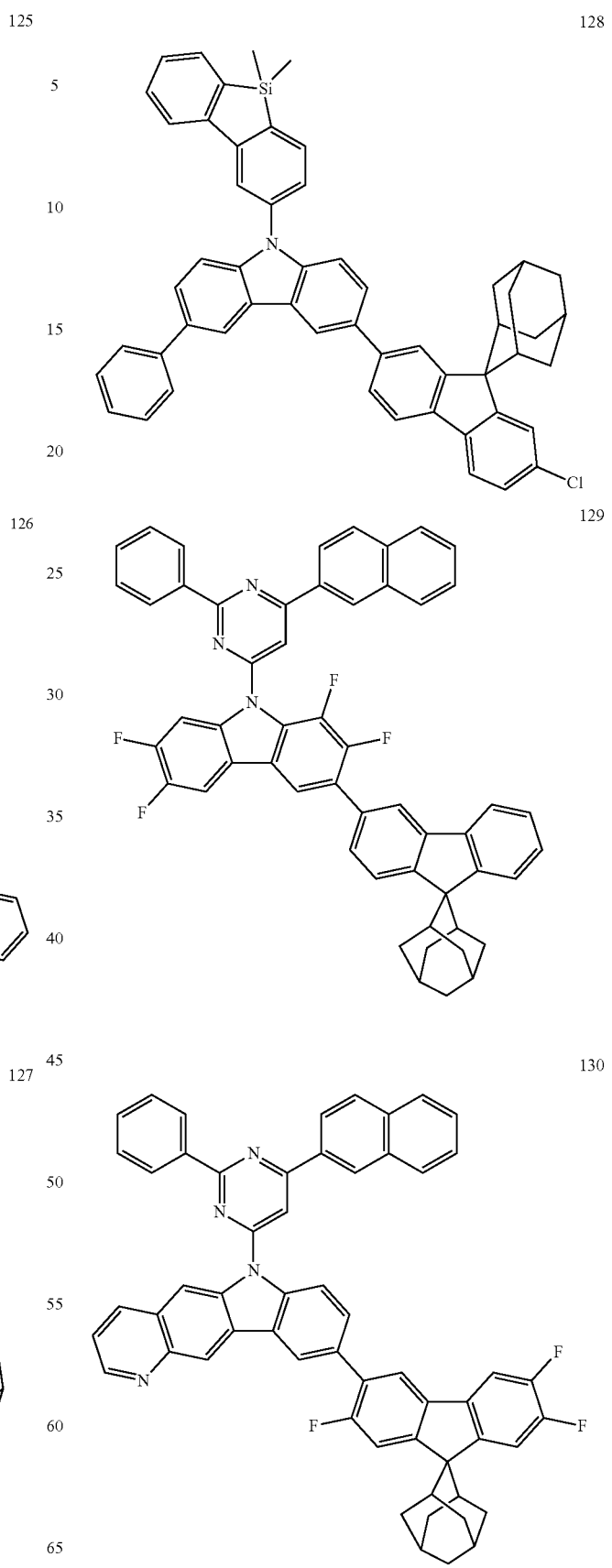

131
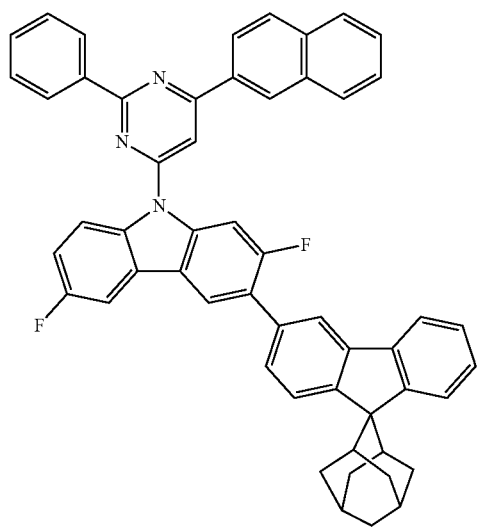
132
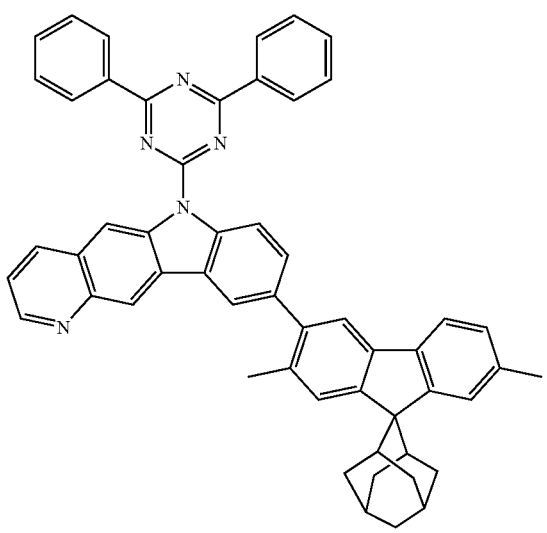
133
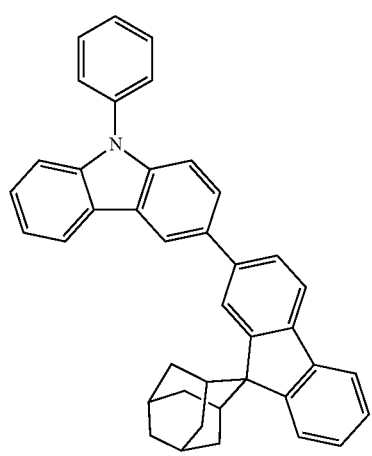
134
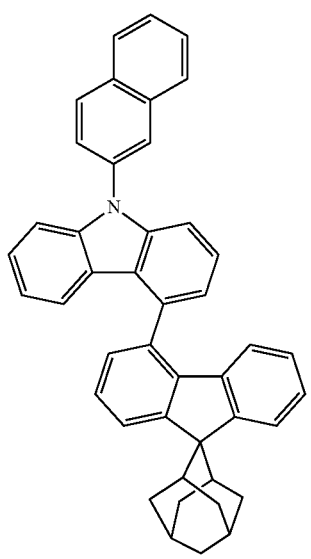
135
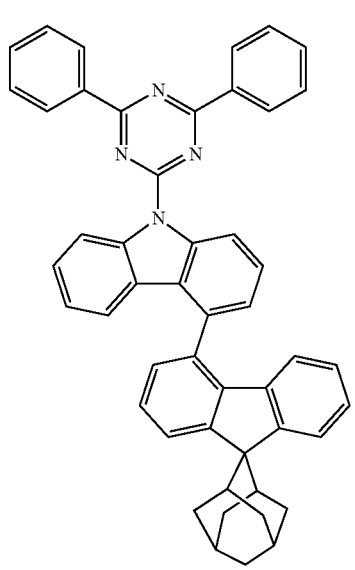
136
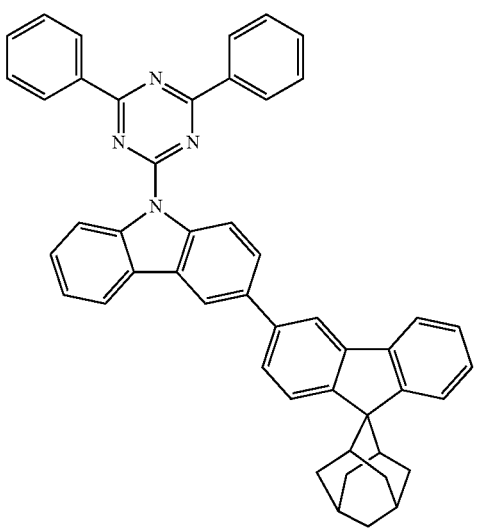

137 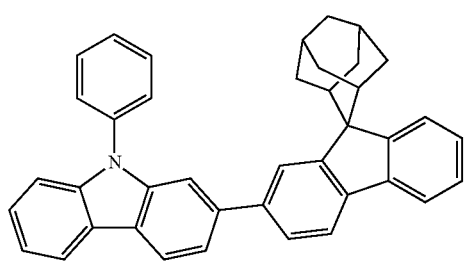
138 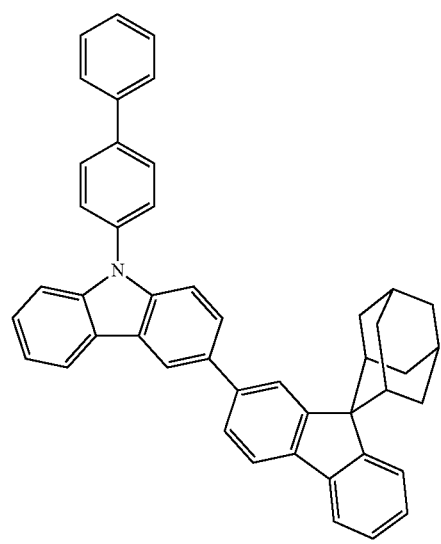
139 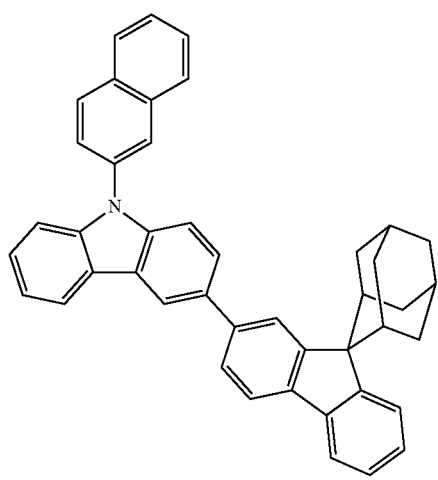
140 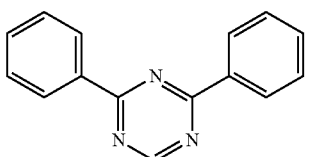 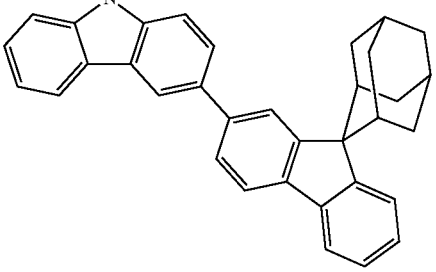
141 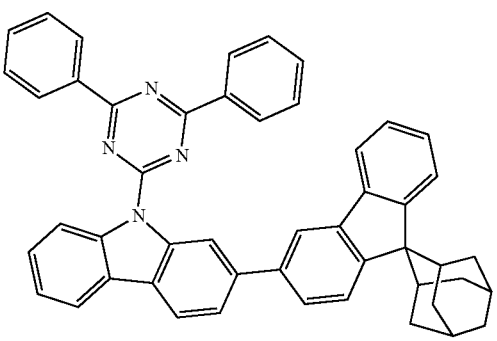
142 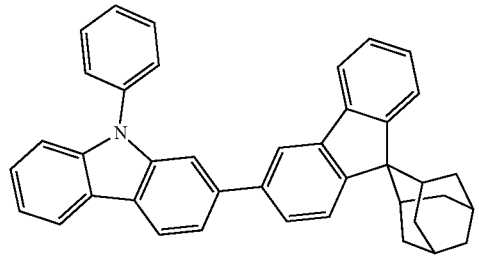
143 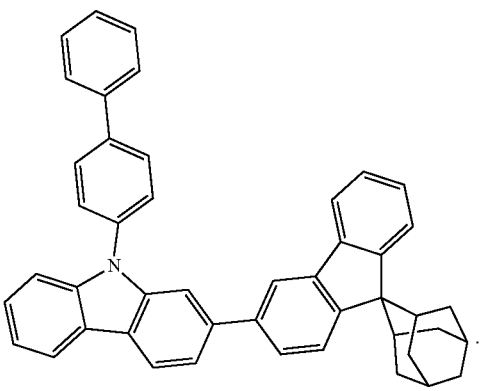
The present disclosure further provides an organic electroluminescent device, and the organic electroluminescent device includes an anode and a cathode disposed oppositely, and an organic light-emitting layer disposed between the anode and the cathode; and the organic light-emitting layer includes the above nitrogen-containing compound, thereby improving the voltage characteristic, efficiency characteristic and lifetime characteristic of the organic electroluminescent device.

For example, as shown in FIG. 1, the organic electroluminescent device may include an anode 100, a hole transport layer 321, an organic light-emitting layer 330, an electron transport layer 340 and a cathode 200 which are disposed in a stacking way successively. The nitrogen-containing compound provided by the present disclosure may be applied in the organic light-emitting layer 330 of the organic electroluminescent device to improve the lifetime of the organic luminescent device, increase the luminous efficiency of the organic luminescent device, or reduce the driving voltage of the organic luminescent device.

Optionally, the anode 100 includes an anode material, and is optionally a material which is conducive to the injection of holes into the functional layer and has a high work function (a work function). Specific examples of the anode material include, but not limited to, metals, such as, nickel, platinum, vanadium, chromium, copper, zinc, gold or alloys thereof, metal oxides, such as, zinc oxide, indium oxide, indium tin oxide (ITO) and Indium Zinc Oxide (IZO); combined metals and oxides, such as, $ZnO:Al$ or $SnO_2:Sb$; or conducting polymers, such as, poly(3-methylthiophene), poly[3,4-(ethylidene-1,2-dioxy)thiophene] (PEDT), polypyrrole and polyaniline. Optionally, a transparent electrode containing indium tin oxide (ITO) is included as the anode.

Optionally, the hole transport layer 321 may include one or more hole transport materials; the hole transport material may be selected from a carbazole multimer, a carbazole-connected tertiary aromatic amine compound or other types of compounds; there is no special limitation in the present disclosure.

Optionally, the organic light-emitting layer 330 may include a host material and an object material; holes injected into the organic light-emitting layer 330 and electrons injected into the organic light-emitting layer 330 may be composited in the organic light-emitting layer 330 to form excitons; excitons transfer energy to the host material, and the host material transfers energy to the object material, such that the object material may emit light.

In one embodiment of the present disclosure, the host material may consist of the nitrogen-containing compound of the present disclosure, especially consist of the nitrogen-containing compound including an electron-deficiency heteroaromatic ring on $Ar_1$. Such kind of nitrogen-containing compound may simultaneously transmit electrons and holes, and may balance the transmission efficiency between electrons and holes. Therefore, electrons and holes may be efficiently composited in the organic light-emitting layer to improve the luminous efficiency of the organic electroluminescent device.

In another embodiment of the present disclosure, the host material may be a composite material, for example, may include the nitrogen-containing compound of the present disclosure and a host material for the electron-type organic light-emitting layer. The nitrogen-containing compound of the present disclosure may effectively transmit holes, thus balancing the hole transmission efficiency and the electron transmission efficiency in the organic light-emitting layer. Therefore, electrons and holes may be efficiently composited in the organic light-emitting layer to improve the luminous efficiency of the organic electroluminescent device. For example, the host material may include the nitrogen-containing compound of the present disclosure and GH-n1.

The object material of the organic light-emitting layer 330 may be a compound having a condensed aryl ring or a derivative thereof, a compound having a heteroaryl ring or a derivative thereof, an aromatic amine derivative or other materials; there is no special limitation in the present disclosure. In one embodiment of the present disclosure, the object material of the organic light-emitting layer 330 may be $Ir(piq)_2(acac)$, and the like. In another embodiment of the present disclosure, the object material of the organic light-emitting layer 330 may be $Ir(ppy)_3$, and the like.

Optionally, the electron transport layer 340 may be a single-layered structure, and further a multi-layered structure, and may include one or more electron transport materials, the electron transport material may be selected from, but not limited to, benzimidazole derivatives, oxadiazole derivatives, quinoxaline derivatives, or other electron transport materials.

Optionally, the cathode 200 may include a cathode material, and is a material which is conducive to the injection of electrons into the functional layer and has a low work function. Specific examples of the cathode material include, but not limited to, Mg, Ca, Na, K, Ti, In, Y, $L_1$, Gd, Al, Ag, Sn and Pb or alloys thereof, or a multilayer material, such as, LiF/Al, Liq/Al, $LiO_2$/Al, LiF/Ca, LiF/Al and $BaF_2$/Ca. Optionally, the cathode material includes a metal electrode containing Al as a cathode. In one embodiment of the present disclosure, the cathode 200 may be made of silver-magnesium alloys.

Optionally, as shown in FIG. 1, a hole injection layer 310 may be further disposed between the anode 100 and the hole transport layer 321, thus enhancing the capacity of injecting holes into the first hole transport layer 321. The hole injection layer 310 may be selected from benzidine derivatives, starburst-shaped arylamine compounds, phthalocyanine derivatives, or other materials; there is no special limitation in the present disclosure. For example, the hole injection layer 310 may consist of $F_4$-TCNQ.

Optionally, as shown in FIG. 1, an electron barrier layer 322 may be further disposed between the hole transport layer 321 and the organic light-emitting layer 330, thus blocking the transmission of electrons towards the hole transport layer 321, thereby improving the recombination rate of electrons and holes in the organic light-emitting layer 330 and protecting the hole transport layer 321 from the impact of electrons. The electron barrier layer 322 may be made of carbazole multimers, carbazole-connected tertiary aromatic amine compounds or other feasible structures.

Optionally, as shown in FIG. 1, an electron injection layer 350 may be further disposed between the cathode 200 and the hole transport layer 340, thus enhancing the capacity of injecting electrons into the electron transport layer 340. The electron injection layer 350 may include alkali metal sulfides, alkali halides and other inorganic materials, or may include complexes of alkali metal and organics. For example, the electron injection layer 350 may include LiQ.

Figure 2:
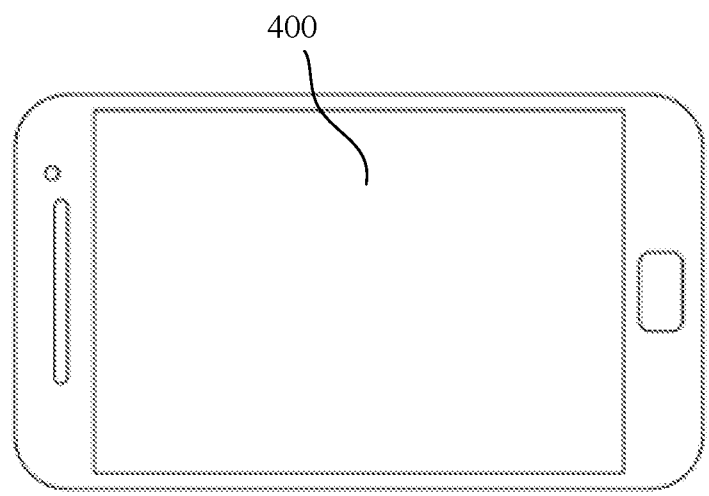
FIG. 2 is a structure diagram showing an electronic apparatus in an embodiment of the present disclosure.

The present disclosure further provides an electronic apparatus 400, as shown in FIG. 2, the electronic apparatus 400 includes any one of organic electroluminescent devices described in the above embodiments of the organic electroluminescent device. The electronic apparatus 400 may be a display apparatus, illuminating apparatus, optical communication apparatus, or other types of electronic apparatus, for example, may include, but not limited to, a computer screen, mobile phone screen, television, an electronic paper, emergency lamp, optical module, and the like. Since the electronic apparatus 400 has any one of organic electroluminescent devices described in the above embodiments of the organic electroluminescent device, the electronic apparatus 400 has the same beneficial effect, which will be not described any more here.

Synthesis Examples

For the synthesis examples described below, unless otherwise specified, all the temperature have a unit of degree centigrade. Partial reagents are purchased from commodity suppliers, such as, Aldrich Chemical Company, Arco Chemical Company and Alfa Chemical Company. There is no further purification step in use process, unless otherwise specified. The rest common reagents are purchased from Shantou Xilong Chemical Plant, Guangdong Guanghua Chemical Reagent Factory, Guangzhou Chemical Reagent Factory, Tianjin Haoyuyu Chemicals Co., Ltd., Tianjin Fuchen Chemical Reagent Factory, Wuhan Xinhuayuan Science& Technology Development Co., Ltd., Qingdao Tenglong Chemicals Co., Ltd., and Qingdao Marine Chemical Plant. Anhydrous tetrahydrofuran, dioxane, methylbenzene, diethyl ether and other anhydrous solvents are obtained by performing reflux and drying with metal sodium. Anhydrous dichloromethane and chloroform are obtained by performing reflux and drying with calcium hydride. Ethyl acetate, petroleum ether, n-hexane, N,N-dimethylacetamide and N,N-dimethylformamide are dried by anhydrous sodium sulfate in advance before use.

The reaction in each synthesis example is generally performed under a positive pressure of nitrogen or argon, or by sleeving a dry tube on an anhydrous solvent (unless otherwise specified); the reaction flask is plugged with a suitable rubber plug in the reaction, and substrate is pumped via an injector. All the glassware used herein have been dried.

A silicagel column is used as a chromatographic column during purification. Silicagel (300~400-mesh) is purchased from Qingdao Marine Chemical Plant.

In each synthesis example, determination conditions of low-resolution mass spectrum (MS) data are as follows: Agilent 6120 quadrupole HPLC-M (column model: Zorbax SB-C18, 2.1×30 mm, 3.5 μm, 6 min, flow rate: 0.6 mL/min. Mobile phase: 5%~95%, a ratio of (acetonitrile containing 0.1% formic acid) in ($H_2O$ containing 0.1% formic acid); electrospray ionization (ESI) is used and UV detection is performed under 210 nm/254 nm.

The target compound is detected by Agilent 1260pre-HPLC or Calesep pump 250pre-HPLC (column model: NOVASEP 50/80 mm DAC) via UV at 210 nm/254 nm.

$^1$HNMR: Bruker 400 MHz NMR equipment, $CDCl_3$ or $CD_2Cl_2$ serves as a solvent (unit: ppm) at room temperature, and TMS (0 ppm) serves as a reference standard. In case of multiplet, the following abbreviation will be used: singlet (s), doublet (d), triplet (t) and multiplet (m).

The compound of the present disclosure is synthesized by the following method:

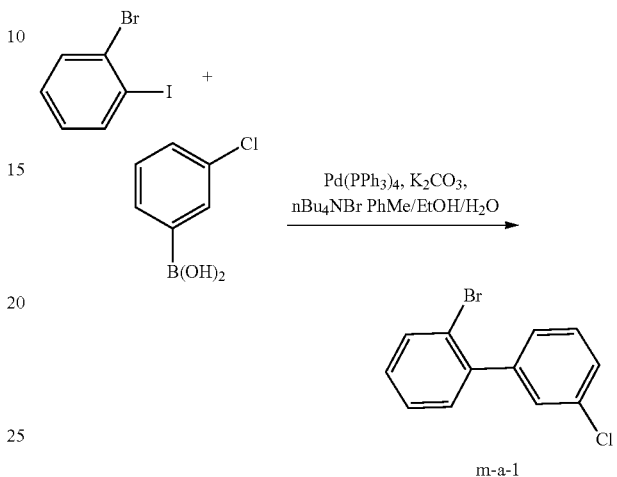

2-bromoiodobenzene (30.0 g, 106.0 mmol), 3-chlorophenylboronic acid (18.2 g, 116.6 mmol), tetra(triphenylphosphine) palladium (2.5 g, 2.1 mmol), potassium carbonate (36.6 g, 265.1 mmol), and tetrabutylammonium bromide (6.8 g, 21.2 mmol) were added to a flask, then a mixed solvent of methylbenzene (240 mL), ethanol (60 mL), and water (60 mL) was added. The reaction mixture was warmed to 80° C. under nitrogen atmosphere and stirred for 8 h at the constant temperature, then cooled to room temperature, and stirring was stopped. The reaction solution was washed with water and the separated organic phase was dried over anhydrous $MgSO_4$ and filtered. The filtrate was concentrated in a vacuo to obtain a crude product. The crude product was purified by silica gel column chromatography and eluted with n-heptane to obtain intermediate m-a-1 as a light grey solid (22.3 g, yield 79%).

Intermediates m-b-1 and m-c-1 were synthesized by replacing the 3-chlorophenylboronic acid with the compound as shown in the reactant A in Table 1 based on the synthesis method similar to the intermediate m-a-1:

TABLE 1 synthesis of the intermediates m-b-1 and m-c-1

| Intermediate No. | Reactant A | Structure | Yield (%) |
|---|---|---|---|
| m-b-1 | (HO)$_2$B—⌬—Cl | Br—⌬—⌬—Cl | 80% |
| m-c-1 | (HO)$_2$B—⌬—Cl | Br—⌬—⌬—Cl | 66% |

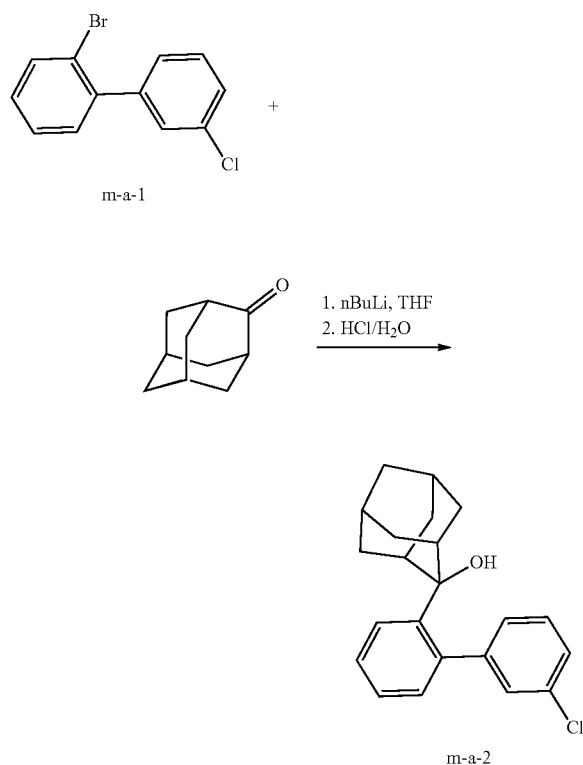

The intermediate m-a-1 (22.3 g, 83.3 mmol) and tetrahydrofuran (150 ml) were added to a flask and cooled to −78° C. under nitrogen atmosphere; a solution of n-butyllithium in tetrahydrofuran (2.5M, 50 mL, 125.0 mmol) was slowly added dropwise under stirring, after dropwise addition, the solution was thermally insulated and stirred for 1 h. A solution of adamantanone (10.0 g, 66.7 mmol) in tetrahydrofuran (50 mL) was added to the reaction mixture, after dropwise addition, the obtained solution was thermally insulated for 0.5 h and warmed to room temperature, and stirred for another 12 h. Then a solution of hydrochloric acid (12M, 13.9 mL, 166.7 mmol) in water (60 mL) was added to the reaction solution and the resulting mixture was stirred for 1 h; then dichloromethane (100 mL) was added to the reaction mixture for extraction. The separated organic phase was washed with water to be neutral, and then dried over anhydrous magnesium sulfate, filtered. The filtrate was concentrated in a vacuo to obtain a crude product. The crude product was purified by silica gel column chromatography and eluted with a mixture of dichloromethane and n-heptane to obtain intermediate m-a-2 as a colorless oil (16.5 g, yield 73%).

Intermediates m-b-2 and m-c-2 were synthesized by replacing the intermediate m-a-1 with the reactant B as shown in Table 2 based on the synthesis method similar to the intermediate m-a-2:

TABLE 2

| synthesis of the intermediates m-b-2 and m-c-2 | | | |
|---|---|---|---|
| Intermediate No. | Reactant B | Structure | Yield (%) |
| m-b-2 | ![Br-biphenyl-Cl] | ![adamantane-OH-biphenyl-Cl] | 77% |
| m-c-2 | ![Br-biphenyl-Cl] | ![adamantane-OH-biphenyl-Cl] | 69% |

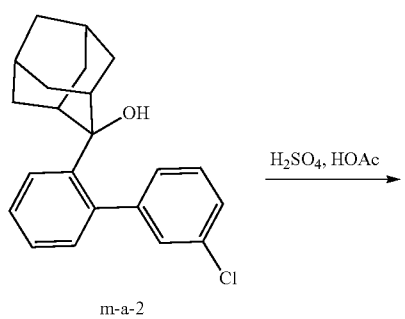

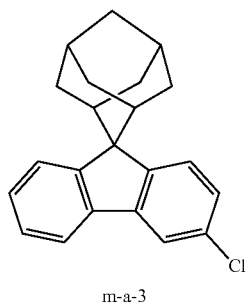

The intermediate m-a-2 (16.5 g, 48.7 mmol) and glacial acetic acid (200 mL) were added to a flask. The mixture was stirred and a solution of concentrated sulfuric acid (98%, 0.3 mL, 4.9 mmol) in acetic acid (10 mL) was added dropwise slowly under nitrogen atmosphere. After dropwise addition, the reaction mixture was warmed to 70° C. and stirred for 1 h, and then cooled to room temperature, some precipitate appeared. Filtered, and then the filter cake was eluted with water and ethanol. Collected the filter cake and dried in a vacuo to obtain a crude product. The crude product was purified by silica gel column chromatography and eluted with a mixture of n-heptane and dichloromethane to obtain intermediate m-a-3 as a white solid (7.4 g, yield 47%).

Intermediates m-b-3 and m-c-3 were synthesized by replacing the intermediate m-a-2 with the reactant C as shown in Table 3 based on the synthesis method similar to the intermediate m-a-3:

TABLE 3

| synthesis of the intermediates m-b-3 and m-c-3 | | | |
|---|---|---|---|
| Intermediate No. | Reactant C | Structure | Yield (%) |
| m-b-3 | ![reactant] | ![structure] | 90 |
| m-c-3 | ![reactant] | ![structure] | 77 |

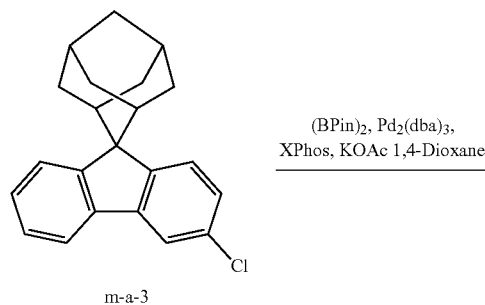

The intermediate m-a-3 (7.4 g, 23.1 mmol), pinacol diborate (7.0 g, 27.7 mmol), tri(dibenzalacetone) dipalladium (0.2 g, 0.2 mmol), 2-bicyclohexyl phosphorus-2',4',6'-triisopropyl biphenyl (0.2 g, 0.5 mmol), potassium acetate (4.5 g, 46.1 mmol) and 1,4-dioxane (50 mL) were added to a flask, and the reaction mixture was heated to reflux at 100° C. and stirred for 8 h under nitrogen atmosphere. The resulting mixture was cooled to room temperature; and then a mixture of dichloromethane and water was added to the mixture for extraction. The separated organic phase was wasted with water and dried over anhydrous magnesium sulfate, and then concentrated in a vacuo to obtain a crude product. The crude product was purified by silica gel column chromatography and eluted with a mixture of ethyl acetate and n-heptane to obtain the intermediate m-a-4 as a white solid (7.9 g, yield 83%).

Intermediates m-b-4 and m-c-4 were synthesized by replacing the intermediate m-a-3 with the reactant D as shown in Table 4 based on the synthesis method similar to the intermediate m-a-4:

TABLE 4 synthesis of the intermediates m-b-4 and m-c-4

| Intermediate No. | Reactant D | Structure | Yield (%) |
|---|---|---|---|
| m-b-4 | (structure) | (structure) | 80 |
| m-c-4 | (structure) | (structure) | 71 |

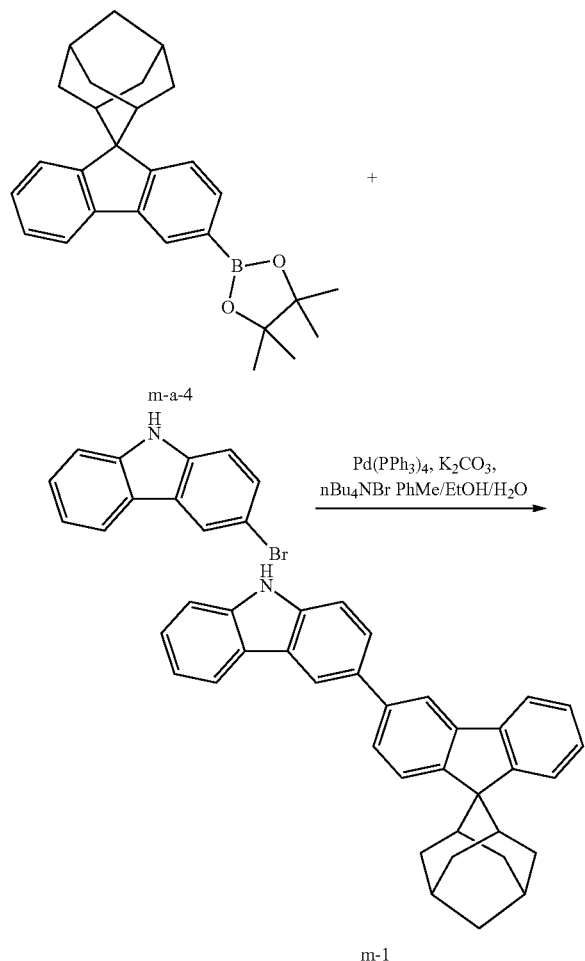

Intermediates m-a-4 (7.9 g, 19.2 mmol), 3-bromocarbazole (5.0 g, 20.1 mmol), tetra(triphenylphosphine) palladium (0.4 g, 0.4 mmol), potassium carbonate (6.6 g, 47.9 mmol), and tetrabutylammonium bromide (1.2 g, 3.8 mmol) were added to a flask, then a mixed solvent of methylbenzene (80 mL), ethanol (20 mL), and water (20 mL) was added, and the resulted mixture was warmed to 80° C. under nitrogen atmosphere and stirred for 12 h at the constant temperature. Then the reaction mixture was cooled to room temperature, and stopped stirring. The resulted mixture was washed with water and the separated organic phase was separated and dried over anhydrous $MgSO_4$; and then concentrated in a vacuo to obtain a crude product. The crude product was purified by silica gel column chromatography and eluted with a mixture of dichloromethane and n-heptane to obtain the intermediate m-1 as a white solid (7.0 g, yield 81%).

Intermediates m-2 to m-12 were synthesized by replacing the intermediate m-a-4 with the reactant E as shown in Table 5, replacing 3-bromocarbazole with the reactant F as shown in Table 5 based on the synthesis method similar to the intermediate m-1:

Table 5: synthesis of the intermediates m-2 to m-12

TABLE 5

| Intermediate No. | Reactant E | Reactant F | Structure | Yield (%) |
|---|---|---|---|---|
| m-2 | | | 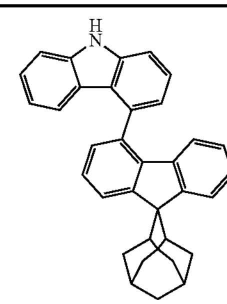 | 51 |
| m-3 | | | 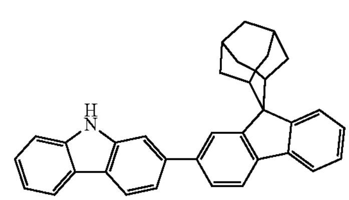 [SMILES: c1ccc2c(c1)-c1ccc(-c3ccc4c(c3)[nH]c3ccccc34)cc1C21C2CC3CC4CC1C2(C3)C4] | 88 |

TABLE 5-continued synthesis of the intermediates m-2 to m-12

| Intermediate No. | Reactant E | Reactant F | Structure | Yield (%) |
|---|---|---|---|---|
| m-4 | | | 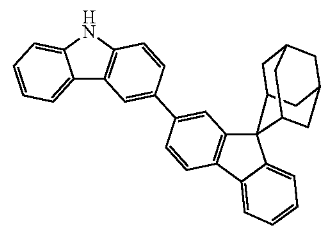 [SMILES: c1ccc2c(c1)-c1ccc(-c3ccc4[nH]c5ccccc5c4c3)cc1C21C2CC3CC(C2)CC1C3] | 85 |
| m-5 | | | 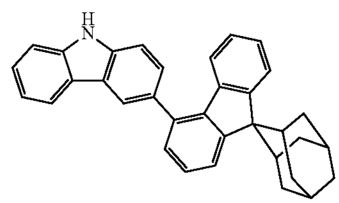 [SMILES: c1ccc2c(c1)-c1c(-c3ccc4[nH]c5ccccc5c4c3)cccc1C21C2CC3CC(C2)CC1C3] | 63 |
| m-6 | | | 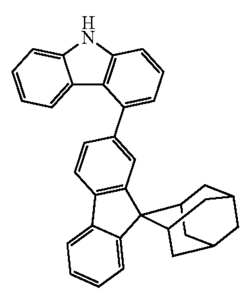 [SMILES: c1ccc2c(c1)-c1ccc(-c3cccc4[nH]c5ccccc5c34)cc1C21C2CC3CC(C2)CC1C3] | 74 |

TABLE 5-continued synthesis of the intermediates m-2 to m-12

| Intermediate No. | Reactant E | Reactant F | Structure | Yield (%) |
|---|---|---|---|---|
| m-7 | | | 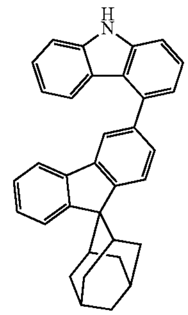 [SMILES: c1ccc2c(c1)-c1cc(-c3cccc4[nH]c5ccccc5c34)ccc1C21C2CC3CC(C2)CC1C3] | 61 |
| m-8 | | | 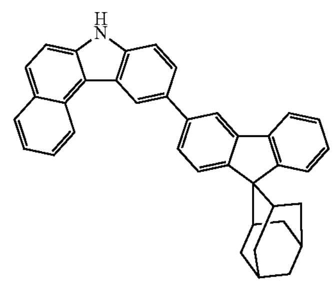 [SMILES: c1ccc2c(c1)-c1cc(-c3ccc4[nH]c5ccc6ccccc6c5c4c3)ccc1C21C2CC3CC(C2)CC1C3] | 79 |
| m-9 | | | 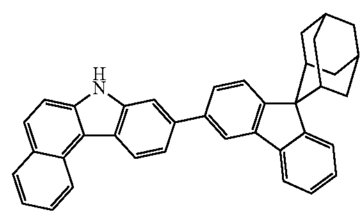 [SMILES: c1ccc2c(c1)-c1cc(-c3ccc4c(c3)[nH]c3ccc5ccccc5c34)ccc1C21C2CC3CC(C2)CC1C3] | 80 |
| m-10 | | | 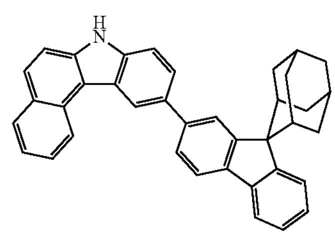 [SMILES: c1ccc2c(c1)-c1ccc(-c3ccc4[nH]c5ccc6ccccc6c5c4c3)cc1C21C2CC3CC(C2)CC1C3] | 62 |

TABLE 5-continued
synthesis of the intermediates m-2 to m-12
| Intermediate No. | Reactant E | Reactant F | Structure | Yield (%) |
|---|---|---|---|---|
| m-11 | | | 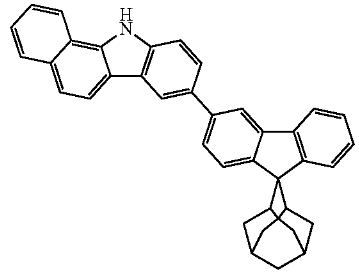 [SMILES: c1ccc2c(c1)-c1cc(-c3ccc4[nH]c5c6ccccc6ccc5c4c3)ccc1C21C2CC3CC4CC1C2(C3)C4] | 70 |
| m-12 | | | 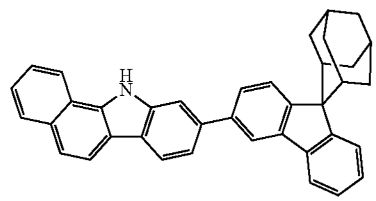 [SMILES: c1ccc2c(c1)-c1cc(-c3ccc4c(c3)[nH]c3c5ccccc5ccc43)ccc1C21C2CC3CC(C2)CC1C3] | 82 |
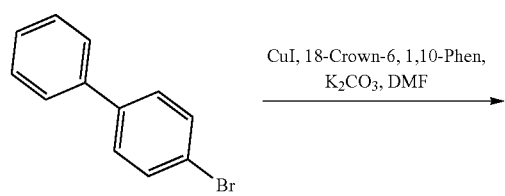
The intermediate m-1 (7.0 g, 15.5 mmol), 4-bromobiphenyl (4.3 g, 18.6 mmol), cuprous iodide (0.6 g, 3.1 mmol), potassium carbonate (4.7 g, 34.1 mmol), 1,10-phenanthroline (1.1 g, 6.2 mmol), 18-crown-6-ether (04 g, 1.6 mmol) and dimethylformamide (40 mL) were added to a flask, and the mixture was warmed to 145° C. under nitrogen astrosphere and stirred for 8 h. The resulting mixture was cooled to room temperature; and then a mixture of dichloromethane (80 mL) and water (100 mL) was added to the reaction mixture for extraction. The separated organic phase was wasted with water and dried over anhydrous magnesium sulfate, and then concentrated in a vacuo to obtain a residue. The residue was purified by silica gel column chromatography and eluted with a mixture of dichloromethane and n-heptane to obtain the crude product. Then, the crude product was purified by recrystallization using a mixture of dichloromethane and ethyl acetate, to obtain compound 2 as a white solid (4.4 g, yield 47%).

Compounds as shown in Table 6 were synthesized by replacing the intermediate m-1 with the reactant G as shown in Table 6, replacing 4-bromobiphenyl with the reactant H as shown in Table 6 based on the synthesis method similar to the compound 2:

TABLE 6 structures and raw materials of partial compounds

| Compound No. | Reactant G | Reactant H | Structure | Yield (%) |
|---|---|---|---|---|
| 10 | | | 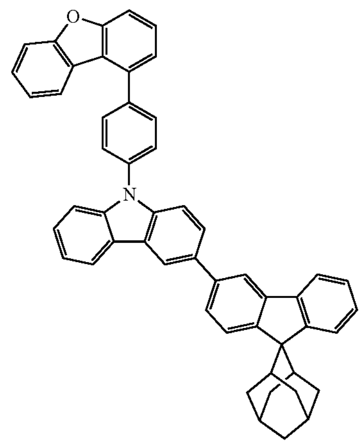 [SMILES: c1ccc2c(c1)-c1cc(-c3ccc4c(c3)c3ccccc3n4-c3ccc(-c4cccc5oc6ccccc6c45)cc3)ccc1C21C2CC3CC(C2)CC1C3] | 58 |
| 13 | | | 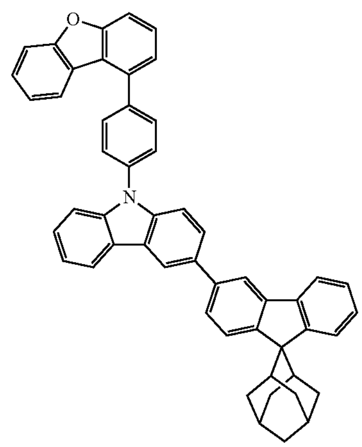 [SMILES: c1ccc2c(c1)-c1cc(-c3ccc4c(c3)c3ccccc3n4-c3ccc(-c4cccc5oc6ccccc6c45)cc3)ccc1C21C2CC3CC(C2)CC1C3] | 62 |
| 22 | | | 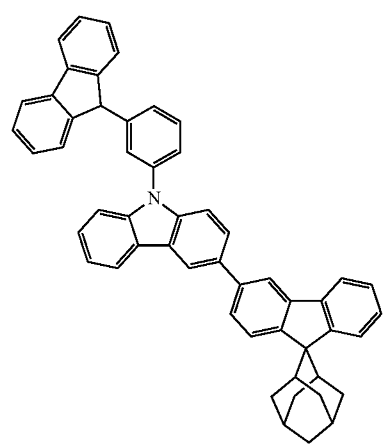 [SMILES: c1cc(C2c3ccccc3-c3ccccc32)cc(-n2c3ccccc3c3cc(-c4ccc5c(c4)-c4ccccc4C54C5CC6CC(C5)CC4C6)ccc32)c1] | 34 |

TABLE 6-continued
structures and raw materials of partial compounds
| Compound No. | Reactant G | Reactant H | Structure | Yield (%) |
|---|---|---|---|---|
| 30 | 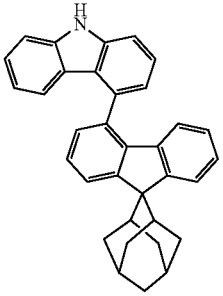 | 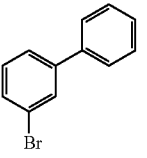 [SMILES: Brc1cccc(-c2ccccc2)c1] | 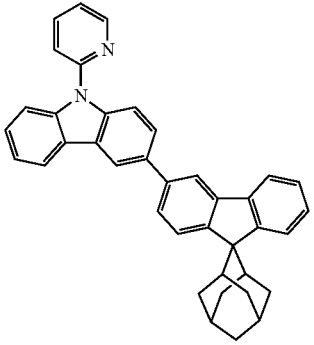 [SMILES: c1ccc(-n2c3ccccc3c3cc(-c4ccc5c(c4)-c4ccccc4C54C5CC6CC(C5)CC4C6)ccc32)nc1] | 70 |
| 32 | 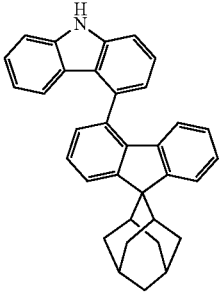 | 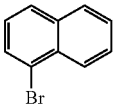 | 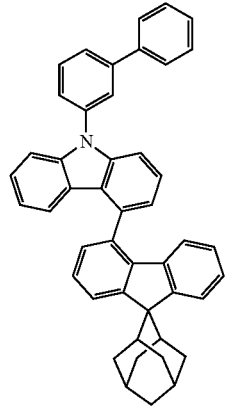 [SMILES: c1ccc(-c2cccc(-n3c4ccccc4c4c(-c5cccc6c5-c5ccccc5C65C6CC7CC(C6)CC5C7)cccc43)c2)cc1] | 55 |
| 36 | 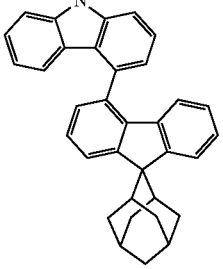 | 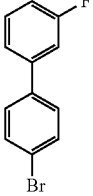 | 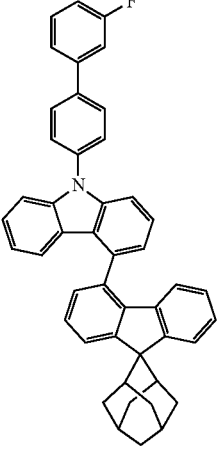 | 49 |
| 40 | 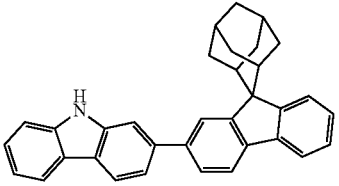 [SMILES: c1ccc2c(c1)-c1ccc(-c3ccc4c(c3)[nH]c3ccccc34)cc1C21C2CC3CC(C2)CC1C3] | 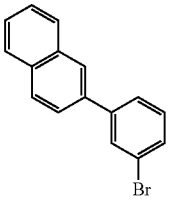 [SMILES: Brc1cccc(-c2ccc3ccccc3c2)c1] | 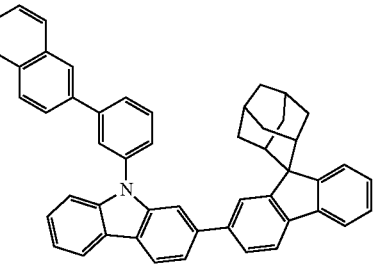 | 69 |

TABLE 6-continued
structures and raw materials of partial compounds
| Compound No. | Reactant G | Reactant H | Structure | Yield (%) |
|---|---|---|---|---|
| 47 | 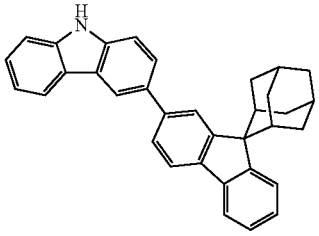 [SMILES: c1ccc2c(c1)-c1ccc(-c3ccc4[nH]c5ccccc5c4c3)cc1C21C2CC3CC(C2)CC1C3] | 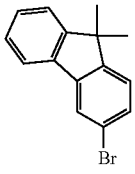 [SMILES: CC1(C)c2ccccc2-c2cc(Br)ccc21] | 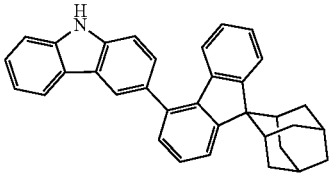 [SMILES: c1ccc2c(c1)-c1c(-c3ccc4[nH]c5ccccc5c4c3)cccc1C21C2CC3CC(C2)CC1C3] | 73 |
| 51 |  | 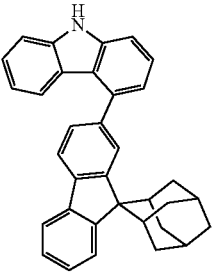 [SMILES: c1ccc2c(c1)-c1ccc(-c3cccc4[nH]c5ccccc5c34)cc1C21C2CC3CC(C2)CC1C3] | 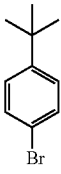 | 40 |
| 54 |  |  | 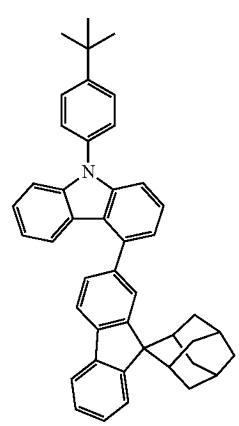 [SMILES: CC(C)(C)c1ccc(-n2c3ccccc3c3c(-c4ccc5c(c4)C4(c6ccccc6-5)C5CC6CC(C5)CC4C6)cccc32)cc1] | 51 |

TABLE 6-continued
structures and raw materials of partial compounds
| Compound No. | Reactant G | Reactant H | Structure | Yield (%) |
|---|---|---|---|---|
| 58 | 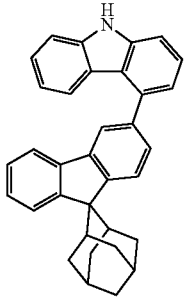 [SMILES: c1ccc2c(c1)-c1cc(-c3cccc4[nH]c5ccccc5c34)ccc1C21C2CC3CC(C2)CC1C3] | 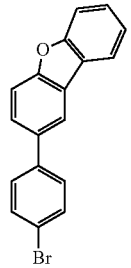 [SMILES: Brc1ccc(-c2ccc3oc4ccccc4c3c2)cc1] | 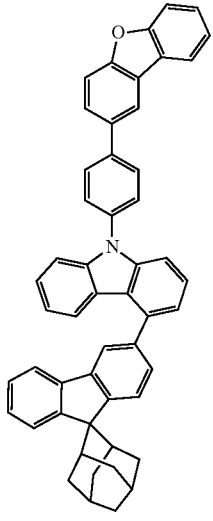 [SMILES: c1ccc2c(c1)-c1cc(-c3cccc4c3c3ccccc3n4-c3ccc(-c4ccc5oc6ccccc6c5c4)cc3)ccc1C21C2CC3CC(C2)CC1C3] | 61 |
| 79 | 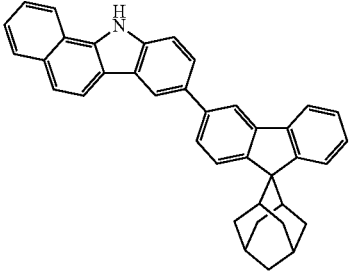 [SMILES: c1ccc2c(c1)-c1cc(-c3ccc4[nH]c5c6ccccc6ccc5c4c3)ccc1C21C2CC3CC(C2)CC1C3] | 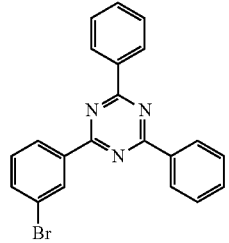 [SMILES: Brc1cccc(-c2nc(-c3ccccc3)nc(-c3ccccc3)n2)c1] | 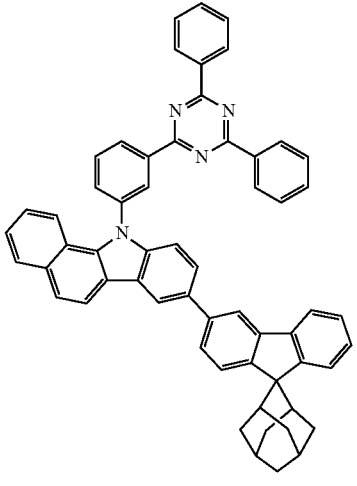 [SMILES: c1ccc(-c2nc(-c3ccccc3)nc(-c3cccc(-n4c5ccc(-c6ccc7c(c6)-c6ccccc6C76C7CC8CC(C7)CC6C8)cc5c5ccc6ccccc6c54)c3)n2)cc1] | 42 |
| 100 | 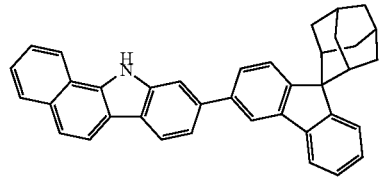 | 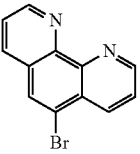 [SMILES: Brc1cc2cccnc2c2ncccc12] | 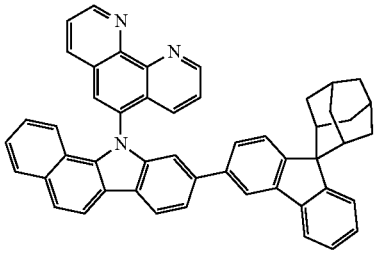 [SMILES: c1ccc2c(c1)-c1cc(-c3ccc4c5ccc6ccccc6c5n(-c5cc6cccnc6c6ncccc56)c4c3)ccc1C21C2CC3CC(C2)CC1C3] | 29 |

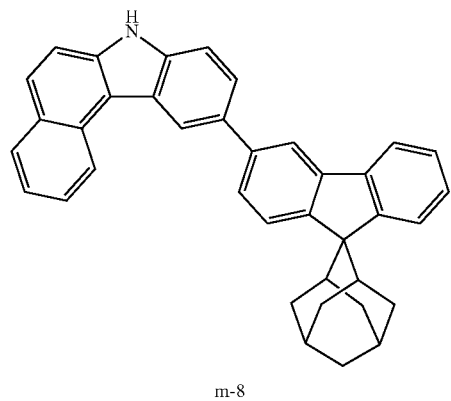

m-8

+

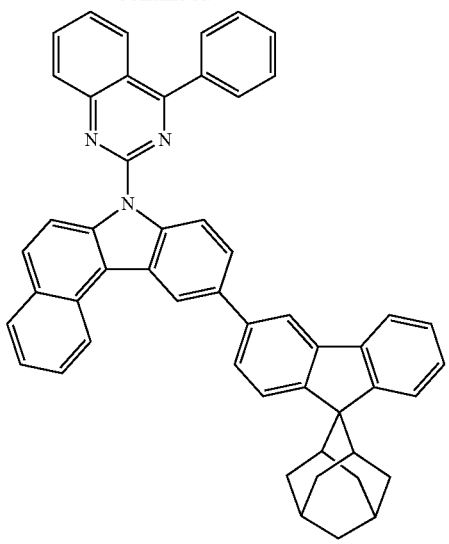

64

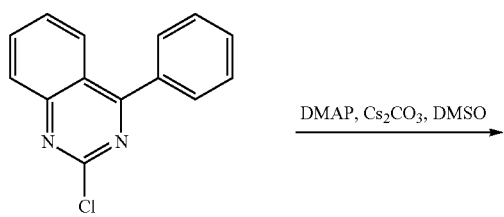

DMAP, Cs₂CO₃, DMSO →

The intermediate m-8 (8.4 g, 16.7 mmol), 2-chloro-4-phenylquinazoline (4.4 g, 18.4 mmol), 4-dimethylamino-pyridine (1.0 g, 8.4 mmol), cesium carbonate (5.5 g, 16.7 mmol) and dimethyl sulfoxide (100 mL) were added to a round-bottom flask, and the reaction mixture was warmed to 100° C. and stirred for 12 h. The resulting mixture was cooled to room temperature; filtered, and the filter cake was eluted with water ethanol, and dried to obtain a crude product. Then, the crude product was purified by recrystallization using a mixture of methylbenzene and n-heptane, to obtain compound 64 as a light yellow solid (9.3 g, yield 79%).

Compounds as shown in Table 7 were synthesized by replacing the intermediate m-8 with the reactant J as shown in Table 7, replacing 2-chloro-4-phenylquinazoline with the reactant K based on the synthesis method similar to the compound 64:

TABLE 7 structures and raw materials of partial compounds

| Compound No. | Reactant J | Reactant K | Structure | Yield (%) |
|---|---|---|---|---|
| 67 | | | 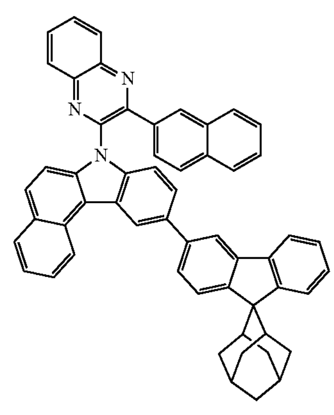 [SMILES: c1ccc2c(c1)-c1cc(-c3ccc4c(c3)c3c5ccccc5ccc3n4-c3nc4ccccc4nc3-c3ccc4ccccc4c3)ccc1C21C2CC3CC(C2)CC1C3] | 67 |

TABLE 7-continued structures and raw materials of partial compounds

| Compound No. | Reactant J | Reactant K | Structure | Yield (%) |
|---|---|---|---|---|
| 71 | | | 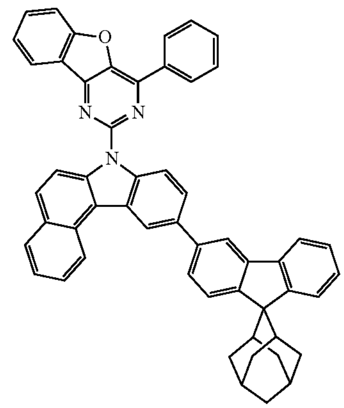 [SMILES: c1ccc(-c2nc(-n3c4ccc(-c5ccc6c(c5)-c5ccccc5C65C6CC7CC(C6)CC5C7)cc4c4c5ccccc5ccc43)nc3c2oc2ccccc23)cc1] | 75 |
| 84 | | | 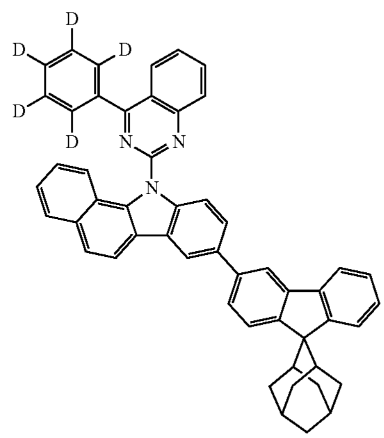 [SMILES: [2H]c1c([2H])c([2H])c(-c2nc(-n3c4ccc(-c5ccc6c(c5)-c5ccccc5C65C6CC7CC(C6)CC5C7)cc4c4ccc5ccccc5c43)nc3ccccc23)c([2H])c1[2H]] | 52 |
| 90 | | | 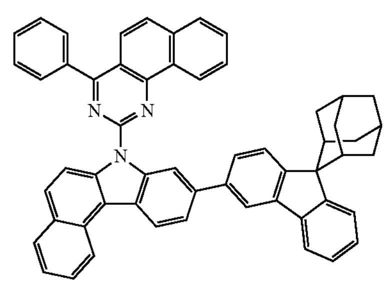 [SMILES: c1ccc(-c2nc(-n3c4cc(-c5ccc6c(c5)-c5ccccc5C65C6CC7CC(C6)CC5C7)ccc4c4c5ccccc5ccc43)nc3c2ccc2ccccc23)cc1] | 49 |
| 95 | | | 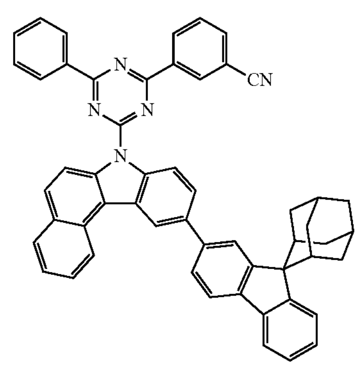 [SMILES: N#Cc1cccc(-c2nc(-c3ccccc3)nc(-n3c4ccc(-c5ccc6c(c5)C5(c7ccccc7-6)C6CC7CC(C6)CC5C7)cc4c4c5ccccc5ccc43)n2)c1] | 70 |

Mass spectrometry was performed on the intermediates synthesized above to obtain the data as shown in Table 8-1:

TABLE 8-1 mass spectrometric data of partial compounds

| Compound No. | Mass spectrometric data | Compound | Mass spectrometric data |
|---|---|---|---|
| 2 | m/z = 604.3 (M + H)+ | 54 | m/z = 584.3 (M + H)+ |
| 10 | m/z = 694.3 (M + H)+ | 58 | m/z = 694.3 (M + H)+ |
| 13 | m/z = 693.3 (M + H)+ | 79 | m/z = 809.4 (M + H)+ |
| 22 | m/z = 529.3 (M + H)+ | 100 | m/z = 680.3 (M + H)+ |
| 30 | m/z = 604.3 (M + H)+ | 64 | m/z = 706.3 (M + H)+ |
| 32 | m/z = 578.3 (M + H)+ | 67 | m/z = 756.3 (M + H)+ |
| 36 | m/z = 622.3 (M + H)+ | 71 | m/z = 746.3 (M + H)+ |
| 40 | m/z = 654.3 (M + H)+ | 84 | m/z = 711.4 (M + H)+ |
| 47 | m/z = 644.3 (M + H)+ | 90 | m/z = 756.3 (M + H)+ |
| 51 | m/z = 618.3 (M + H)+ | 95 | m/z = 758.3 (M + H)+ |

NMR analysis was performed on the above compounds; and partial NMR data results were shown in the following Table 8-2:

TABLE 8-2

Mass spectrometric data of partial compounds

| Compound No. | $^1$H-NMR (CDCl$_3$, 400M): |
|---|---|
| 2 | δ: 8.53 (s, 1H), 8.26 (d, 1H), 8.20 (d, 1H), 8.10 (d, 1H), 8.06 (s, 1H), 7.88 (d, 2H), 7.84 (d, 1H), 7.77-7.72 (m, 5H), 7.70 (d, 1H), 7.60 (d, 1H), 7.55-7.52 (m, 3H), 7.48 (t, 1H), 7.43 (t, 1H), 7.39-7.31 (m, 3H), 2.88 (d, 2H), 2.80 (d, 2H), 2.20 (s, 2H), 1.95 (s, 2H), 1.85-1.80 (m, 4H), 1.60 (s, 2H) ppm |
| 30 | δ: 8.12 (d, 1H), 8.09 (d, 1H), 7.89 (s, 1H), 7.80 (d, 1H), 7.71 (m, 1H), 7.64-7.59 (m, 4H), 7.57-7.55 (m, 3H), 7.48-7.41 (m, 5H), 7.35 (t, 1H), 7.28-7.22 (m, 4H), 7.13 (d, 1H), 2.79-2.69 (m, 4H), 2.16 (s, 2H), 1.91 (s, 2H), 1.84-1.78 (m, 4H), 1.56 (s, 2H) ppm |
| 95 | δ: 9.19 (d, 1H), 9.07-9.05 (m, 2H), 8.91 (d, 1H), 8.81-8.78 (m, 3H), 8.74 (d, 1H), 8.36 (s, 1H), 8.24 (d, 1H), 8.11 (d, 1H), 8.01 (d, 1H), 7.97 (d, 1H), 7.84 (d, 1H), 7.81 (d, 1H), 7.70 (d, 1H), 7.62-7.55 (m, 5H), 7.47-7.45 (m, 2H), 7.35 (t, 1H), 7.32 (t, 1H), 2.95 (d, 2H), 2.87 (d, 2H), 2.26 (s, 2H), 1.99 (s, 2H), 1.91-1.85 (m, 4H), 1.71 (s, 2H) ppm |

Preparation and Performance Evaluation of the Organic Electroluminescent Device

Example 1: Green Organic Electroluminescent Device

The green organic electroluminescent device was manufactured by the following method:

Preparation of an anode by the following process: a substrate (manufactured by Corning) having an ITO thickness of 1500 Å was cut into a size of 40 mm (length)×40 mm (width)×0.7 mm (thickness), and prepared into an experimental substrate with a cathode, anode and insulating layer pattern by a photoetching process; then the experimental substrate was subjected to surface treatment with UV, ozone, $O_2$:$N_2$ plasma to enhance a work function of the anode (experimental substrate) and clear away dross.

$F_4$-TCNQ was vacuum evaporated on the experimental substrate (anode) to form a hole injection layer (HIL) having a thickness of 100 Å, and HT-01 was evaporated on the HIL to form a first hole transport layer having a thickness of 800 Å.

HT-02 was vacuum evaporated on the first hole transport layer to form a second hole transport layer having a thickness of 300 Å.

The compound 2:GH-n1:Ir(ppy)$_3$ were jointly evaporated on the second hole transport layer according to a ratio of 50%:45%:5% (evaporation rate) to form a green emitting layer (EML) having a thickness of 400 Å.

ET-01 and LiQ were mixed according to a weight ratio of 1:1 and evaporated to form an electron transport layer (ETL) having a thickness of 300 Å; LiQ was evaporated on the electron transport layer to form an electron injection layer (EIL) having a thickness of 10 Å, then Mg and Ag were mixed according to an evaporation rate of 1:9, and then vacuum evaporated on the electron injection layer, thus forming a cathode having a thickness of 105 Å.

In addition, CP-01 having a thickness of 650 Å was evaporated on the above cathode to form an organic capping layer (CPL), thus completing the manufacture of the organic luminescent device.

Examples 2 to 12

The organic electroluminescent device was prepared by replacing the compound 2 in Example 1 with compounds as shown in column X in Table 9 according to the method the same as that in Example 1. In the organic light-emitting layer of the prepared organic electroluminescent device, the compound X:GH-n1:Ir(ppy)$_3$=50%:45%:5%. For example, in Example 2, the compound X is compound 10; the compound 10 is used to replace the compound 2 in Example 1 to prepare the organic electroluminescent device.

Comparative Example 1

The organic electroluminescent device was prepared by replacing the compound 2 in Example 1 with the compound A according to the method the same as that in Example 1. In the organic light-emitting layer of the prepared organic electroluminescent device, the compound A:GH-n1:Ir(ppy)$_3$=50%:45%:5%.

Comparative Example 2

The organic electroluminescent device was prepared by replacing the compound 2 in Example 1 with the compound B according to the method the same as that in Example 1. In the organic light-emitting layer of the prepared organic electroluminescent device, the compound B:GH-n1:Ir(ppy)$_3$=50%:45%:5%.

Comparative Example 3

The organic electroluminescent device was prepared by replacing the compound 2 in Example 1 with the compound C according to the method the same as that in Example 1. In the organic light-emitting layer of the prepared organic electroluminescent device, the compound C:GH-n1:Ir(ppy)$_3$=50%:45%:5%.

In Examples 1 to 12 and Comparative Examples 1 to 3, partial materials used have the following structures:
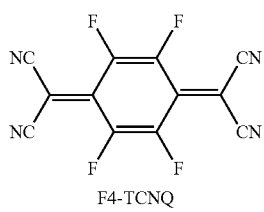
F4-TCNQ
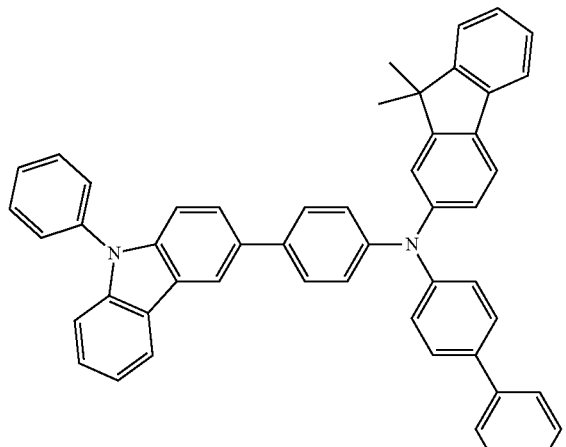
HT-01
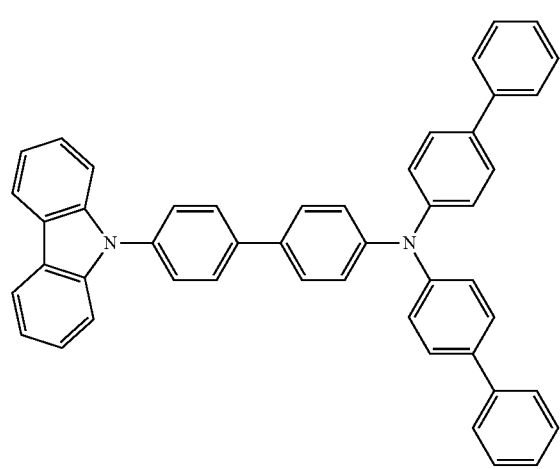
HT-02
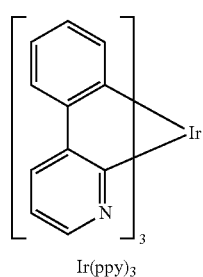
Ir(ppy)$_3$
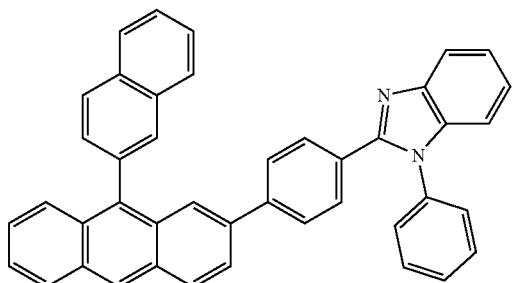
ET-01
LiQ
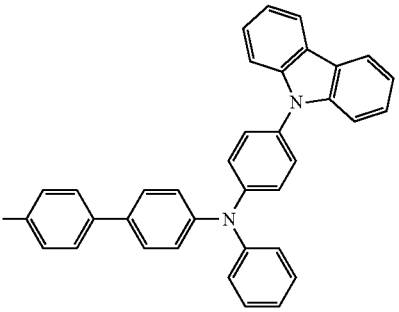
CP-01
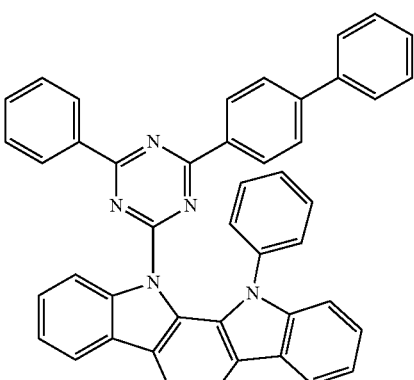
GH-n1

-continued

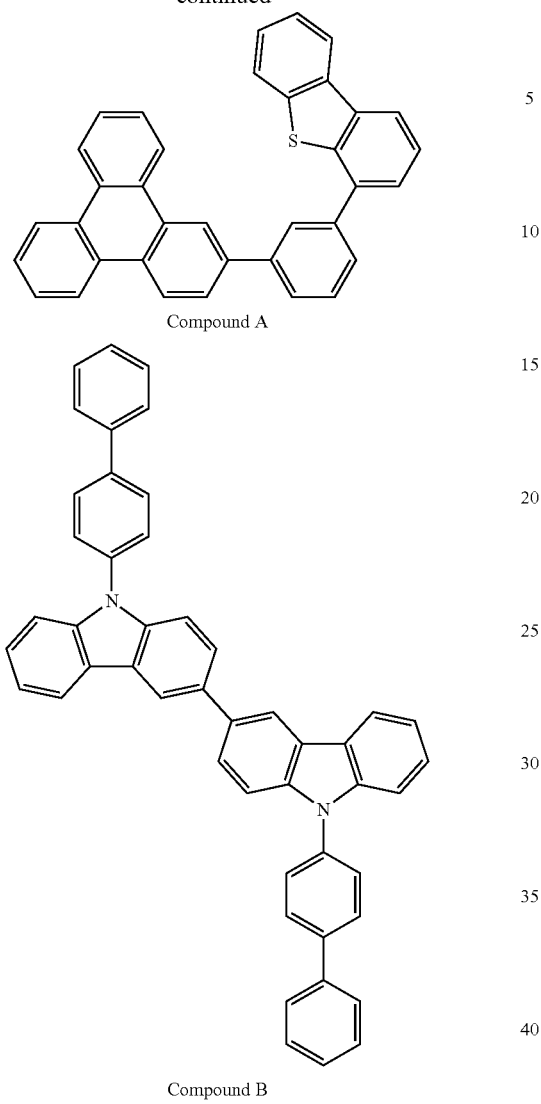

Compound A

Compound B

-continued

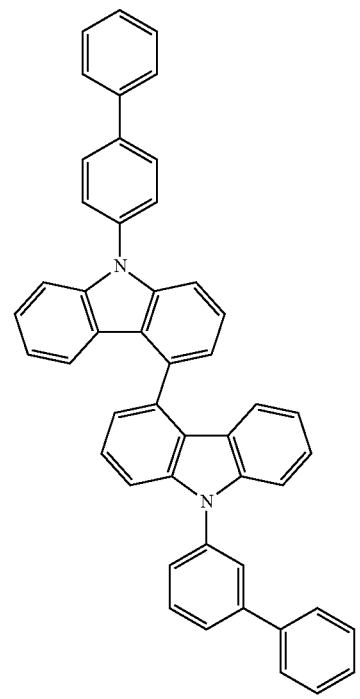

Compound C

Performance test was performed on the organic electroluminescent device prepared in Examples 1 to 12 and Comparative Examples 1 to 3 at a condition of 20 mA/cm²; and the test results were shown in Table 9.

Example 9: performance test result of the organic electroluminescent device

| Example No. | Compound X | Driving voltage V | Current efficiency (Cd/A) | Power efficiency (lm/W) | Chromaticity coordinate CIEx | Chromaticity coordinate CIEy | External quantum efficiency EQE (%) | T95 lifetime (h) |
| --- | --- | --- | --- | --- | --- | --- | --- | --- |
| Example 1 | 2 | 3.69 | 82.3 | 70.0 | 0.22 | 0.73 | 19.7 | 348 |
| Example 2 | 10 | 3.76 | 74.0 | 61.8 | 0.22 | 0.73 | 17.7 | 341 |
| Example 3 | 13 | 3.65 | 72.9 | 62.7 | 0.22 | 0.73 | 17.5 | 323 |
| Example 4 | 22 | 3.76 | 87.2 | 72.9 | 0.22 | 0.73 | 20.9 | 322 |
| Example 5 | 30 | 3.76 | 83.4 | 69.6 | 0.22 | 0.73 | 20.0 | 361 |
| Example 6 | 32 | 3.76 | 87.7 | 73.3 | 0.22 | 0.73 | 21.1 | 306 |
| Example 7 | 36 | 3.88 | 86.9 | 70.3 | 0.22 | 0.73 | 20.8 | 350 |
| Example 8 | 40 | 3.66 | 78.4 | 67.3 | 0.22 | 0.73 | 18.8 | 308 |
| Example 9 | 47 | 3.82 | 80.6 | 66.3 | 0.22 | 0.73 | 19.3 | 354 |
| Example 10 | 51 | 3.71 | 80.0 | 67.8 | 0.22 | 0.73 | 19.2 | 308 |
| Example 11 | 54 | 3.85 | 82.9 | 67.6 | 0.22 | 0.73 | 19.9 | 332 |
| Example 12 | 58 | 3.71 | 75.4 | 63.8 | 0.22 | 0.73 | 18.1 | 307 |
| Comparative Example 1 | A | 3.71 | 68.2 | 57.7 | 0.22 | 0.73 | 16.4 | 154 |
| Comparative Example 2 | B | 3.72 | 69.2 | 58.4 | 0.22 | 0.73 | 16.6 | 206 |
| Comparative Example 3 | C | 3.75 | 69.3 | 58.0 | 0.22 | 0.73 | 16.6 | 165 |

It can be seen from the data in Table 9 that compared with the organic electroluminescent devices prepared in Comparative Examples 1 to 3, the organic electroluminescent devices prepared in Examples 1 to 12 have improved current efficiency, power efficiency, external quantum efficiency and lifetime. Therefore, the nitrogen-containing compound of the present disclosure serves as a material for an organic light-emitting layer of the organic electroluminescent device, especially, as a host material for an organic light-emitting layer of the organic electroluminescent device, which may improve the efficiency performance and lifetime performance of the organic electroluminescent device.

Example 13: Red Organic Electroluminescent Device

Preparation of an anode by the following process: a substrate (manufactured by Corning) having an ITO thickness of 1500 Å was cut into a size of 40 mm (length)×40 mm (width)×0.7 mm (thickness), and prepared into an experimental substrate with a cathode, anode and insulating layer pattern by a photoetching process; then the experimental substrate was subjected to surface treatment with UV, ozone, $O_2:N_2$ plasma to enhance a work function of the anode (experimental substrate) and clear away dross.

$F_4$-TCNQ was vacuum evaporated on the experimental substrate (anode) to form a hole injection layer (HIL) having a thickness of 100 Å, and HT-01 was evaporated on the HIL to form a first hole transport layer having a thickness of 800 Å.

HT-03 was vacuum evaporated on the first hole transport layer to form a second hole transport layer having a thickness of 850 Å.

The compound 64:Ir(piq)$_2$(acac) were jointly evaporated on the second hole transport layer according to a ratio of 95%:5% (evaporation rate) to form a red emitting layer (EML) having a thickness of 350 Å.

ET-01 and LiQ were mixed according to a weight ratio of 1:1 and evaporated to form an electron transport layer (ETL) having a thickness of 300 Å; LiQ was evaporated on the electron transport layer to form an electron injection layer (EIL) having a thickness of 10 Å, then Mg and Ag were mixed according to an evaporation rate of 1:9, and then vacuum evaporated on the electron injection layer, thus forming a cathode having a thickness of 105 Å.

In addition, CP-01 having a thickness of 650 Å was evaporated on the above cathode to form an organic capping layer, thus completing the manufacture of the organic luminescent device.

Examples 14 to 20

The organic electroluminescent device was prepared by replacing the compound 64 in Example 13 with compounds as shown in column Y in Table 10 according to the method the same as that in Example 13. In the organic light-emitting layer of the prepared organic electroluminescent device, the compound Y:Ir(piq)$_2$(acac)=95%:5%. For example, in Example 14, the compound Y is compound 67; the compound 67 is used to replace the compound 64 in Example 13 to prepare the organic electroluminescent device.

Comparative Example 4

The organic electroluminescent device was prepared by replacing the compound 64 in Example 13 with the compound BAlq according to the method the same as that in Example 13. In the organic light-emitting layer of the prepared organic electroluminescent device, the compound BAlq:Ir(piq)$_2$(acac)=95%:5%.

Comparative Example 5

The organic electroluminescent device was prepared by replacing the compound 64 in Example 13 with the compound D according to the method the same as that in Example 13. In the organic light-emitting layer of the prepared organic electroluminescent device, the compound D:Ir(piq)$_2$(acac)=95%: 5%.

Comparative Example 6

The organic electroluminescent device was prepared by replacing the compound 64 in Example 13 with the compound E according to the method the same as that in Example 13. In the organic light-emitting layer of the prepared organic electroluminescent device, the compound E:Ir(piq)$_2$(acac)=95%:5%.

Partial materials used in Examples 13 to 20 and Comparative Examples 4 to 6 have the following structures:

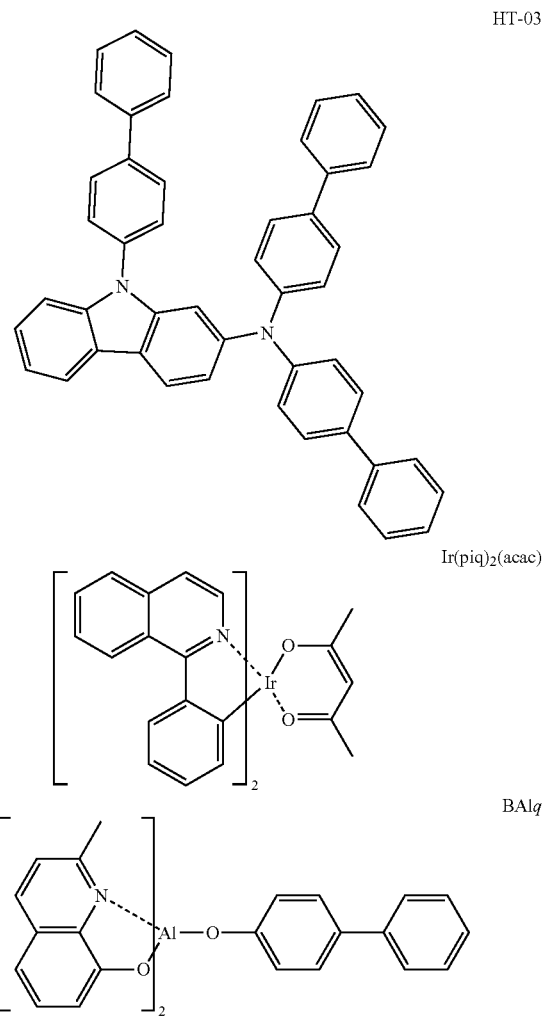

Coumpound D

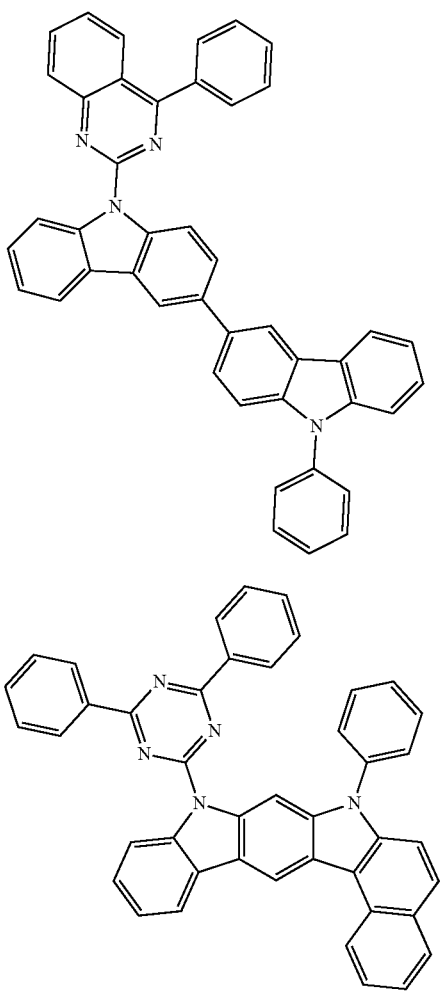

Compound E

Performance test was performed on the organic electroluminescent device prepared in Examples 13 to 20 and Comparative Examples 4 to 6 at a condition of 20 mA/cm$^2$; and the test results were shown in Table 10.

It can be seen from the data in Table 10 that compared with the organic electroluminescent devices prepared in Comparative Examples 4 to 6, the organic electroluminescent devices prepared in Examples 13 to 20 have improved lifetime. Therefore, the nitrogen-containing compound of the present disclosure serves as a material for an organic light-emitting layer of the organic electroluminescent device, especially, as a host material for an organic light-emitting layer of the organic electroluminescent device, which may improve the efficiency performance and lifetime performance of the organic electroluminescent device.

The invention claimed is:

1. A nitrogen-containing compound, wherein the nitrogen-containing compound has a structural formula as shown in a chemical formula 1:

Chemical formula 1

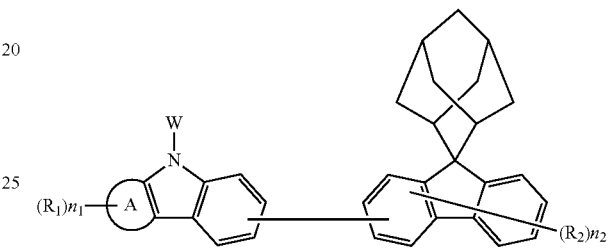

wherein, ring A is a benzene ring or naphthalene ring;
$R_1$ and $R_2$ are the same or different from each other, and are each independently selected from deuterium, fluorine, chlorine, cyano, methyl, isopropyl, ethyl, cyclopropyl and tert-butyl;
$n_1$ is 0, 1, 2, 3 or 4; when $n_1$ is greater than 1, any two of $R_1$ are the same or different;
$n_2$ is 0, 1, 2, 3 or; when $n_2$ is greater than 1, any two of $R_2$ are the same or different; and
W is

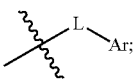

| Example 10: performance test result of the organic electroluminescent device | | | | | | | |
|---|---|---|---|---|---|---|---|
| Example No. | Compound Y | Driving voltage (V) | Current efficiency (cd/A) | Power efficiency (lm/W) | Chromaticity coordinate CIE-x | Chromaticity coordinate CIE-y | External quantum efficiency EQE (%) | T95 lifetime (h) |
| Example 13 | 64 | 3.78 | 31.6 | 26.2 | 0.68 | 0.32 | 21.5 | 363 |
| Example 14 | 67 | 3.77 | 31.5 | 26.2 | 0.68 | 0.32 | 21.4 | 366 |
| Example 15 | 71 | 3.72 | 30.8 | 26.0 | 0.68 | 0.32 | 21.0 | 443 |
| Example 16 | 79 | 3.72 | 30.6 | 25.8 | 0.68 | 0.32 | 20.8 | 470 |
| Example 17 | 84 | 3.60 | 31.0 | 27.0 | 0.68 | 0.32 | 21.1 | 356 |
| Example 18 | 90 | 3.72 | 32.9 | 27.8 | 0.68 | 0.32 | 22.4 | 412 |
| Example 19 | 95 | 3.76 | 32.6 | 27.3 | 0.68 | 0.32 | 22.2 | 471 |
| Example 20 | 100 | 3.63 | 32.8 | 28.4 | 0.68 | 0.32 | 22.3 | 394 |
| Comparative Example 4 | BAlq | 4.38 | 22.5 | 16.1 | 0.68 | 0.32 | 15.3 | 150 |
| Comparative Example 5 | D | 3.88 | 28.5 | 23.1 | 0.68 | 0.32 | 19.4 | 290 |
| Comparative Example 6 | E | 4.05 | 29.7 | 23.0 | 0.68 | 0.32 | 20.2 | 278 | wherein L is independently selected from a single bond, or an unsubstituted $L_1$, or a substituted $L_1$, wherein the unsubstituted $L_1$ is selected from the group consisting of the following groups:

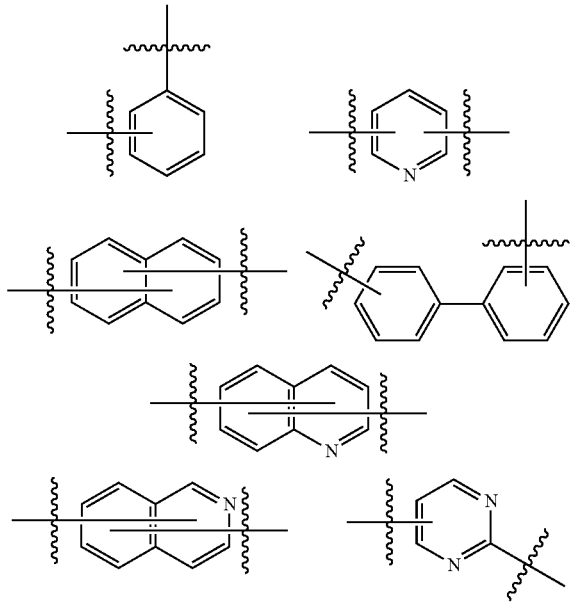

wherein, the substituted $L_1$ is a group formed by substituting the unsubstituted $L_1$ by one or more substituents selected from deuterium, F, Cl, cyano, methyl, ethyl, isopropyl, n-propyl, tert-butyl and phenyl; and when the substituted $L_1$ has a plurality of substituents, any two of the substituents are the same or different;

the Ar is selected from an unsubstituted $Ar_1$ or a substituted $Ar_1$, wherein the unsubstituted $Ar_1$ is selected from the group consisting of the following groups:

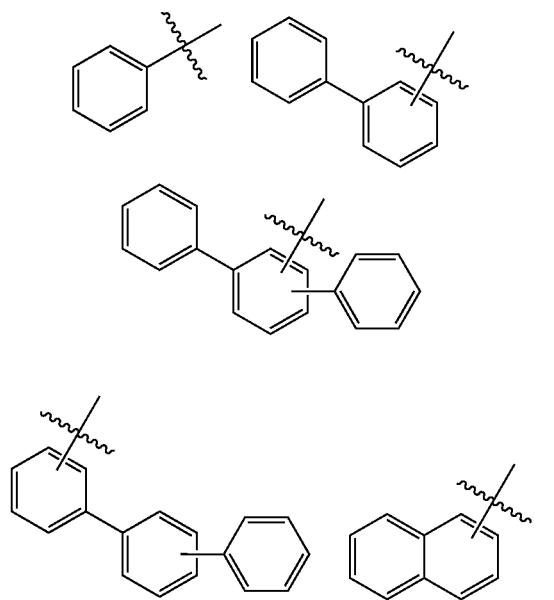

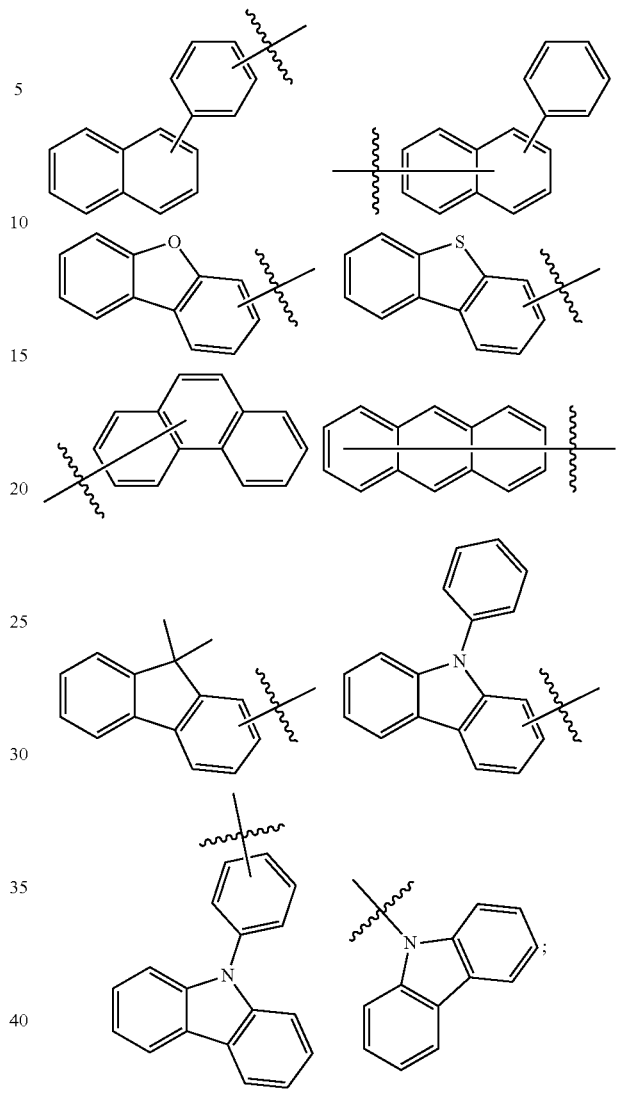

the substituted $Ar_1$ is a group formed by substituting the unsubstituted $Ar_1$ by one or more of substituents selected from deuterium, F, Cl, Br, cyano, alkyl with 1 to 4 carbon atoms, phenyl, naphthyl, dibenzothienyl, dibenzofuranyl, carbazolyl, pyridinyl, halomethyl and trimethylsilyl; and when the substituted $Ar_1$ has a plurality of substituents, any two of the substituents are the same or different;

or, the Ar is selected from the group consisting of the following substituents:

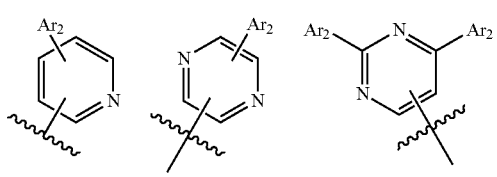

-continued

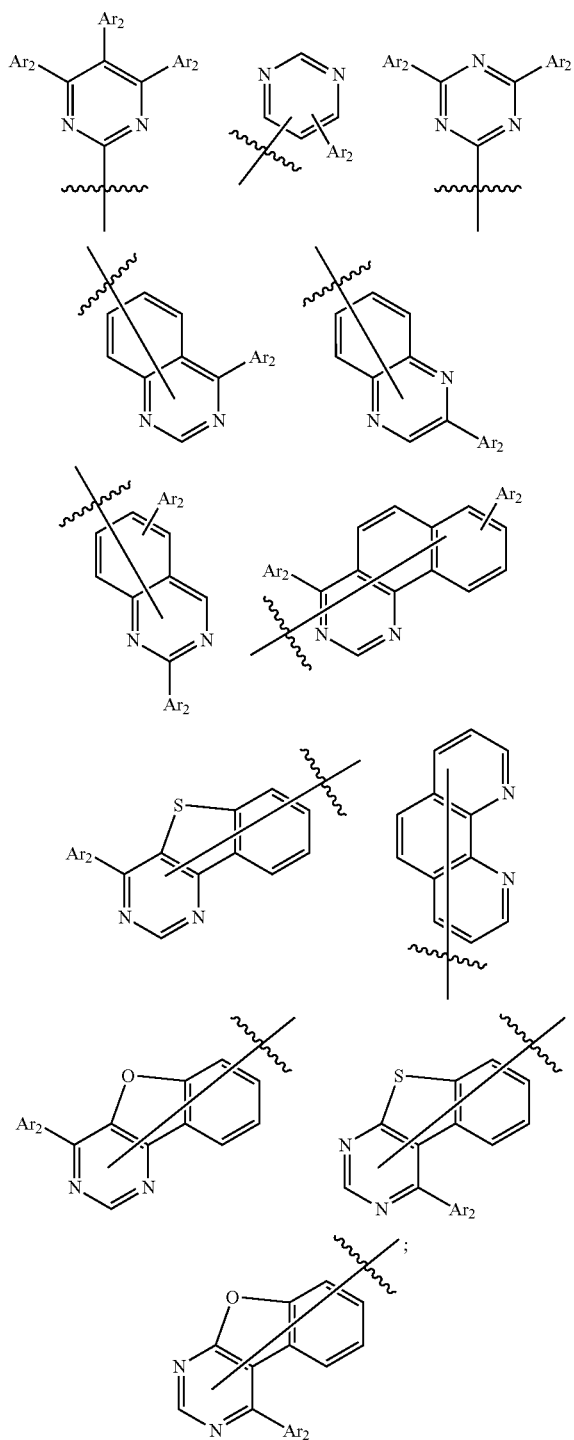

wherein, Ar₂ is selected from hydrogen, deuterium, substituted or unsubstituted aryl with 6 to 15 carbon atoms, and substituted or unsubstituted heteroaryl with 3 to 12 carbon atoms: any two of Ar₂ are the same or different; and the heteroaryl comprises 1, 2 or 3 heteroatoms of any choice from O, S or N;

substituents in Ar₂ are selected from deuterium, F, Cl and cyano; and when Ar₂ has a plurality of substituents, any two of the substituents are the same or different.

2. The nitrogen-containing compound according to claim 1, wherein the nitrogen-containing compound has a structural formula as shown in any one of the chemical formulas (f-1) to (f-12):

(f-1)

(f-2)

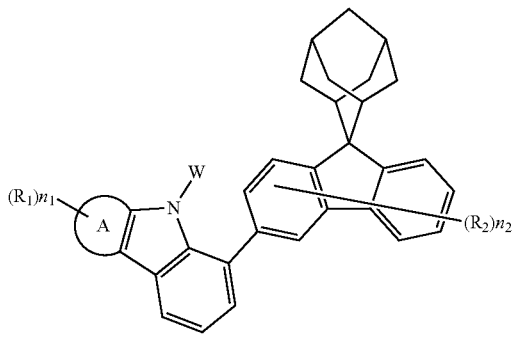

(f-3)

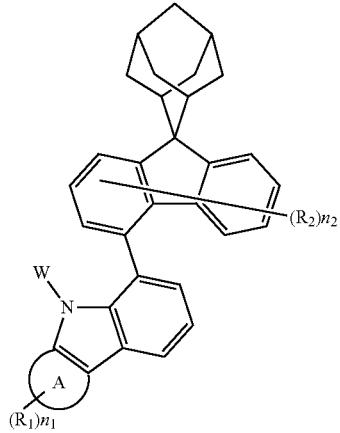

(f-4)

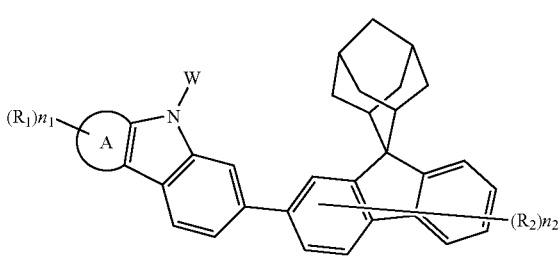

(f-5)
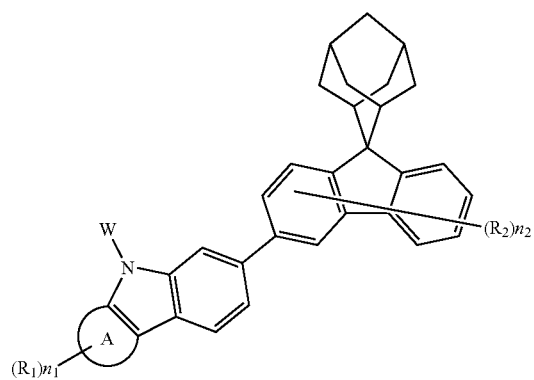
(f-6)
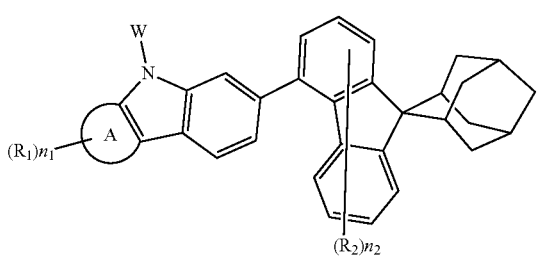
(f-7)
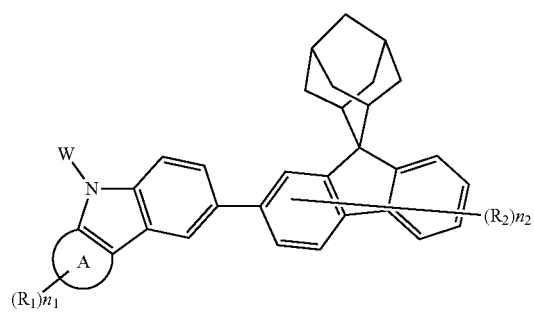
(f-8)
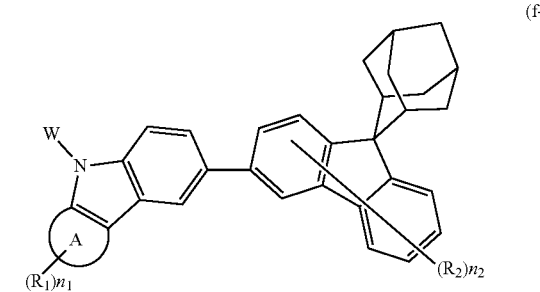
(f-9)
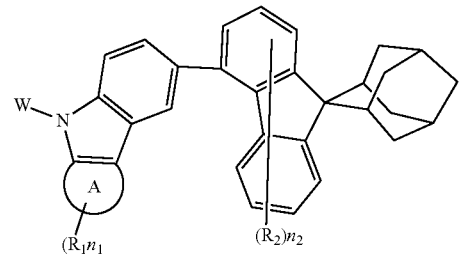
(f-10)
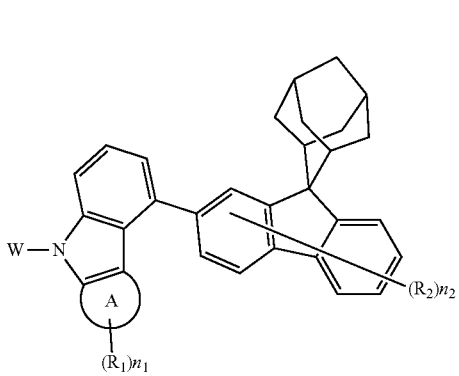
(f-11)
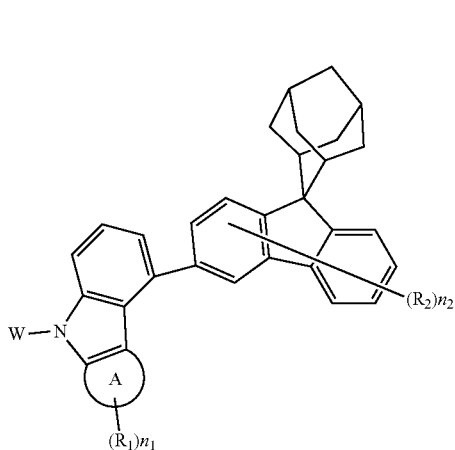
(f-12)
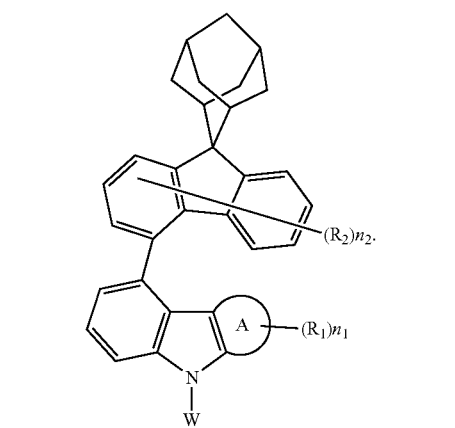

3. The nitrogen-containing compound according to claim 1, wherein the Ar₂ is selected from: hydrogen, substituted or unsubstituted phenyl, substituted or unsubstituted naphthyl, substituted or unsubstituted anthracyl, substituted or unsubstituted phenanthryl, substituted or unsubstituted biphenyl, substituted or unsubstituted fluorenyl, substituted or unsubstituted dibenzothiophenyl, substituted or unsubstituted dibenzofuryl, substituted or unsubstituted pyridyl, substituted or unsubstituted pyrimidyl, substituted or unsubstituted pyrazinyl, substituted or unsubstituted quinolyl, substituted or unsubstituted isoquinolyl, and substituted or unsubstituted quinazolinyl; and substituents in Ar₂ are each independently selected from: F, deuterium, and cyano.

4. A nitrogen-containing compound, wherein the nitrogen-containing compound is selected from the group consisting of the following compounds:

1

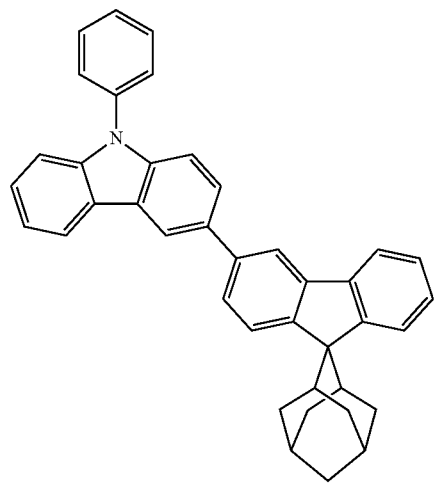

2

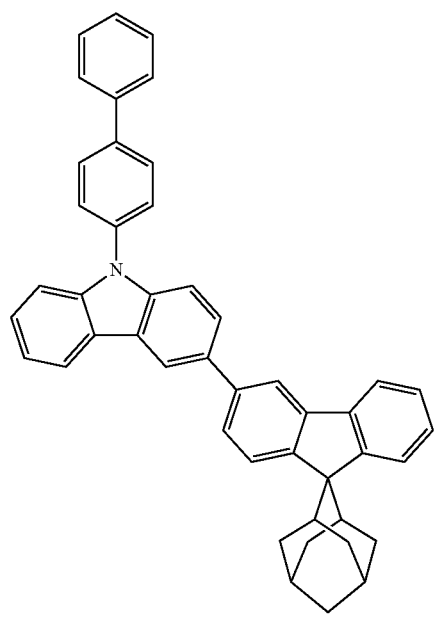

-continued

3

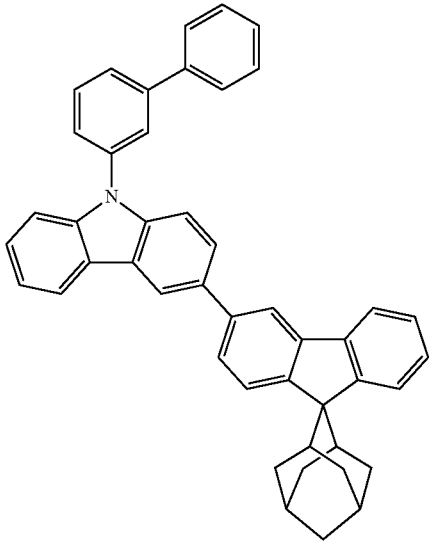

4

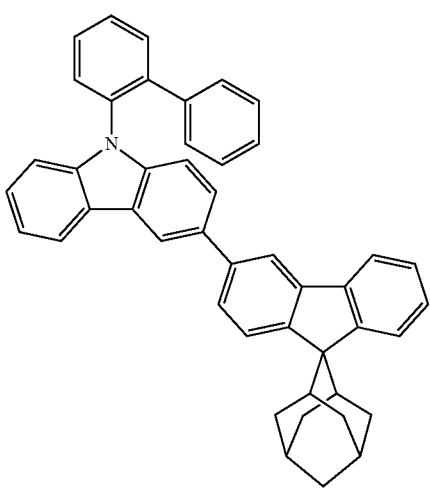

5

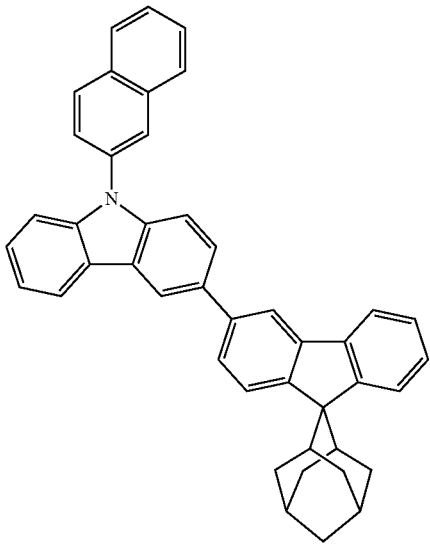

149
-continued
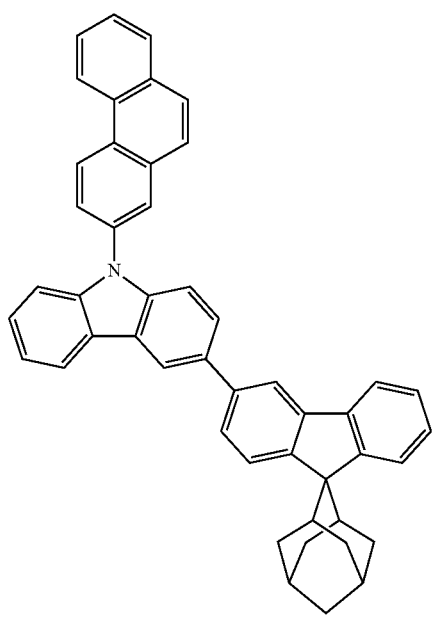
150
-continued
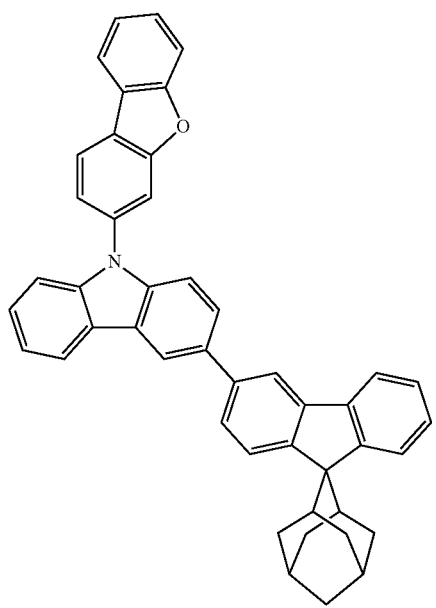
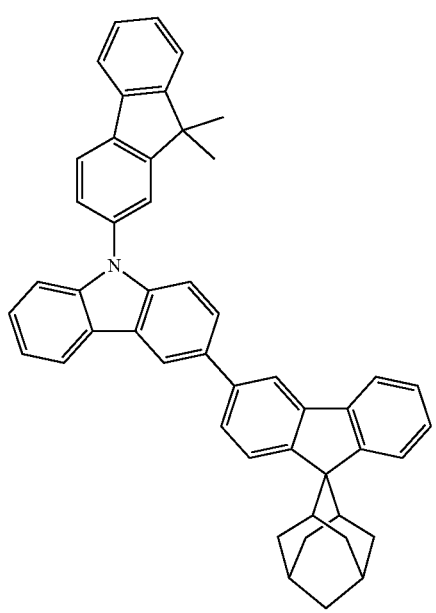
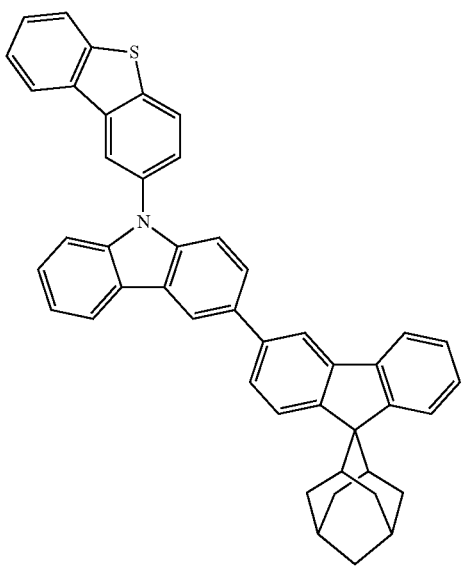

151
-continued
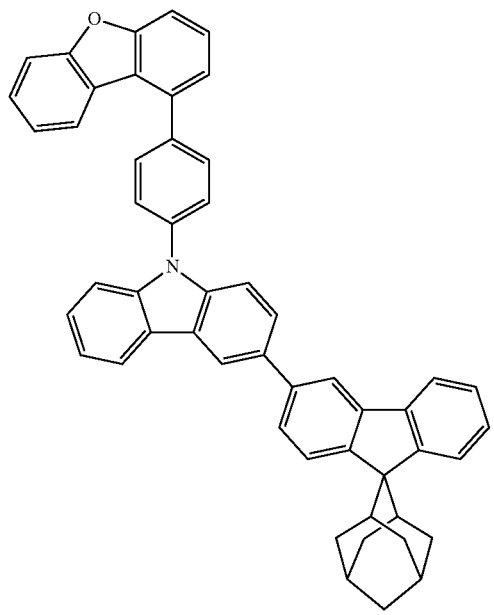
10
11
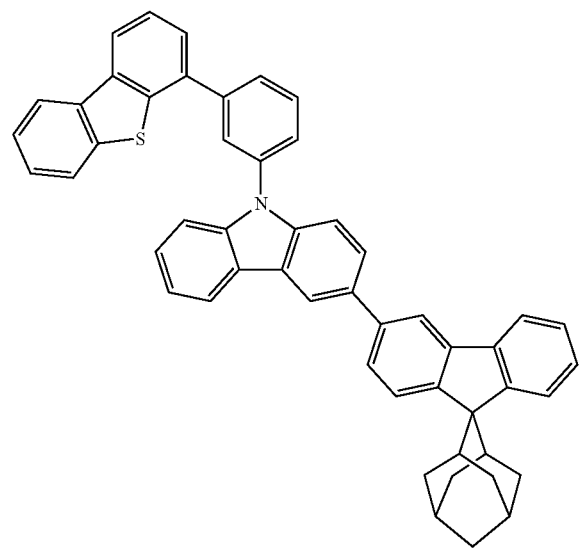
152
-continued
12
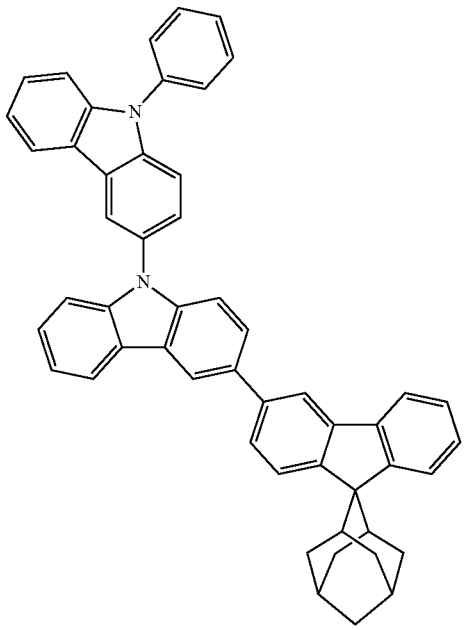
13
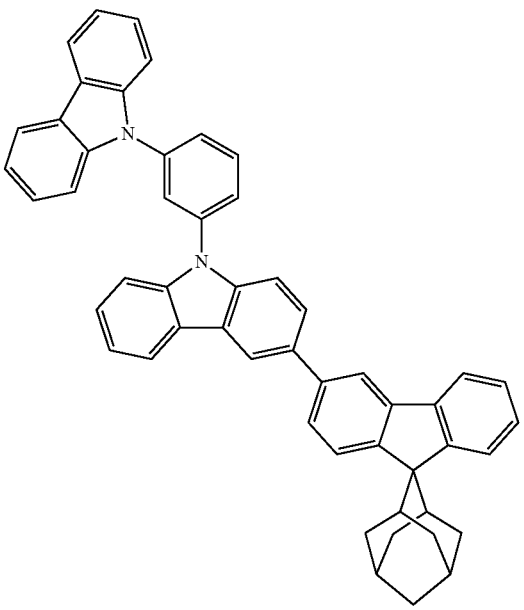

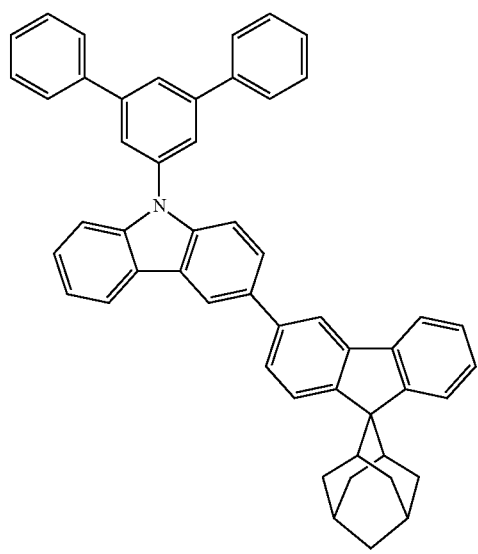
14
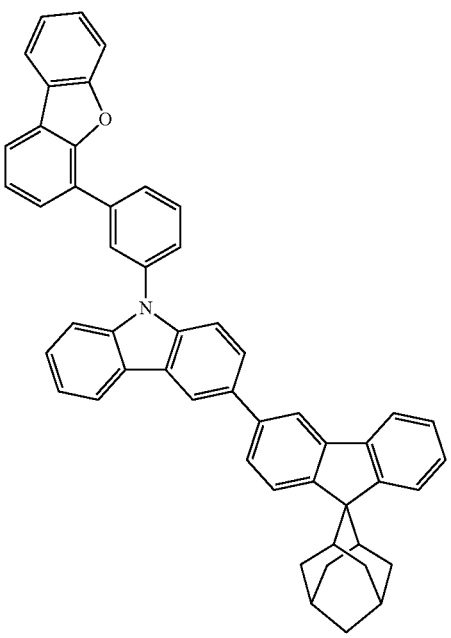
15
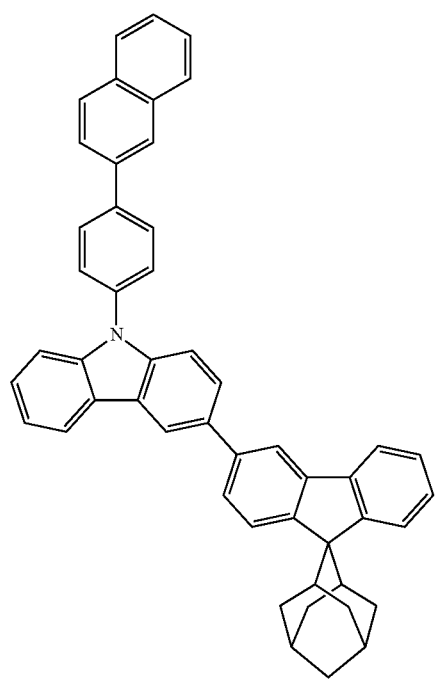
16
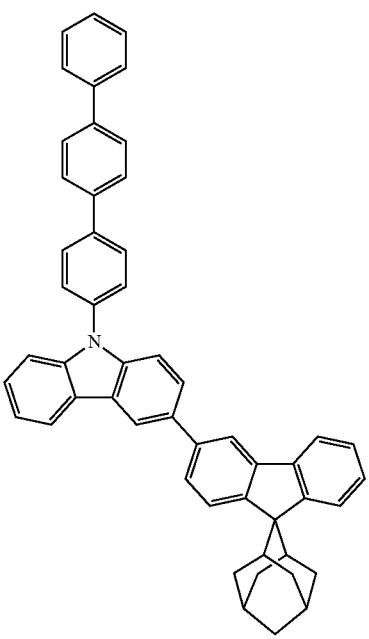
17

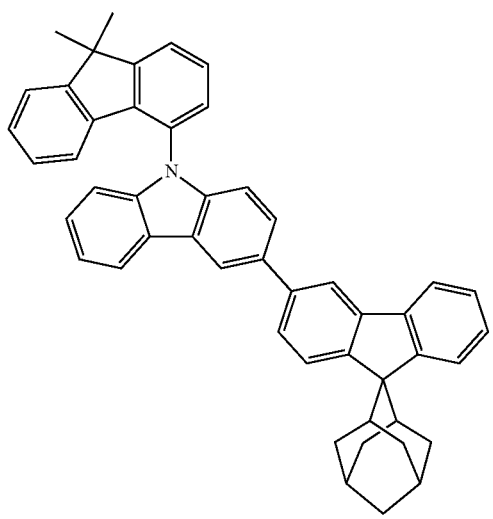
18
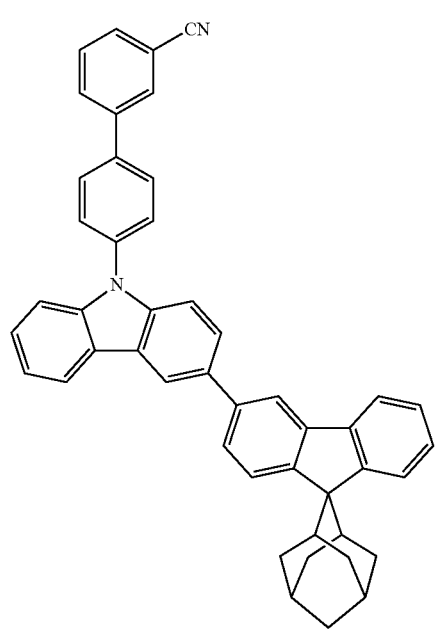
19
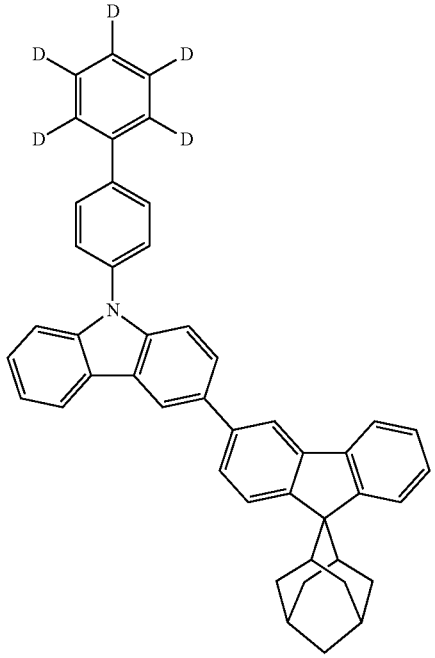
20
21
22

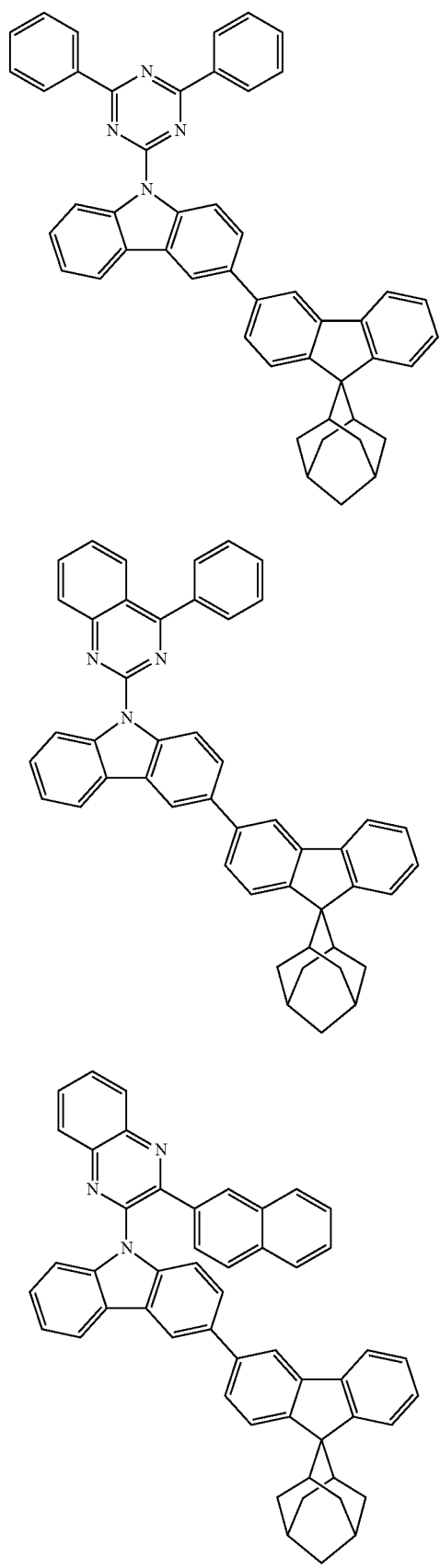
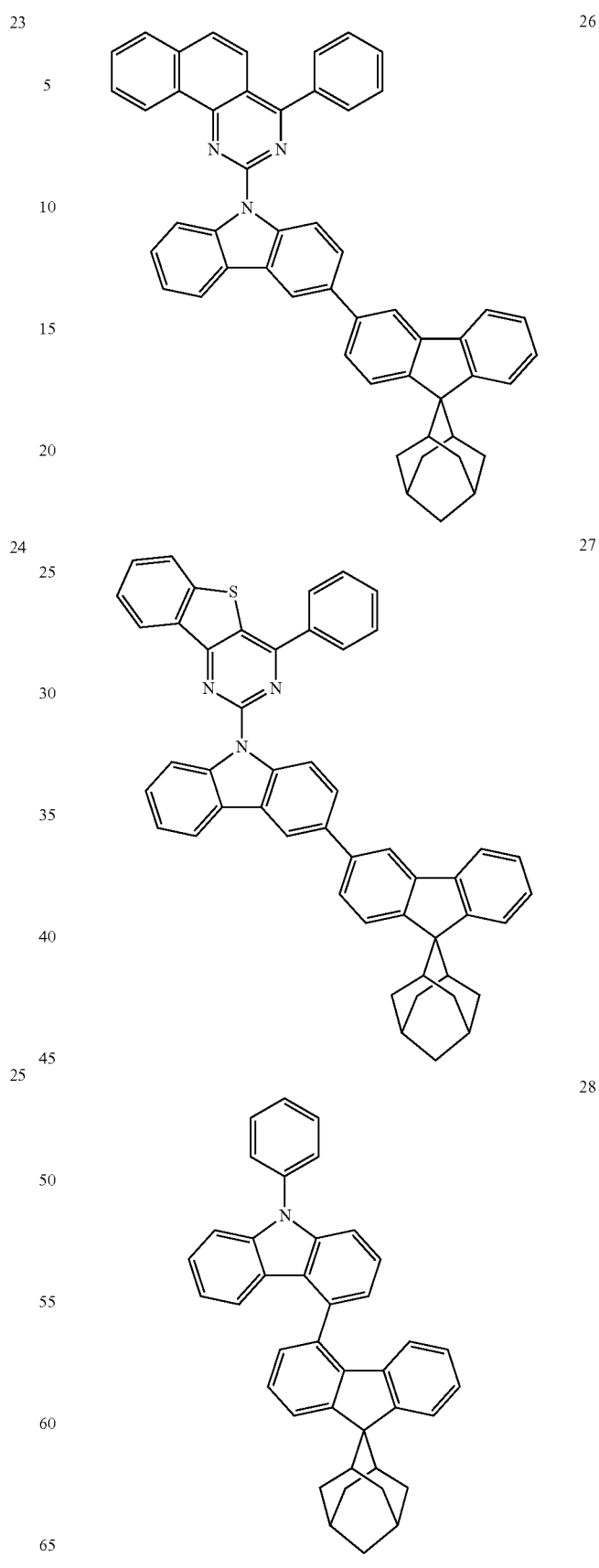

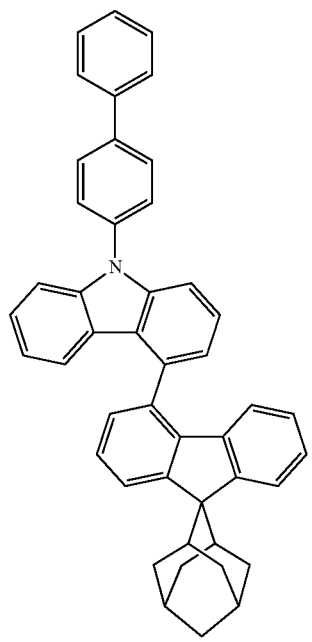
29
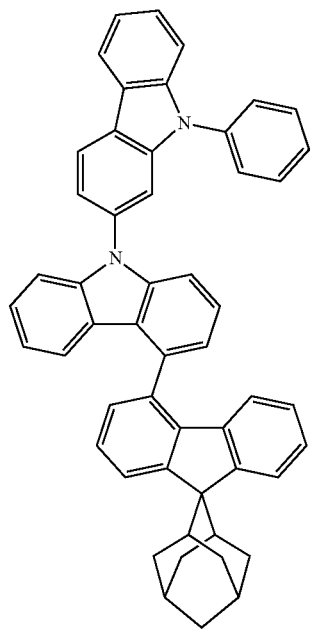
31
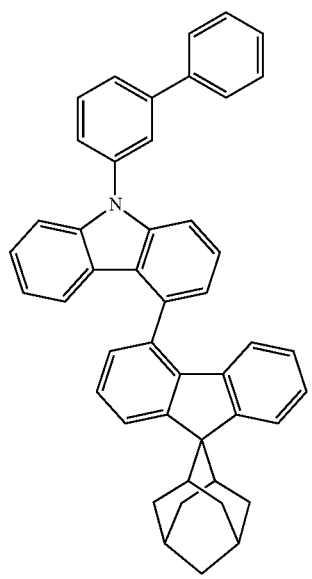
30
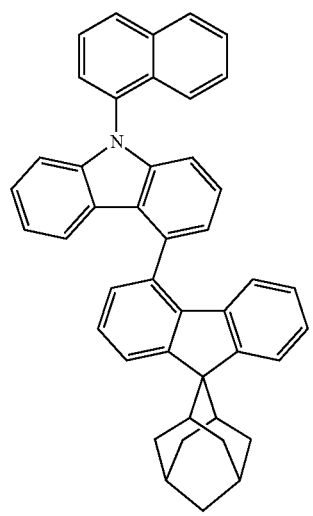
32

33
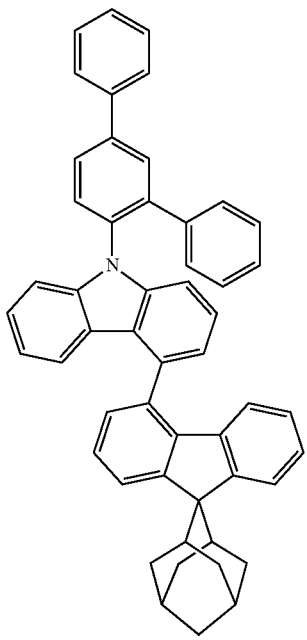
34
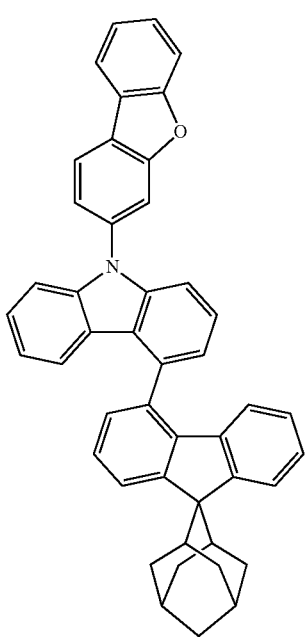
35
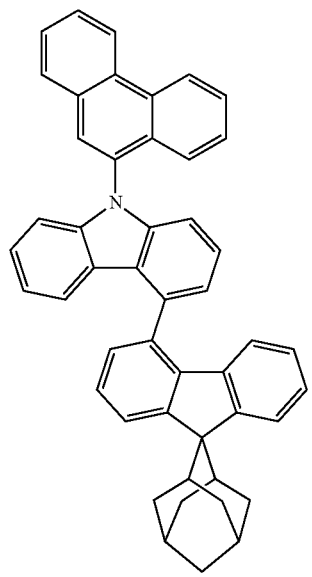
36
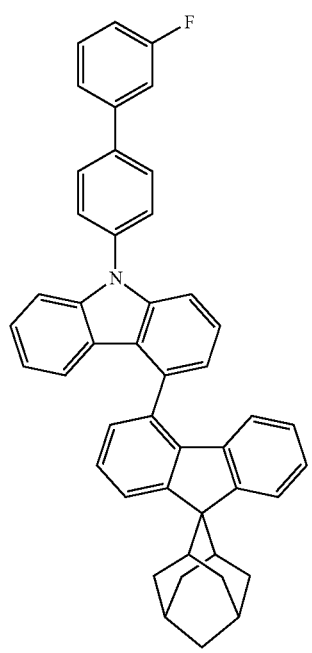

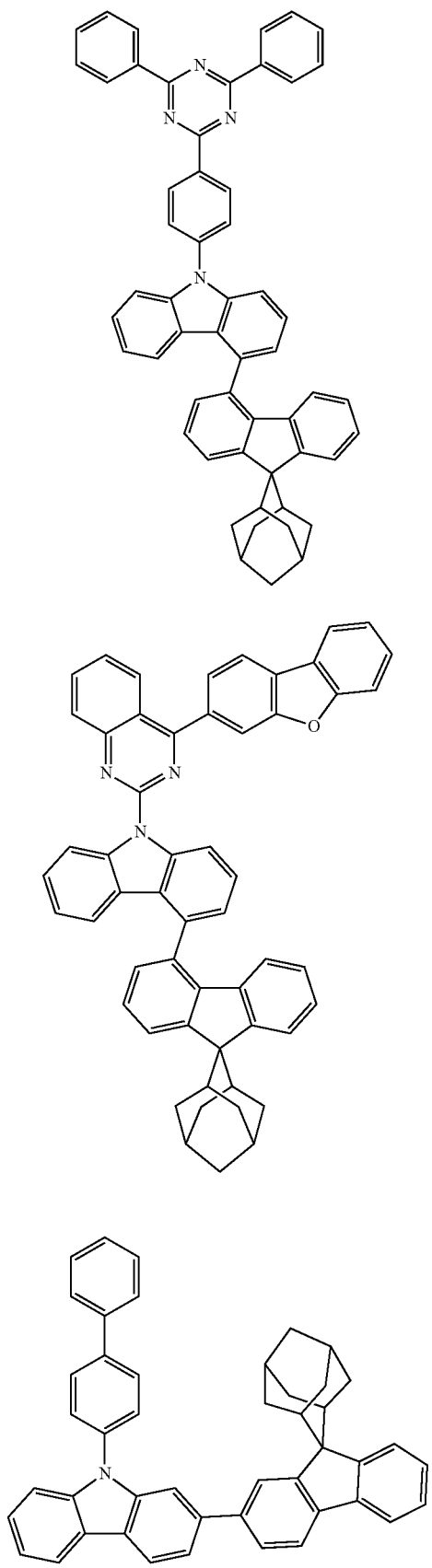
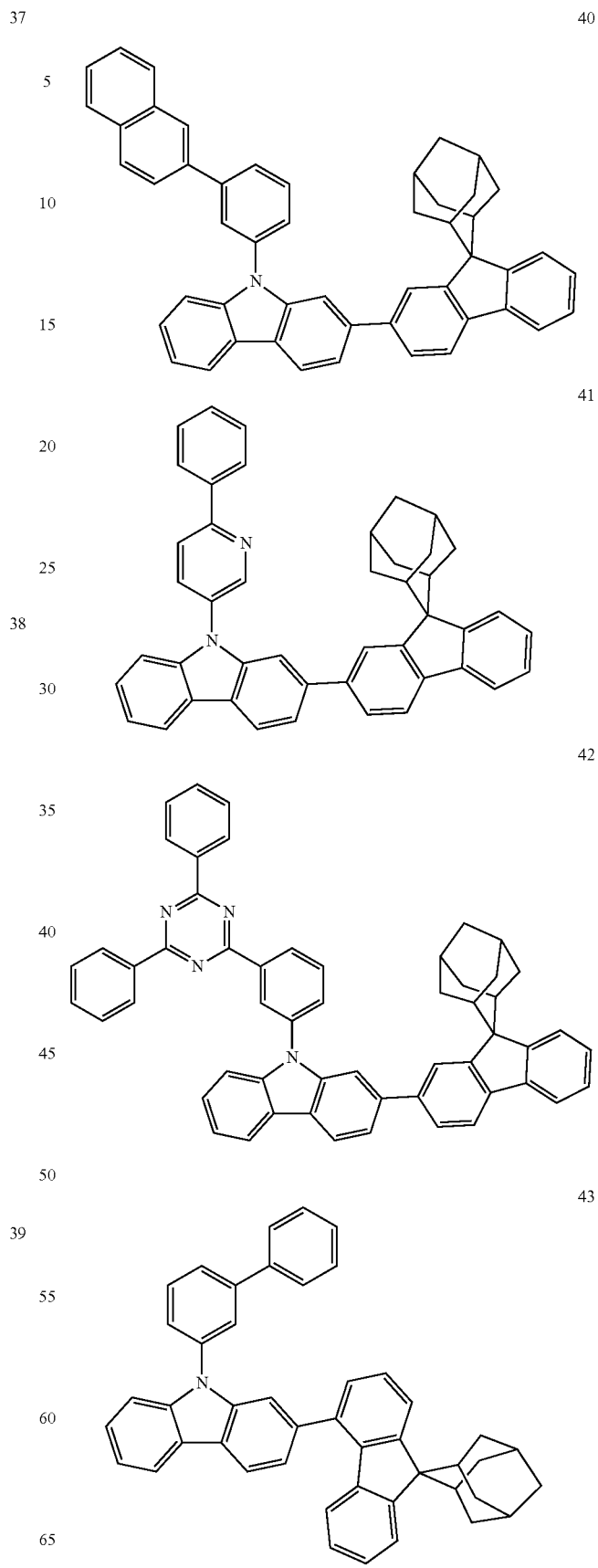

44
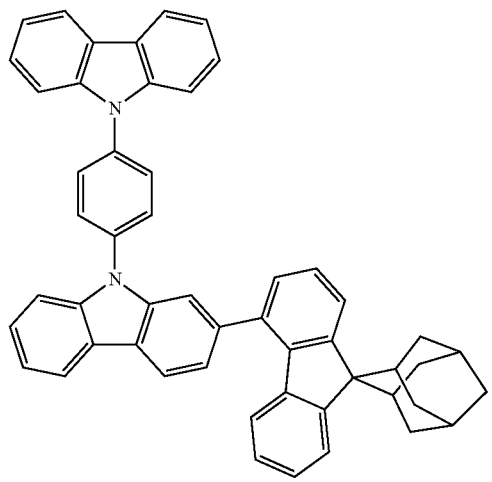
45
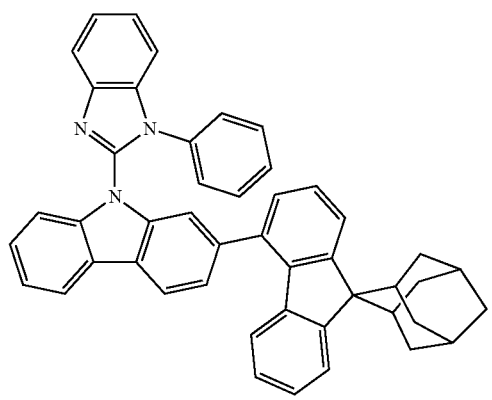
46
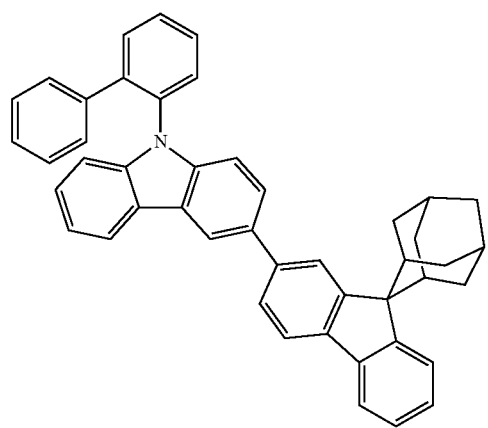
47
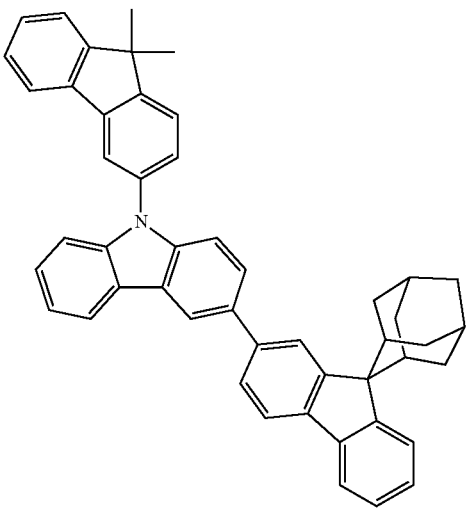
48
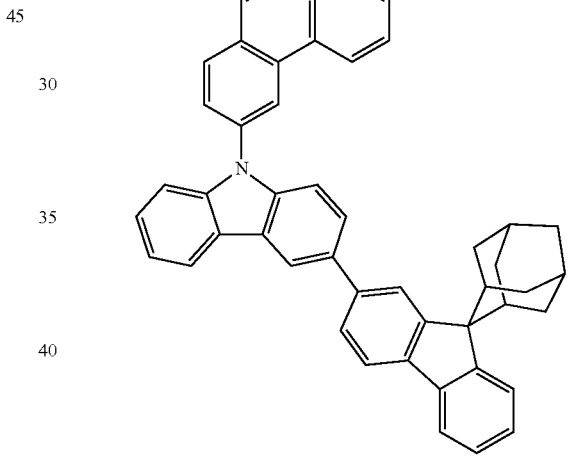
49
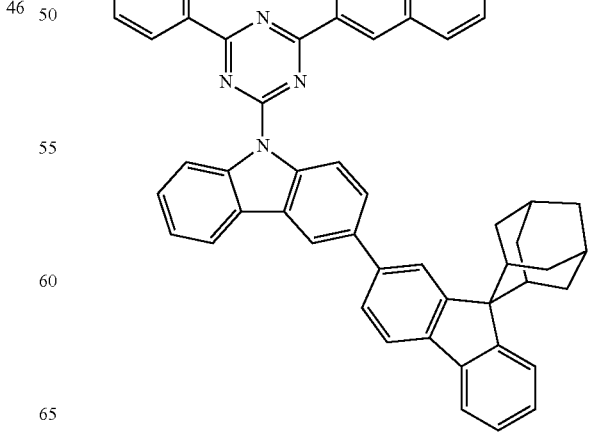

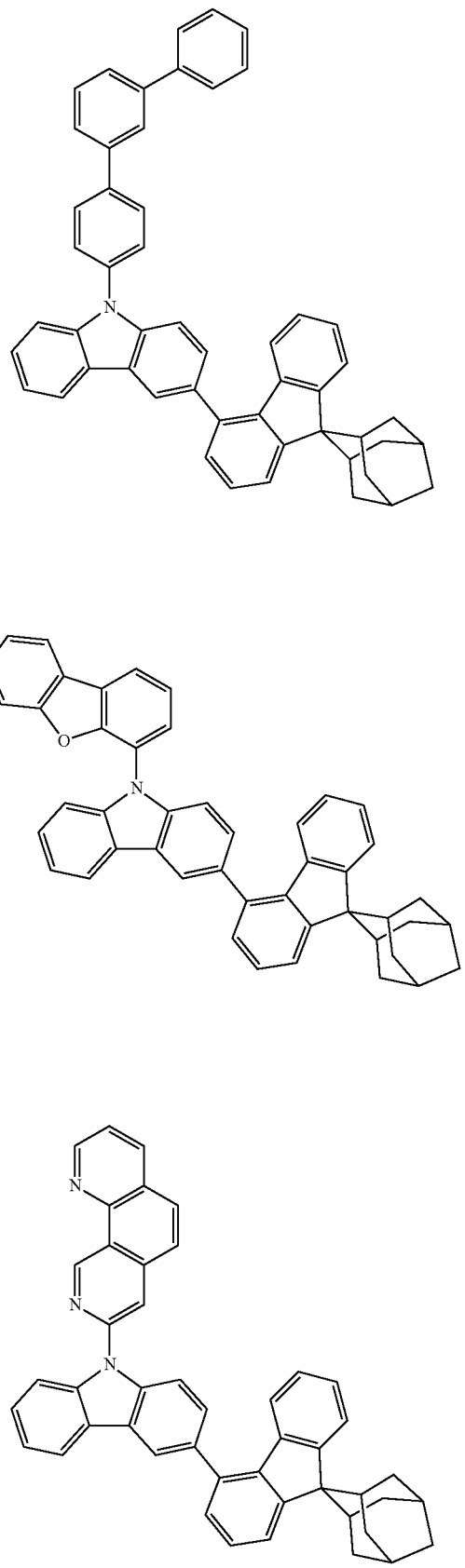
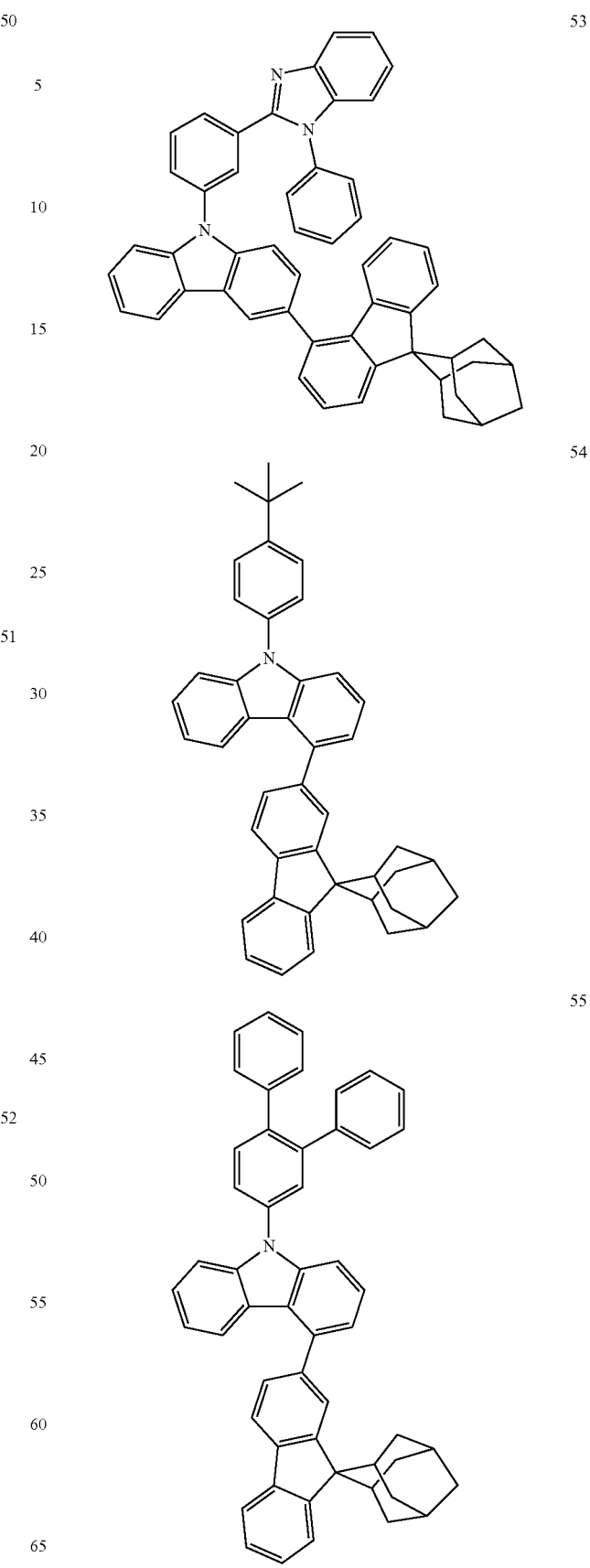

169
-continued
56
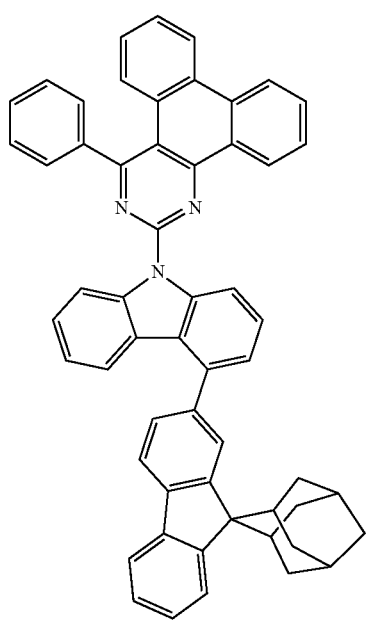
57
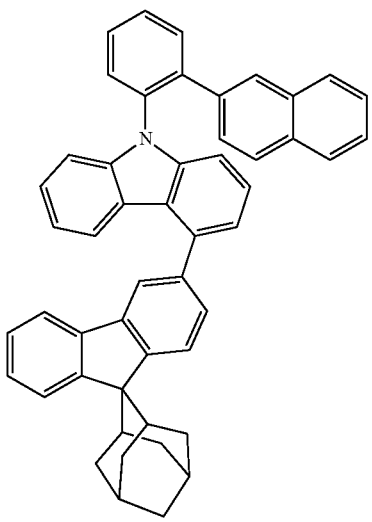
170
-continued
58
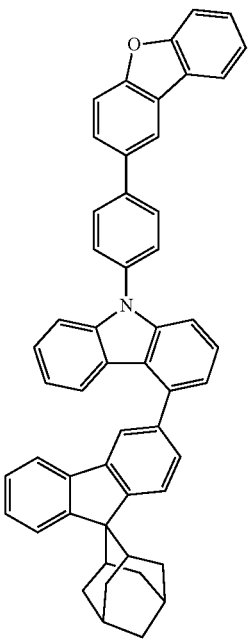
59
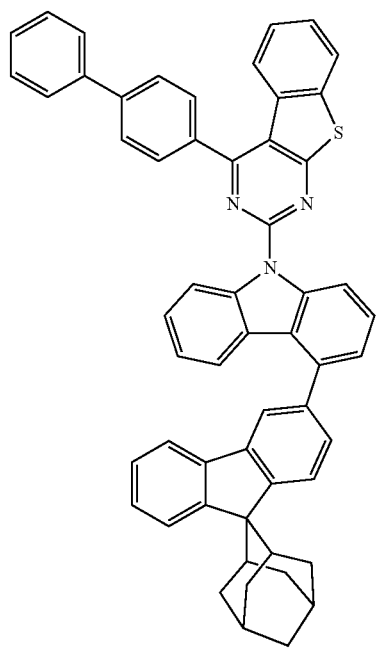

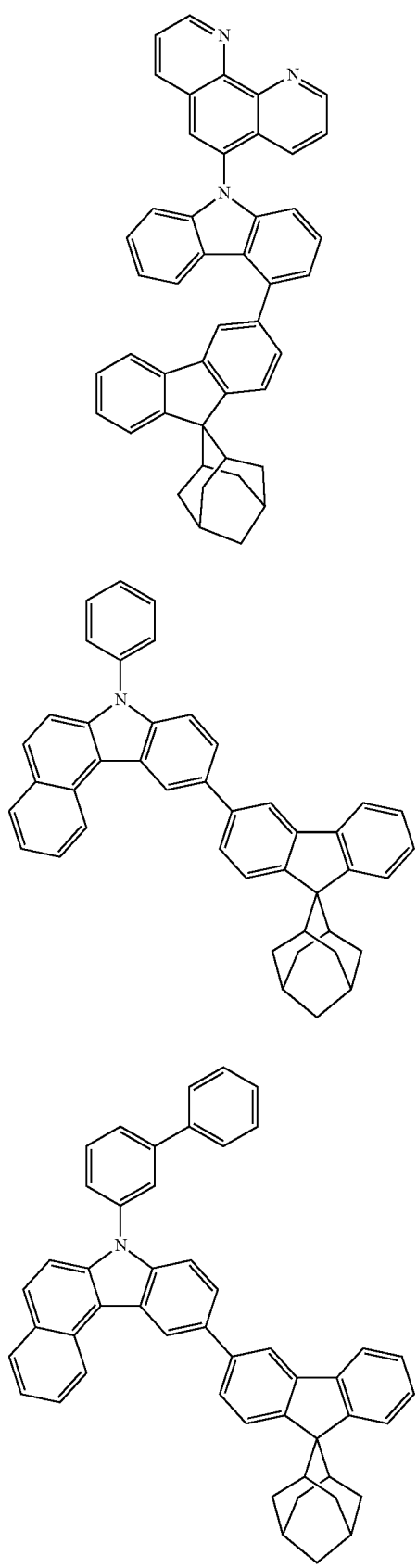
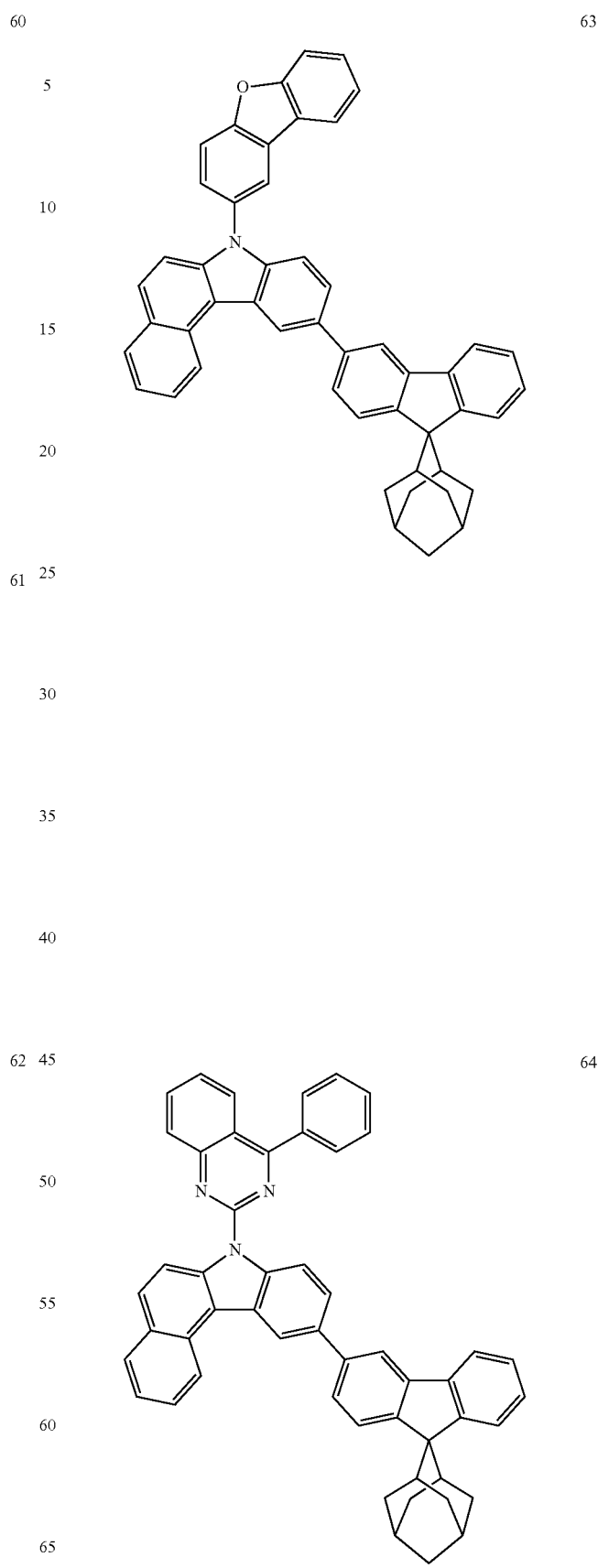

65
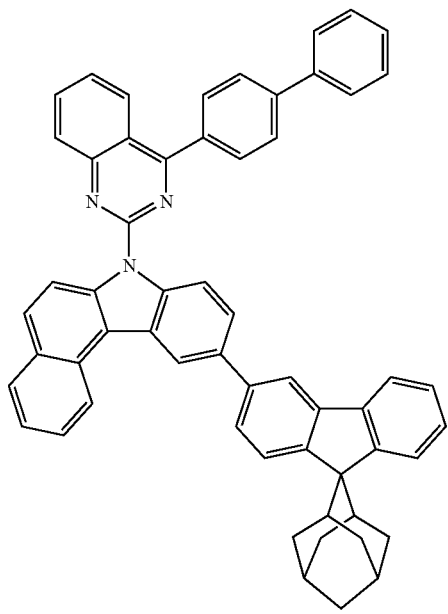
66
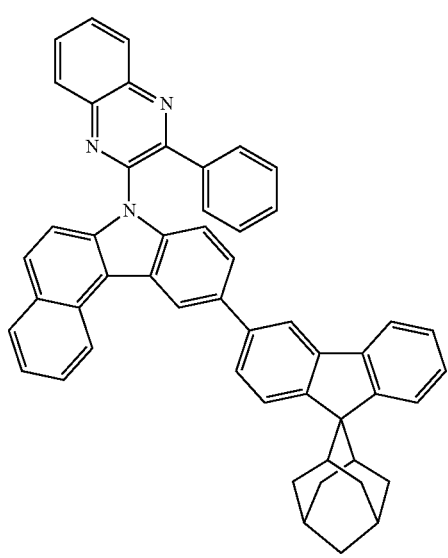
67
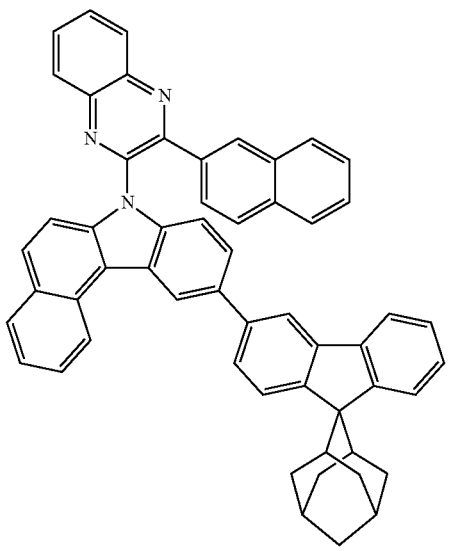
68
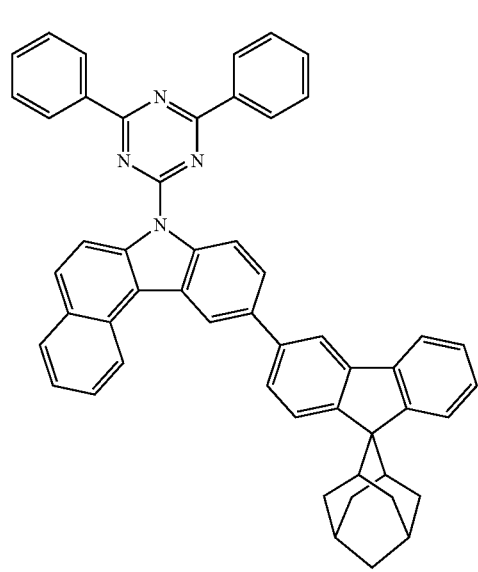

69
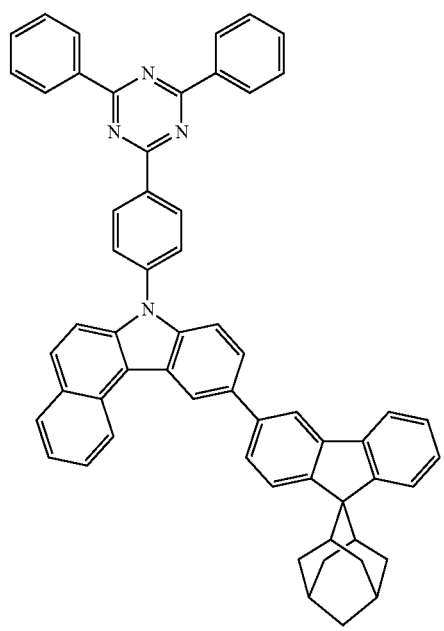
71
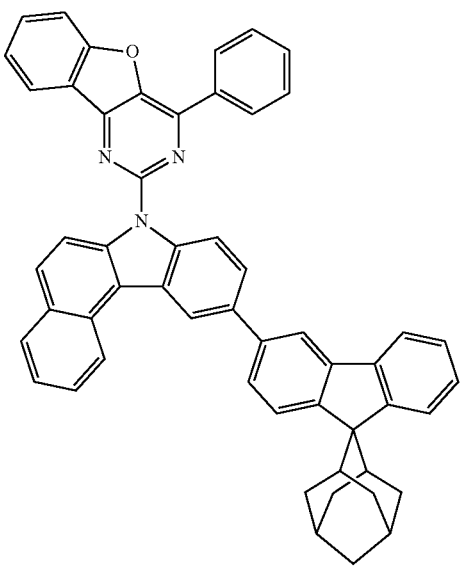
70
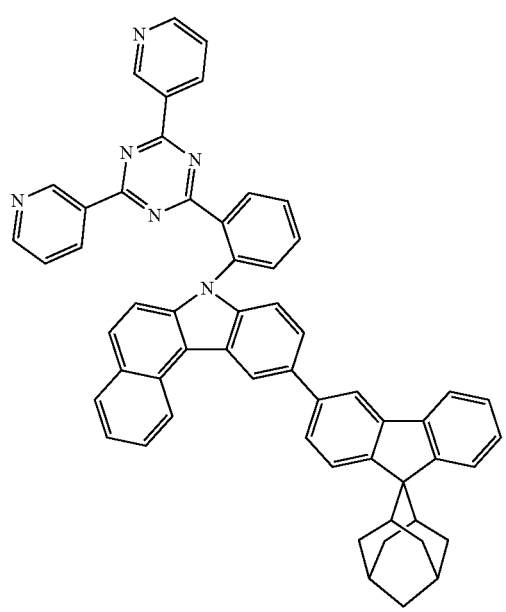
72
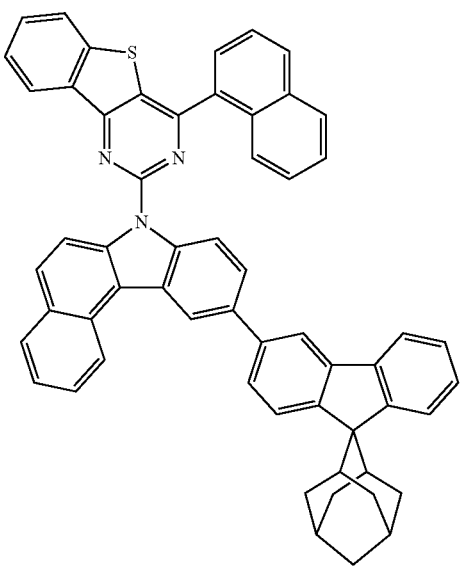

177
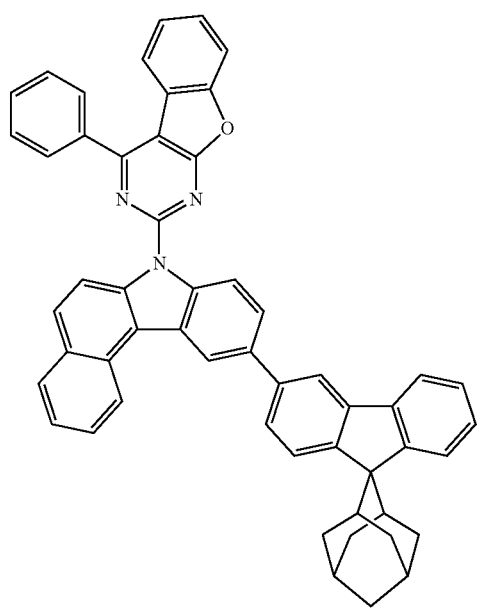
178
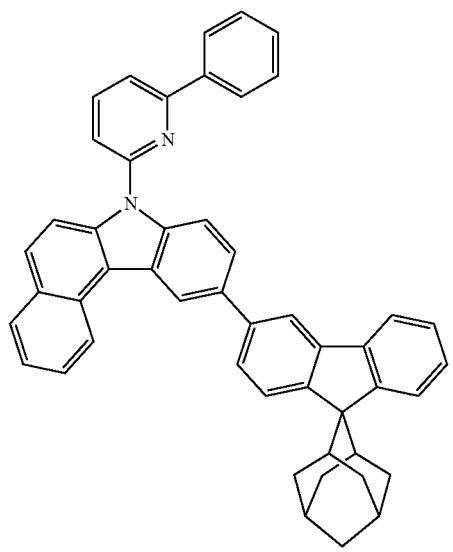
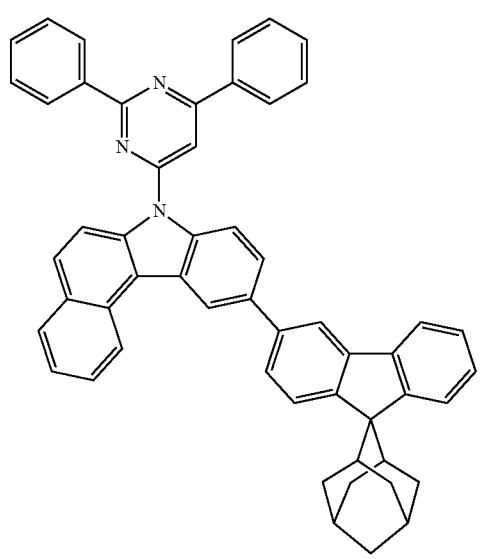
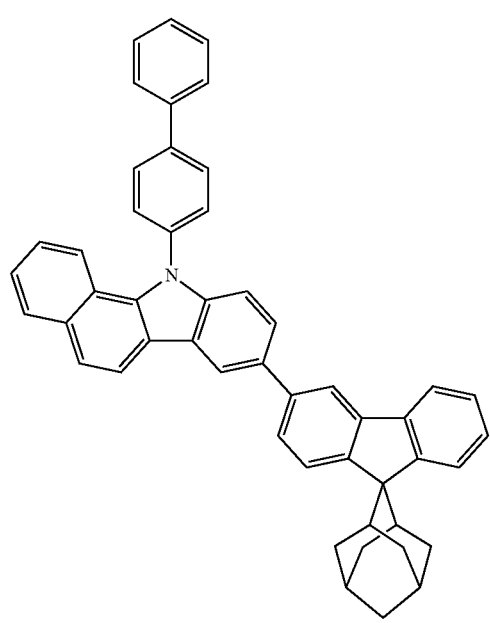

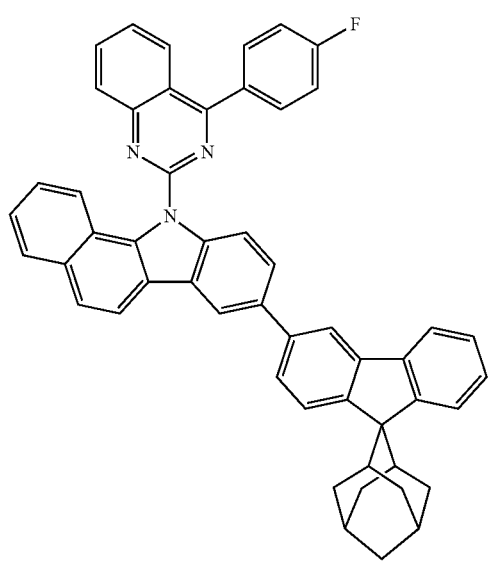
77
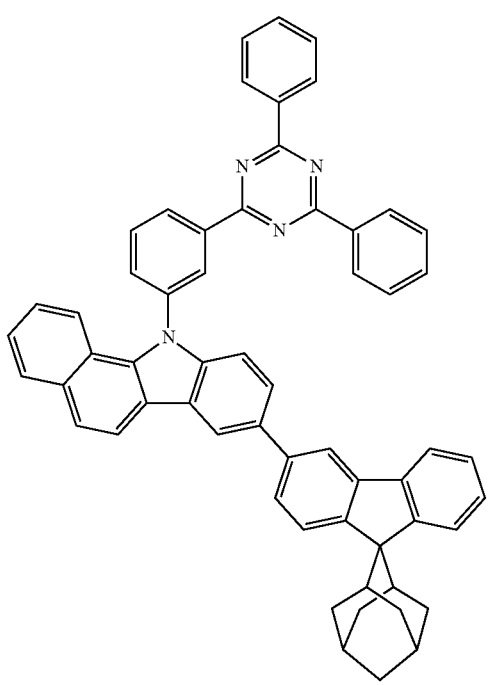
79
78
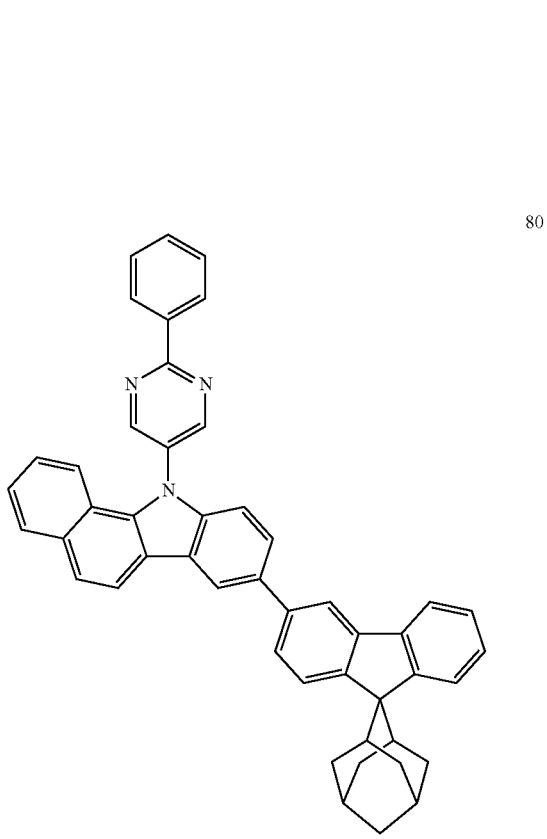
80

-continued
81
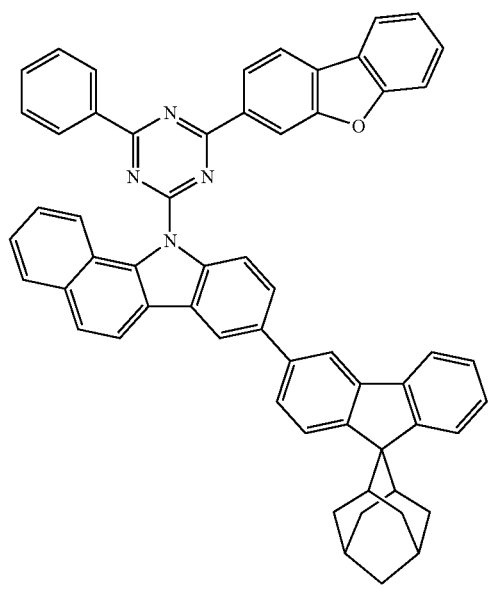
82
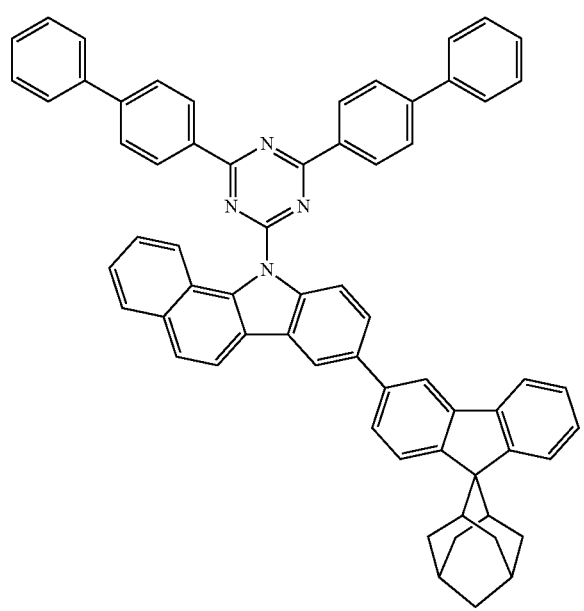
83
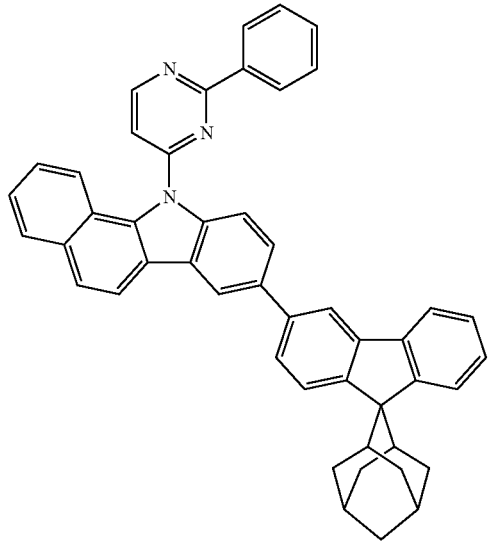
84
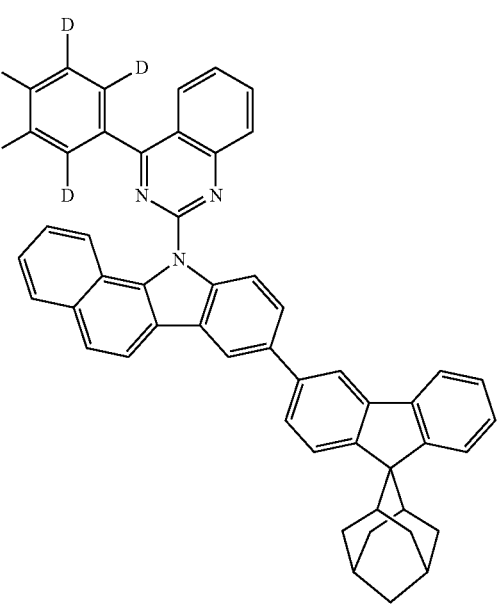

183
-continued
85
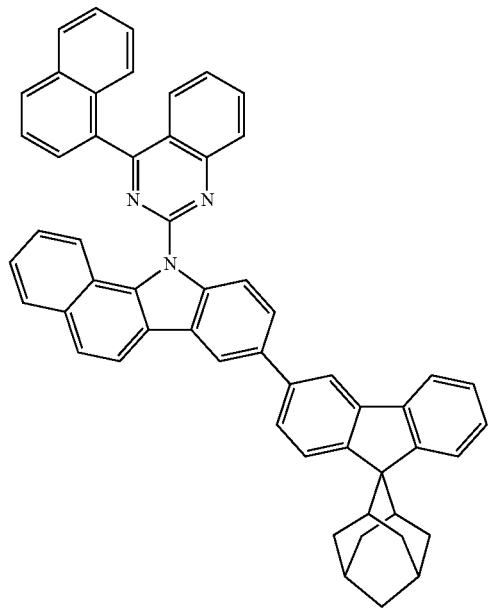
86
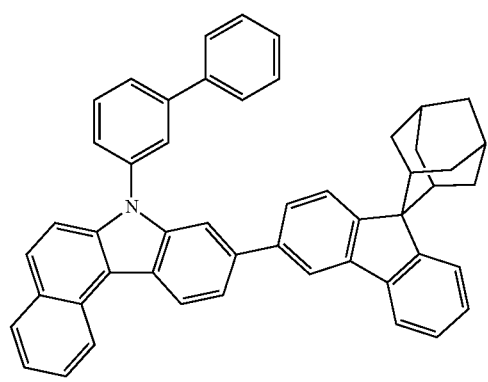
87
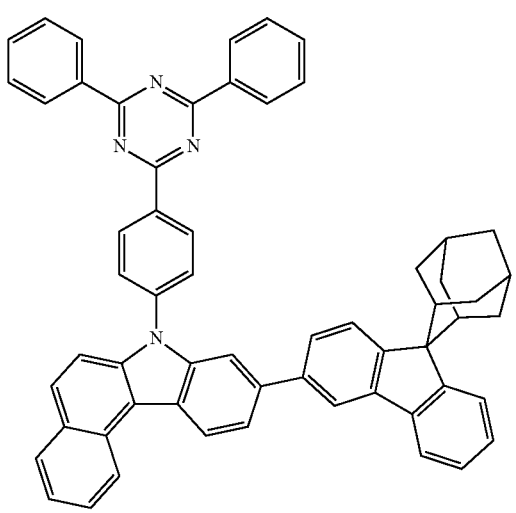
184
-continued
88
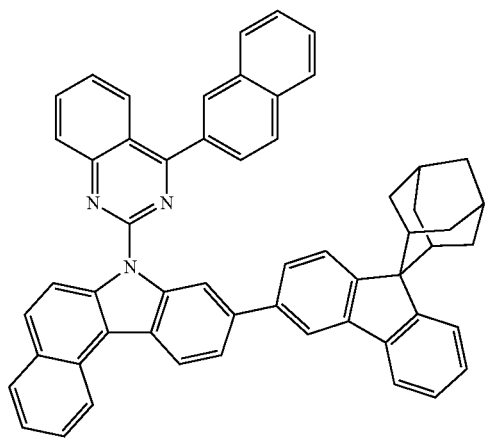
89
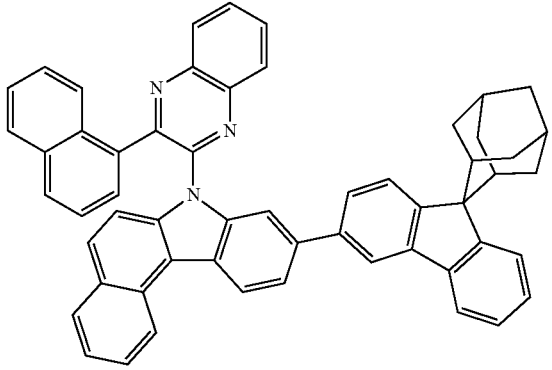
90
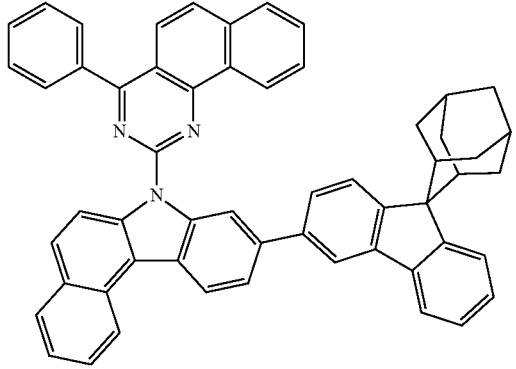

91
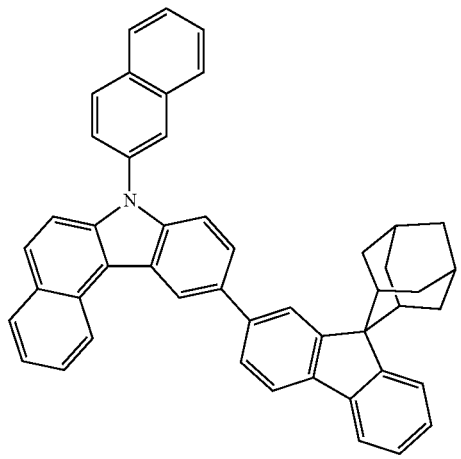
92
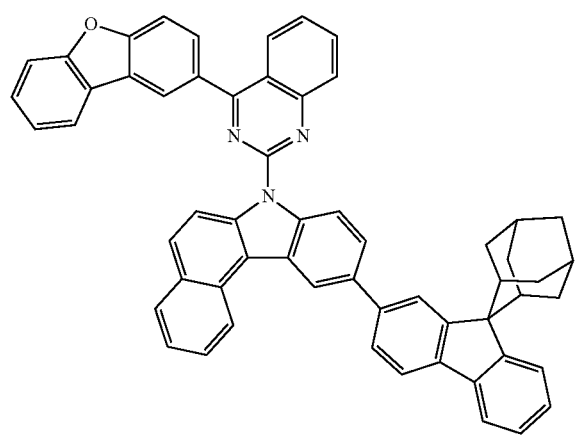
93
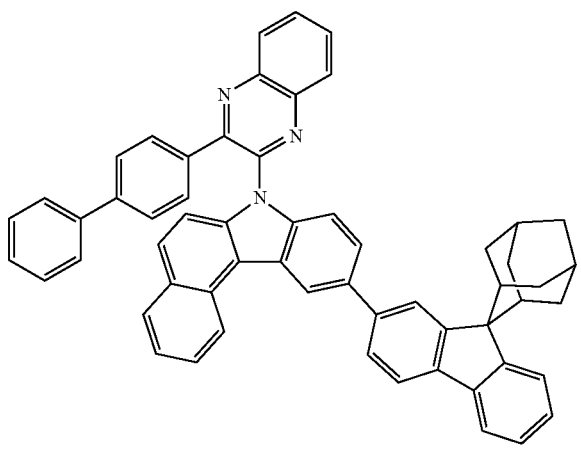
94
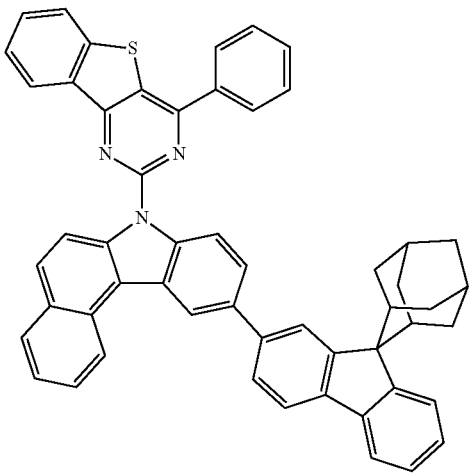
95
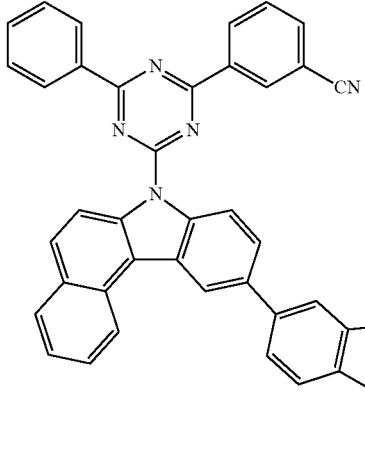
96
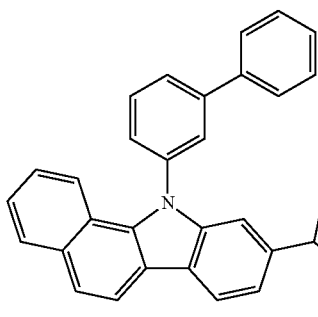

97
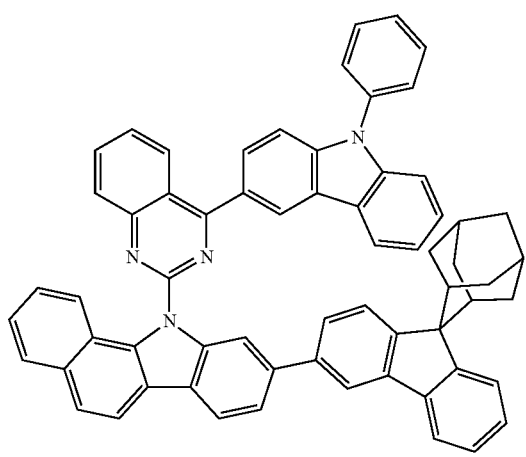
98
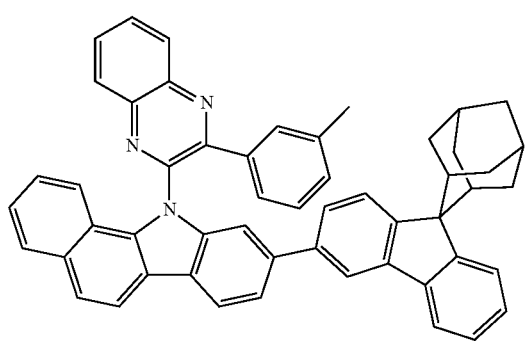
99
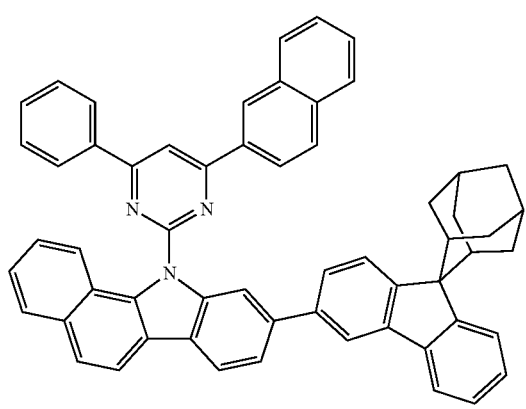
100
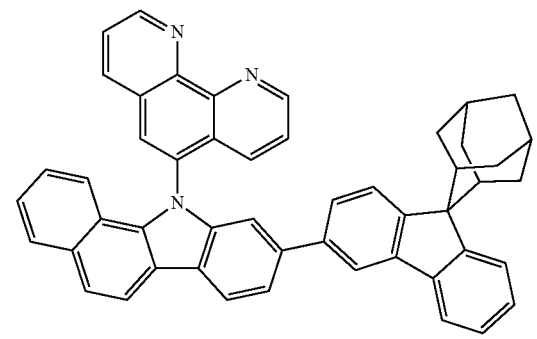
101
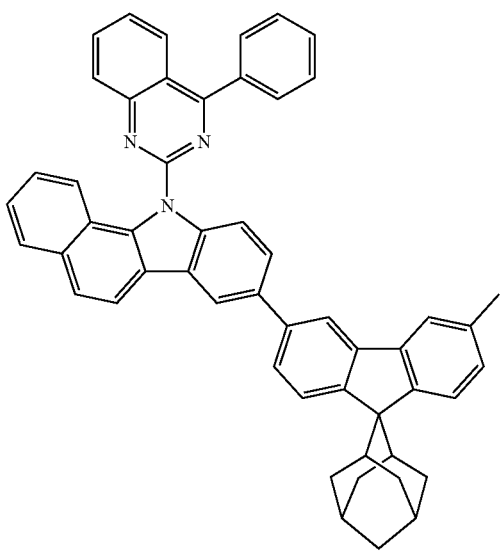
102
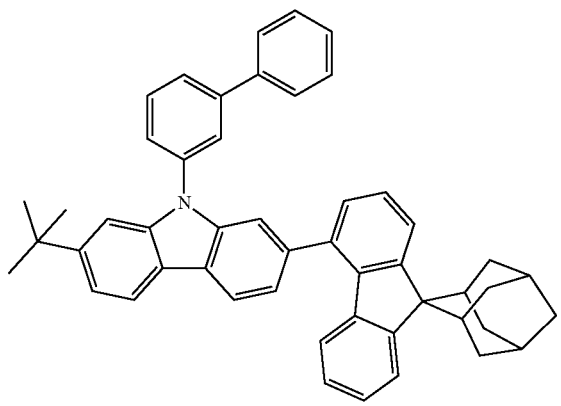
103

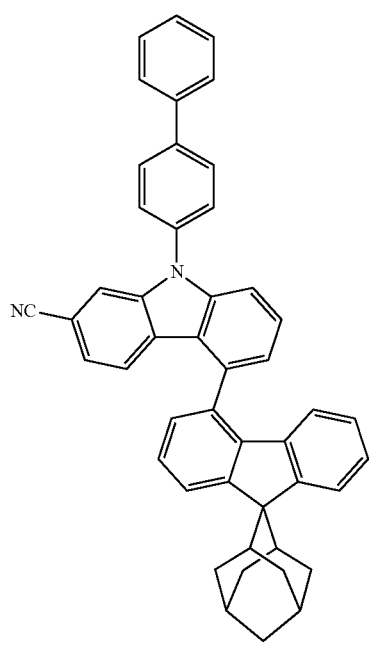
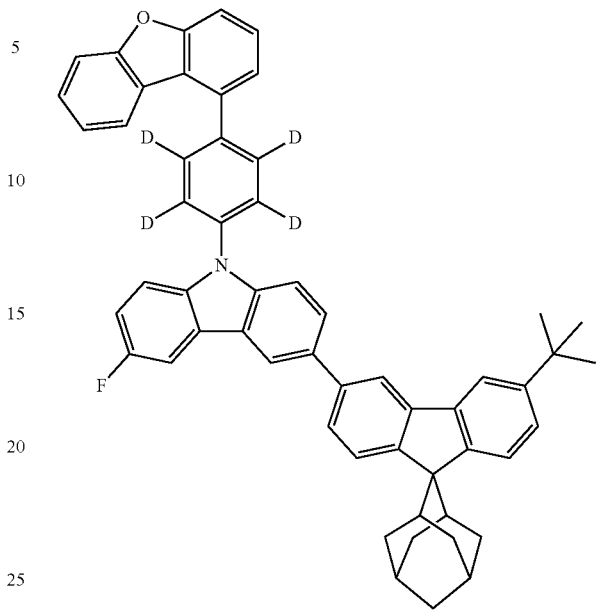
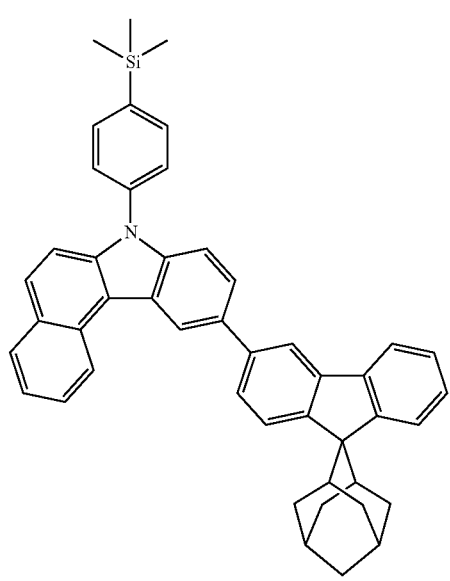
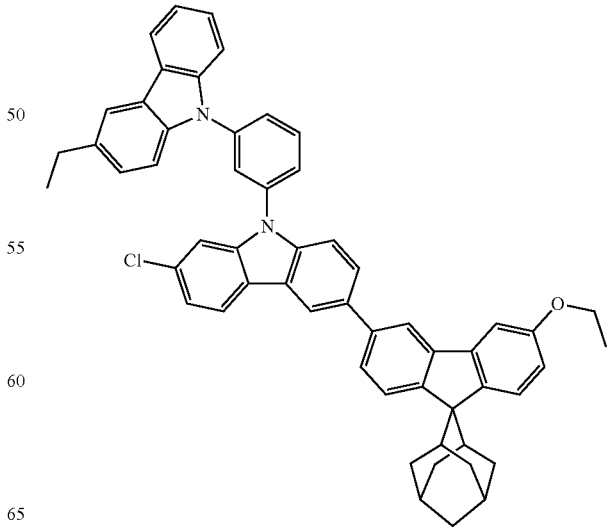

191
-continued
108
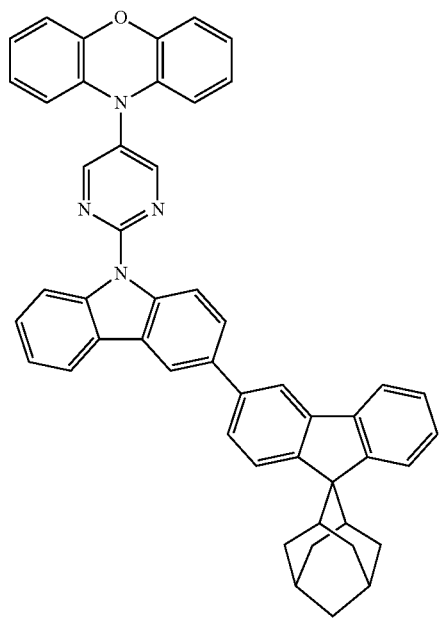
109
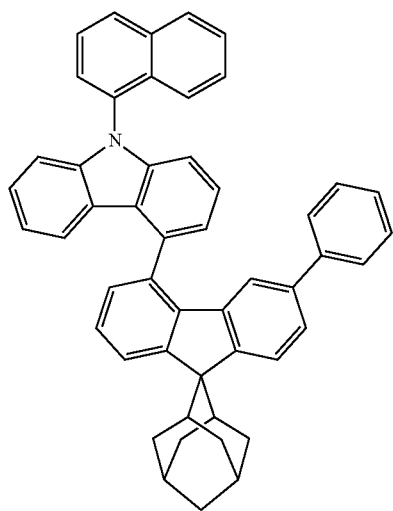
192
-continued
110
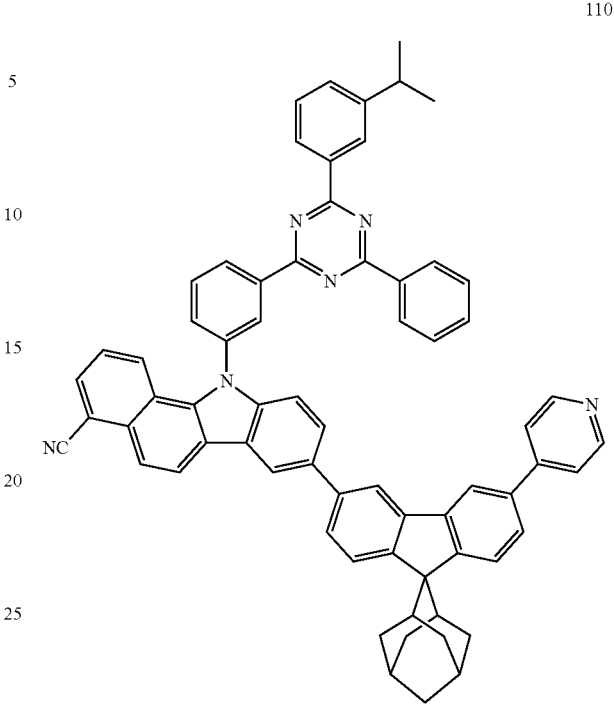
111
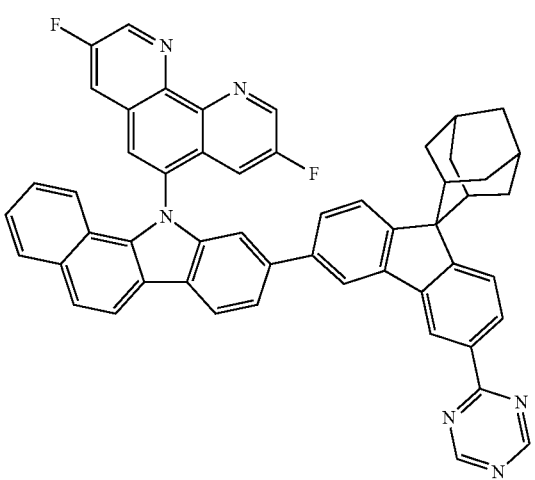

193
-continued
112
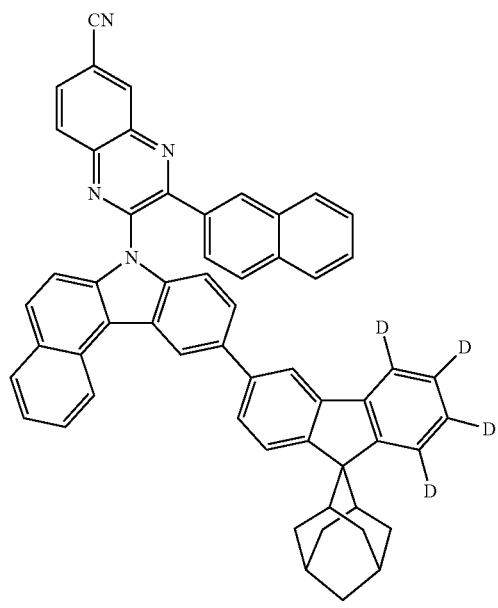
113
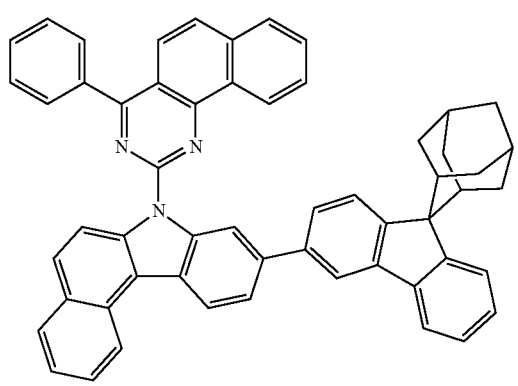
114
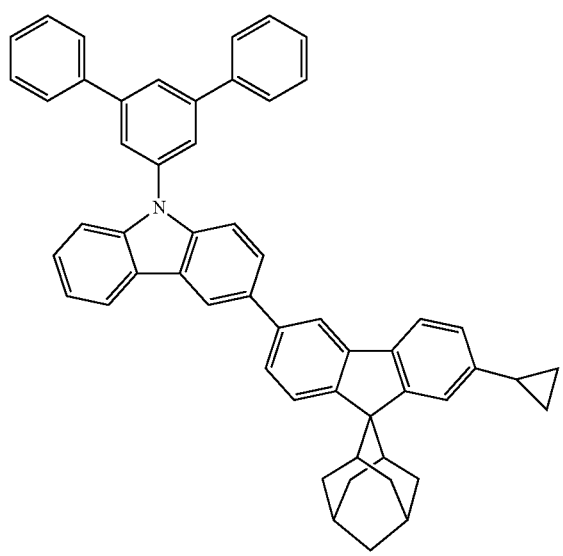
194
-continued
115
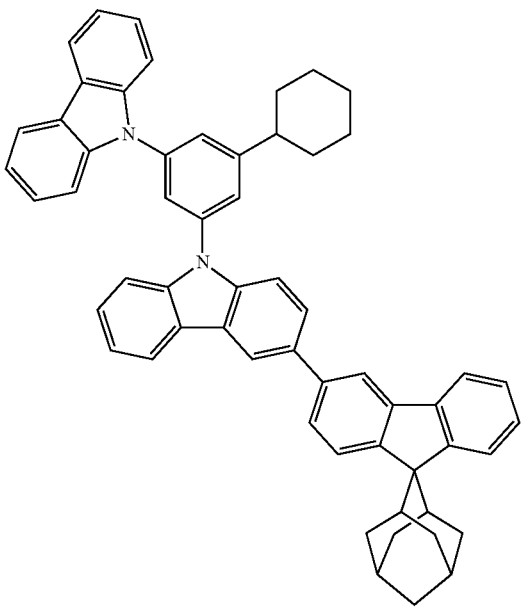
116
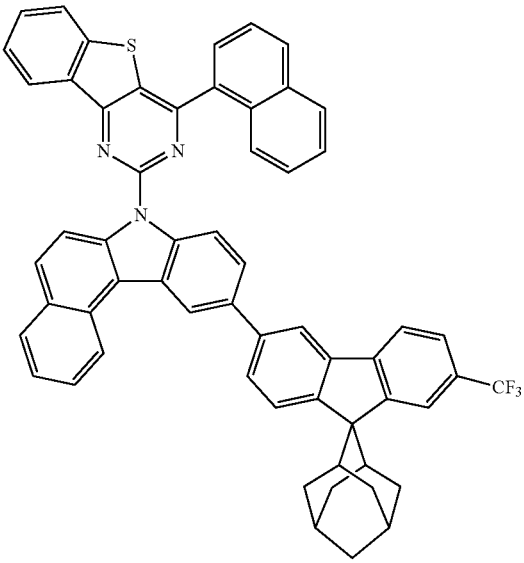

-continued
117
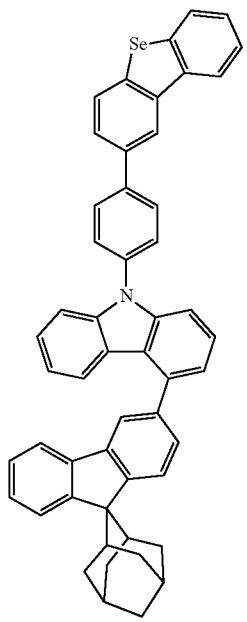
118
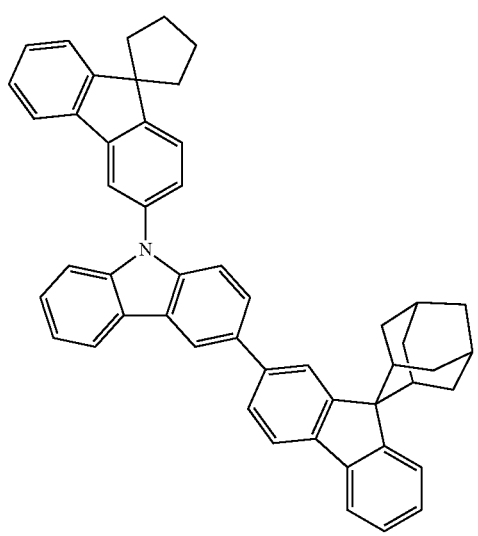
-continued
119
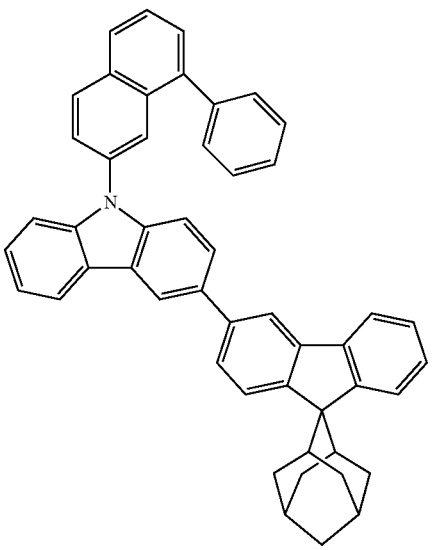
120
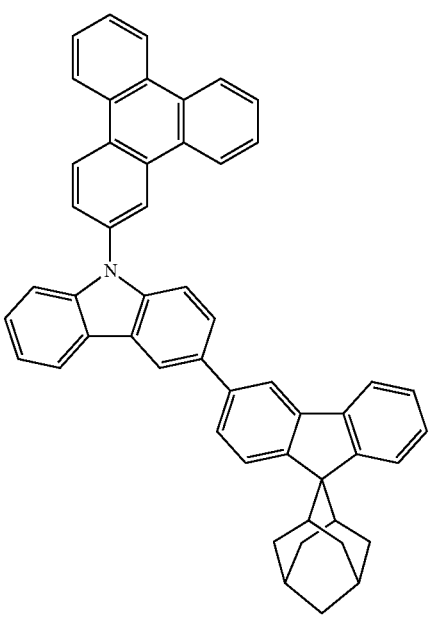

-continued
121
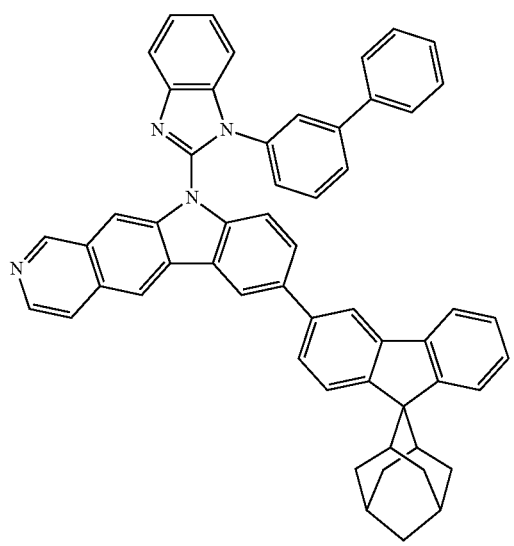
122
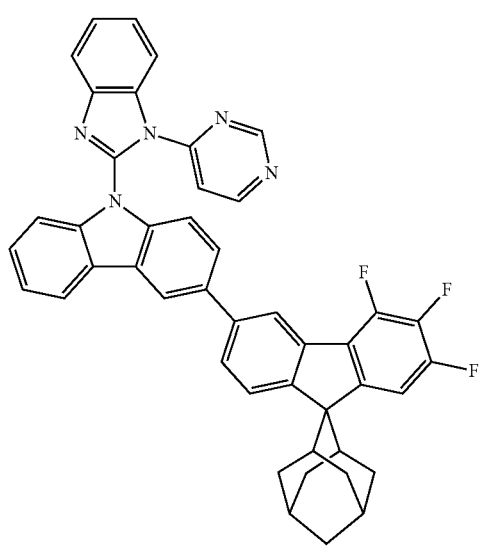
-continued
124
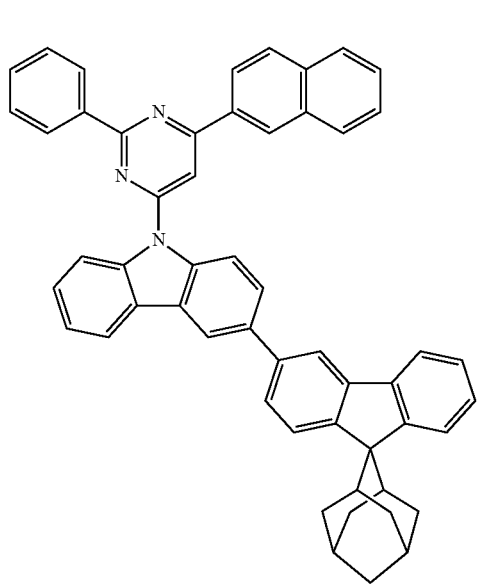
125
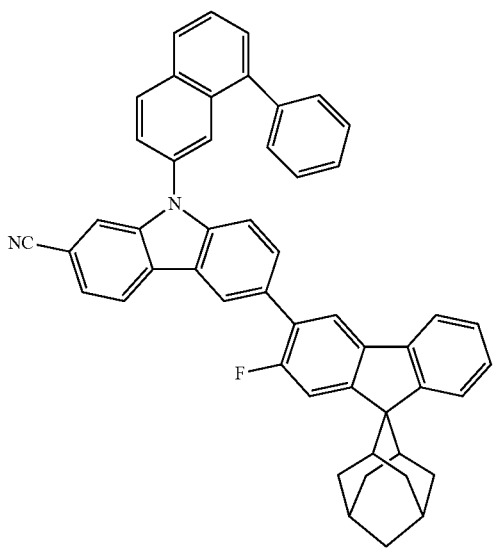
123

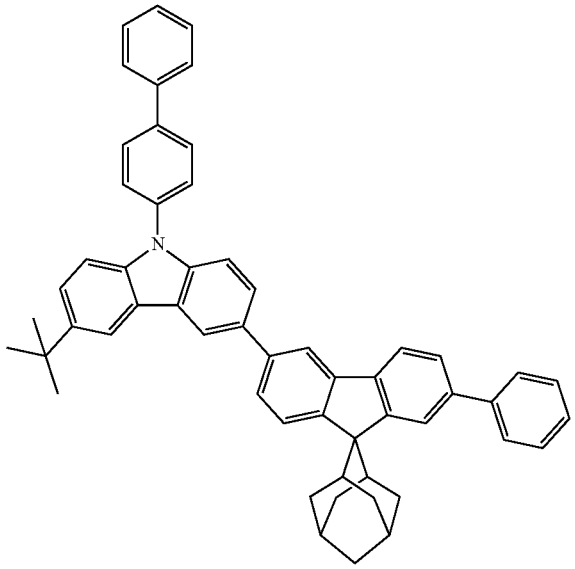
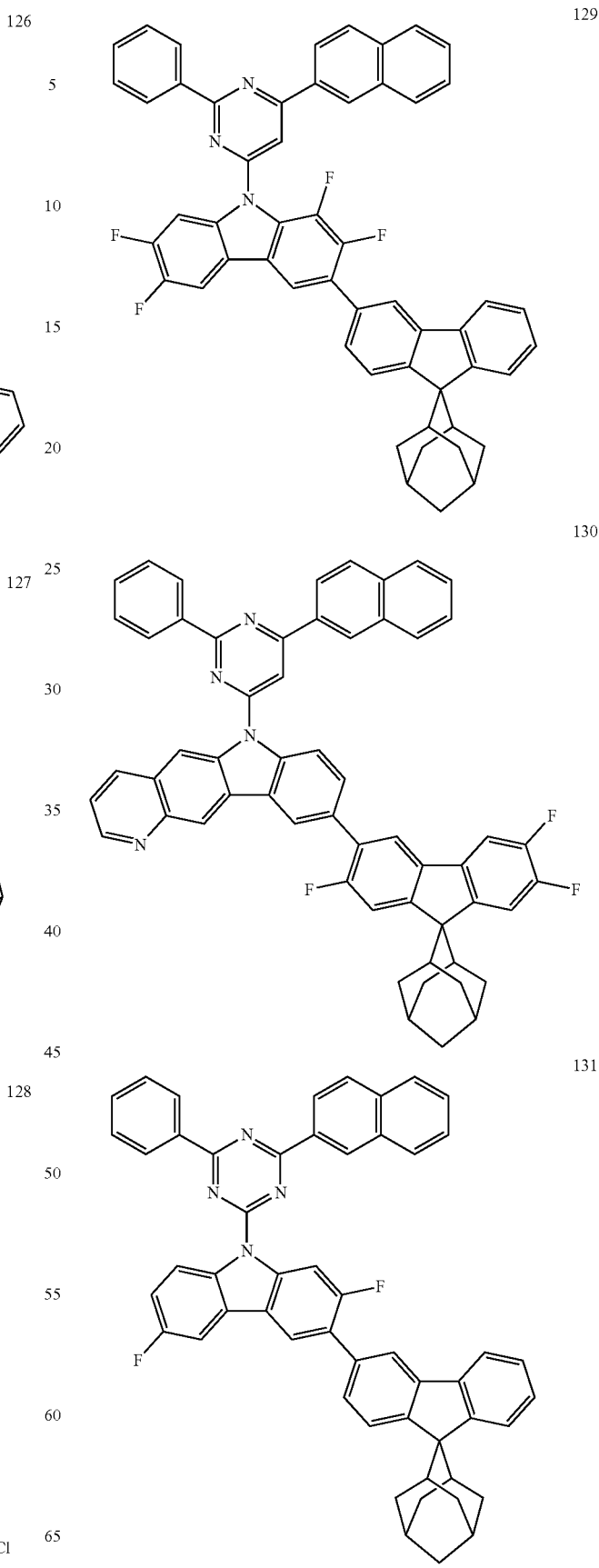

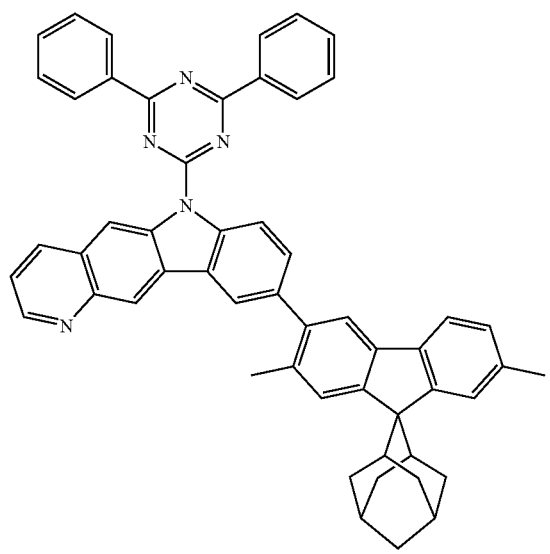
132
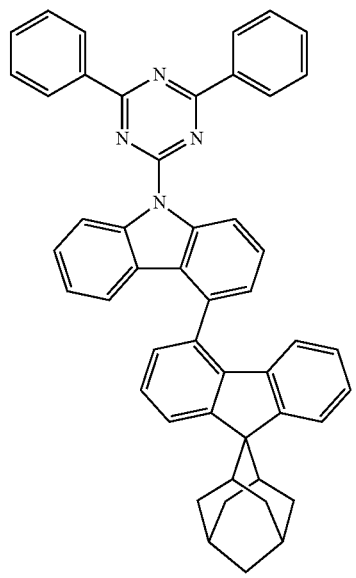
135
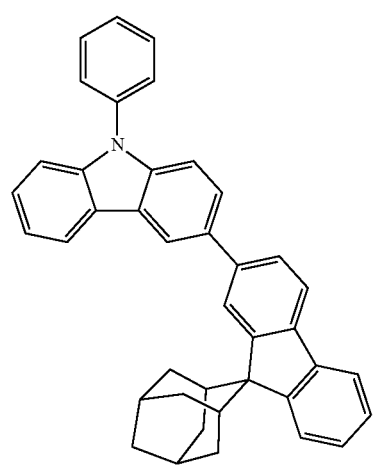
133
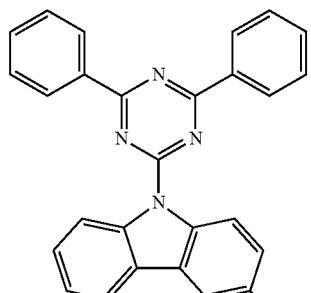
136
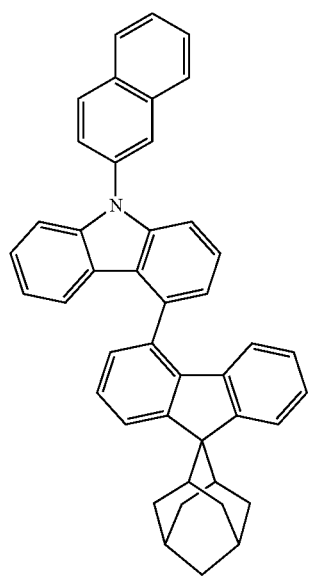
134
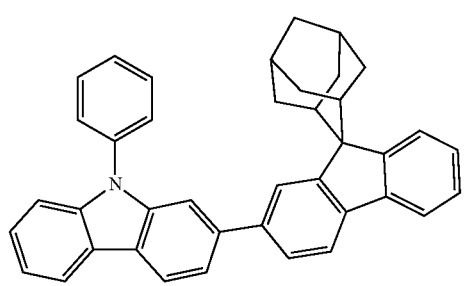
137

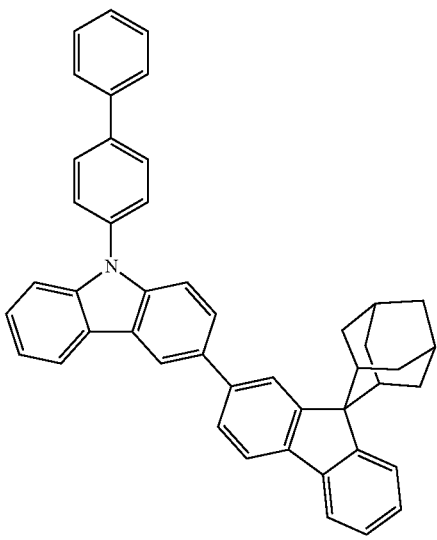

138

139

140

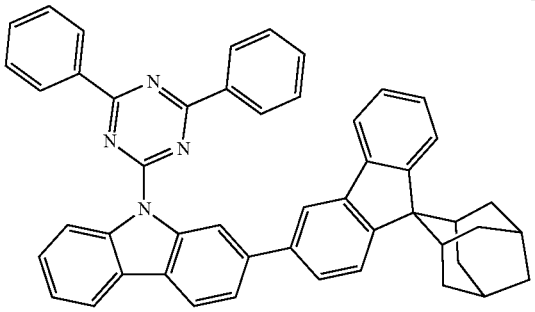

141

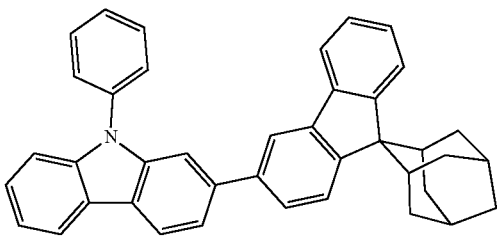

142

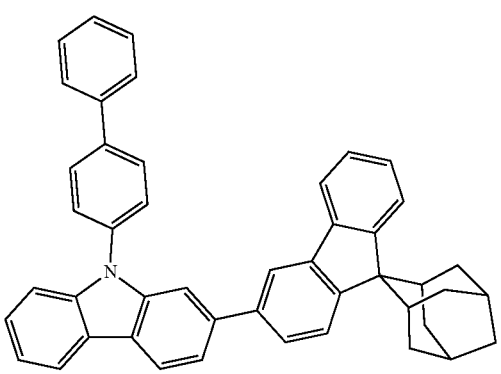

143

5. An organic electroluminescent device, comprising an anode and a cathode which are disposed oppositely, and an organic light-emitting layer disposed between the anode and the cathode; wherein
the organic light-emitting layer comprises the nitrogen-containing compound according to claim 1.

6. The organic electroluminescent device according to claim 5, wherein a host material of the organic light-emitting layer comprises the nitrogen-containing compound.

7. An electronic apparatus, comprising the organic electroluminescent device of claim 5.

8. An organic electroluminescent device, comprising an anode and a cathode which are disposed oppositely, and an organic light-emitting layer disposed between the anode and the cathode; wherein
the organic light-emitting layer comprises the nitrogen-containing compound according to claim 4.

9. The organic electroluminescent device according to claim 8, wherein a host material of the organic light-emitting layer comprises the nitrogen-containing compound.

10. An electronic apparatus, comprising the organic electroluminescent device of claim 6.

11. An electronic apparatus, comprising the organic electroluminescent device of claim 8.

12. An electronic apparatus, comprising the organic electroluminescent device of claim 9.

* * * * *